(12) United States Patent
Knust et al.

(10) Patent No.: US 8,324,250 B2
(45) Date of Patent: Dec. 4, 2012

(54) PIPERIDINE DERIVATIVES AS NK3 RECEPTOR ANTAGONISTS

(75) Inventors: Henner Knust, Rheinfelden (DE); Anja Limberg, Basel (CH); Matthias Nettekoven, Grenzach-Wyhlen (DE); Hasane Ratni, Habsheim (FR); Claus Riemer, Freiburg (DE); Walter Vifian, Gelterkinden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 116 days.

(21) Appl. No.: 12/721,587

(22) Filed: Mar. 11, 2010

(65) Prior Publication Data

US 2010/0256126 A1     Oct. 7, 2010

(30) Foreign Application Priority Data

Mar. 19, 2009   (EP) .................... 09155585

(51) Int. Cl.
*A61K 31/445* (2006.01)
*C07D 413/02* (2006.01)

(52) U.S. Cl. ........ 514/326; 546/184; 546/192; 546/210; 514/315; 514/317

(58) Field of Classification Search .................. 546/184, 546/192, 207, 210; 514/315, 317, 326
See application file for complete search history.

(56) References Cited

U.S. PATENT DOCUMENTS 7,470,684 B2 * 12/2008 Caroon et al. ............. 514/230.5
8,022,213 B2 *  9/2011 Bissantz et al. ................ 546/18
8,063,075 B2 * 11/2011 Jablonski et al. ............. 514/340

FOREIGN PATENT DOCUMENTS

WO    03/053361    7/2003
WO    2004/099157  11/2004

OTHER PUBLICATIONS

Tooney et al., Neurosci. Letters. vol. 283, (2000), pp. 185-188.
Giardina et al., Exp. Opin. Ther. Patents, vol. 10, (2000), pp. 939-960.
Jung et al., Neurosci. vol. 74, (1996) pp. 403-414.
Marco at al., Neuropeptides, vol. 32, (1998) pp. 481-488.
Kamali, F., Current Opinion in Investigational Drugs, vol. 7, (2001) pp. 950-956.
Jorgensen et al., JACS, vol. 124, (2002) pp. 12557-12565.
Shetty et al., THL, vol. 47, (2006) pp. 8021-8024.

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present application relates to compounds of formula

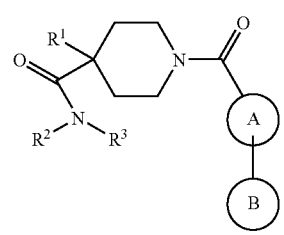

I wherein the definitions are as described herein. The present compounds are high potential NK-3 receptor antagonists that are useful for the treatment of depression, pain, psychosis, Parkinson's disease, schizophrenia, anxiety and attention deficit hyperactivity disorder (ADHD).

7 Claims, No Drawings

PIPERIDINE DERIVATIVES AS NK3 RECEPTOR ANTAGONISTS

PRIORITY TO RELATED APPLICATION(S)

This application claims the benefit of European Patent Application No. 09155585.4, filed Mar. 19, 2009, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia, June* 2003, *Decision Recources, Inc.,* Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, *Decision Recources, Inc.,* Waltham, Mass.).

SUMMARY OF THE INVENTION

The present application provides compounds of formula I

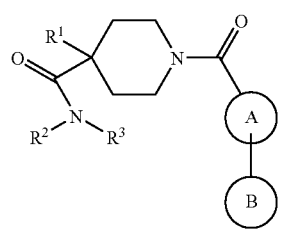

wherein
R$^1$ is
  aryl or heteroaryl, each of which is optionally substituted by halogen or lower alkyl substituted by halogen, or is (CH$_2$)$_n$-cycloalkyl and n is 0, 1 or 2,
  lower alkyl,
  lower alkenyl or
  lower alkyl substituted by halogen;
R$^2$ is
  CRR'-aryl or heteroaryl, eac of which si optionally substituted by halogen, lower alkyl, lower alkyl substituted by halogen or cyano,
  CRR'-cycloalkyl,
  CRR'-lower alkyl, or
  NR-aryl or NR-heteroaryl, wherein aryl and heteroaryl are each optionally substituted by halogen, lower alkyl, lower alkyl substituted by halogen or cyano, or is NR-cycloalkyl, indan-1-yl or indan-2-yl, each of which is optionally substituted by hydroxy;
R$^3$ is hydrogen or lower alkyl, or
R$^2$ and R$^3$ together with the N-atom to which they are attached form a 2,3-dihydro-1-H-isoindol group or a piperidine ring, which is optionally substituted by a heteroaryl group;
R and R' are each independently hydrogen, (CH$_2$)$_n$-cycloalkyl, lower alkyl, lower alkyl substituted by halogen or hydroxy, or both R and R' together with the carbon atom to which they are attached form a cycloalkyl ring;

(A)

is aryl, heteroaryl or heterocycloalkyl, each of which is optionally substituted by lower alkyl or =O, or is cycloalkyl;

(B)

is aryl, heteroaryl or heterocycloalkyl, each of which is optionally substituted by lower alkyl, lower alkoxy, halogen, lower alkyl substituted by halogen, cyano, amino, C(O)-lower alkyl, C(O)NH$_2$, S(O)$_2$-lower alkyl or =O, or is cycloalkyl;

or a pharmaceutically active salt thereof.

The invention includes all stereoisomeric forms, including individual diastereoisomers and enantiomers of the compound of formula (I) as well as racemic and non-racemic mixtures thereof.

The present invention also provides pharmaceutical compositions containing a therapeutically effective amount of a compound of formula I and a pharmaceutically acceptable carrier. The invention further provides methods for the manufacture of the compounds and compositions of the invention.

The present compounds are high potential NK-3 receptor antagonists that are useful for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in Combination.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

As used herein, the term "lower alkoxy" denotes a lower alkyl group as defined above which is connected via an oxygen atom.

The term "lower alkyl substituted by halogen" denotes an alkyl group as defined above, wherein at least one hydrogen atom is replaced by halogen, for example —CF$_3$, —CHF$_2$, —CH$_2$F, —CH$_2$CF$_3$, —CH$_2$CH$_2$CF$_3$, —CH$_2$CH$_2$CH$_2$CF$_3$, —CH$_2$CH$_2$CF$_2$CF$_3$, —CH$_2$CH$_2$CH$_2$CF$_2$CF$_3$, —CH$_2$CF$_2$CF$_3$ and the like. Preferred lower alkyl substituted by halogen groups are groups having 1-5 carbon atoms.

The term "halogen" denotes chlorine, iodine, fluorine and bromine.

The term "cycloalkyl" denotes a saturated carbon ring containing from 3-7 carbon atoms, for example, cyclopropyl, cyclobutyl, cyclpentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, naphthyl or 1,2,3,4-tetrahydronaphthalenyl. Preferred is the phenyl group.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom, selected from N, O or S, for example quinoxalinyl, dihydroisoquinolinyl, pyrazin-2-yl, pyrazolyl, 2,4-dihydro-pyrazol-3-one, pyridinyl, isoxazolyl, benzo[1,3]dioxol, [1,3,4]thiadiazol, pyridyl, pyridazinyl, pyrimidinyl, benzotriazol-5-yl, benzoimidazol-5-yl, [1,2,4]-oxadiazolyl, [1,3,4]-oxadiazol-2-yl, [1,2,4]triazol-1-yl, [1,2,3]triazolyl, [1,6]naphthyridin-2-yl, imidazo[4,5-b]pyridine-6-yl, tetrazolyl, thiazolyl, oxazolyl, thiadiazolyl, thienyl, furyl, pyrrolyl, imidazol-1-yl, or benzofuranyl. Preferred heteroaryl group is pyridine-2, 3 or 4-yl.

The term "heterocycloalkyl" denotes a non-aromatic ring, containing one or two heteroatoms selected from the group consisting of N, S and O, for example the following groups: morpholinyl, [1,4]diazepam-1-yl, piperazinyl, pyrrolidinyl, piperidin-1-yl, tetrahydrofuranyl, tetrahydrothiophenyl, piperidin-4-yl, thiomorpholinyl or 1,1-dioxo-λ$^6$-thiomorpholinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds encompassed by formula I are those of formula Ia

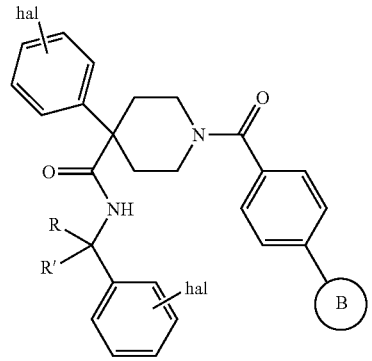

Ia wherein
hal is halogen;
R and R' are each independently hydrogen, (CH$_2$)$_n$-cycloalkyl, lower alkyl, lower alkyl substituted by halogen or hydroxy, or
R and R' together with the carbon atom to which they are attached form a cycloalkyl ring;

is aryl, heteroaryl or heterocycloalkyl, each of which is optionally substituted by lower alkyl, lower alkoxy, halogen, lower alkyl substituted by halogen, cyano, amino, C(O)-lower alkyl, C(O)NH$_2$, S(O)$_2$-lower alkyl or =O, or is cycloalkyl;

or a pharmaceutically active salt thereof.

Compounds of formula Ia include the following:

1-[4-(5-methyl-[1,2,4]oxadiazol-3-yl)-benzoyl]-4-phenyl-piperidine-4-carboxylic acid ((S)-1-phenyl-ethyl)-amide;

1-[4-(3-methyl-[1,2,4]oxadiazol-5-yl)-benzoyl]-4-phenyl-piperidine-4-carboxylic acid ((S)-1-phenyl-ethyl)-amide;

1-(4'-fluoro-biphenyl-4-carbonyl)-4-phenyl-piperidine-4-carboxylic acid ((S)-1-phenyl-ethyl)-amide;

1-[4-(3-methyl-[1,2,4]oxadiazol-5-yl)-benzoyl]-4-phenyl-piperidine-4-carboxylic acid [(S)-1-(4-fluoro-phenyl)-ethyl]-amide;

1-(4'-fluoro-biphenyl-4-carbonyl)-4-phenyl-piperidine-4-carboxylic acid [(S)-1-(4-fluoro-phenyl)-ethyl]-amide;

4-(4-fluoro-phenyl)-1-[4-(3-methyl-[1,2,4]oxadiazol-5-yl)-benzoyl]-piperidine-4-carboxylic acid ((S)-1-phenyl-ethyl)-amide;

1-[4-(3-methyl-[1,2,4]oxadiazol-5-yl)-benzoyl]-4-phenyl-piperidine-4-carboxylic acid ((S)-1-phenyl-propyl)-amide;

1-[4-(1,1-dioxo-1λ$^6$-thiomorpholin-4-yl)-benzoyl]-4-phenyl-piperidine-4-carboxylic acid ((S)-1-phenyl-propyl)-amide;

1-(4'-fluoro-biphenyl-4-carbonyl)-4-phenyl-piperidine-4-carboxylic acid ((S)-1-phenyl-propyl)-amide;

4-(4-fluoro-phenyl)-1-[4-(3-methyl-[1,2,4]oxadiazol-5-yl)-benzoyl]-piperidine-4-carboxylic acid [(S)-1-(4-fluoro-phenyl)-ethyl]-amide;

1-(4'-fluoro-biphenyl-4-carbonyl)-4-(4-fluoro-phenyl)-piperidine-4-carboxylic acid ((R)-2-hydroxy-1-phenyl-ethyl)-amide;

1-(4'-fluoro-biphenyl-4-carbonyl)-4-(4-fluoro-phenyl)-piperidine-4-carboxylic acid (2-methyl-1-phenyl-propyl)-amide;

1-(4'-fluoro-biphenyl-4-carbonyl)-4-(4-fluoro-phenyl)-piperidine-4-carboxylic acid (2-cyclopropyl-1-phenyl-ethyl)-amide;

4-(4-fluoro-phenyl)-1-[4-(3-methyl-[1,2,4]oxadiazol-5-yl)-benzoyl]-piperidine-4-carboxylic acid [1-(4-fluoro-phenyl)-cyclopropyl]-amide;

4-(4-fluoro-phenyl)-1-[4-(3-methyl-[1,2,4]oxadiazol-5-yl)-benzoyl]-piperidine-4-carboxylic acid [(S)-1-(3-fluoro-phenyl)-ethyl]-amide;

1-(4'-fluoro-biphenyl-4-carbonyl)-4-(4-fluoro-phenyl)-piperidine-4-carboxylic acid [(S)-cyclopropyl-(3-fluoro-phenyl)-methyl]-amide;

4-(4-fluoro-phenyl)-1-[4-(3-methyl-[1,2,4]oxadiazol-5-yl)-benzoyl]piperidine-4-carboxylic acid [(S)-cyclopropyl-(3-fluoro-phenyl)-methyl]amide;

4-(4-fluoro-phenyl)-1-[4-(5-methyl-[1,2,4]oxadiazol-3-yl)-benzoyl]-piperidine-4-carboxylic acid [(S)-cyclopropyl-(3-fluoro-phenyl)-methyl]-amide; and 4-(4-fluoro-phenyl)-1-[4-(3-methyl-[1,2,4]oxadiazol-5-yl)-benzoyl]-piperidine-4-carboxylic acid [(SR)-2,2,2-trifluoro-1-(4-fluoro-phenyl)-ethyl]-amide.

Other compounds encompassed by formula I are those of formula Ib

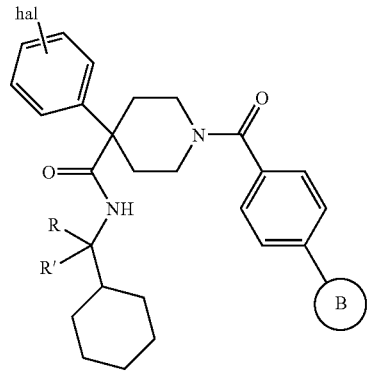

Ib wherein hal is halogen;

R and R' are each independently hydrogen, (CH$_2$)$_n$-cycloalkyl, lower alkyl, lower alkyl substituted by halogen or hydroxy, or R and R' together with the carbon atom to which they are attached form a cycloalkyl ring;

is aryl, heteroaryl or heterocycloalkyl, each of which is optionally substituted by lower alkyl, lower alkoxy, halogen, lower alkyl substituted by halogen, cyano, amino, C(O)-lower alkyl, C(O)NH$_2$, S(O)$_2$-lower alkyl or =O, or is cycloalkyl;

or a pharmaceutically active salt thereof, for example the following compounds:

1-[4-(3-methyl-[1,2,4]oxadiazol-5-yl)-benzoyl]-4-phenyl-piperidine-4-carboxylic acid ((S)-1-cyclohexyl-ethyl)-amide;

1-[4-(5-methyl-[1,2,4]oxadiazol-3-yl)-benzoyl]-4-phenyl-piperidine-4-carboxylic acid ((S)-1-cyclohexyl-ethyl)-amide;

1-[4-(1,1-dioxo-1λ$^6$-thiomorpholin-4-yl)-benzoyl]-4-phenyl-piperidine-4-carboxylic acid ((S)-1-cyclohexyl-ethyl)-amide;

4-(4-fluoro-phenyl)-1-[4-(3-methyl-[1,2,4]oxadiazol-5-yl)-benzoyl]-piperidine-4-carboxylic acid ((S)-1-cyclohexyl-ethyl)-amide;

1-[4-(1,1-dioxo-1λ$^6$-thiomorpholin-4-yl)-benzoyl]-4-(4-fluoro-phenyl)-piperidine-4-carboxylic acid ((S)-1-cyclohexyl-ethyl)-amide; and 1-(4'-fluoro-biphenyl-4-carbonyl)-4-(4-fluoro-phenyl)-piperidine-4-carboxylic acid ((S)-1-cyclohexyl-ethyl)-amide.

Additional compounds encompassed by formula I are those of formula Ic

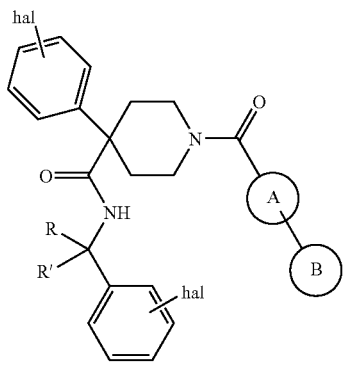

wherein
hal is halogen;
R and R' are each independently hydrogen, $(CH_2)_n$-cycloalkyl, lower alkyl, lower alkyl substituted by halogen or hydroxy, or
R and R' together with the carbon atom to which they are attached form a cycloalkyl ring;

is heteroaryl optionally substituted by lower alkyl or =O;

is aryl, heteroaryl or heterocycloalkyl, each of which is optionally substituted by lower alkyl, lower alkoxy, halogen, lower alkyl substituted by halogen, cyano, amino, C(O)-lower alkyl, C(O)NH$_2$, S(O)$_2$-lower alkyl or =O, or is cycloalkyl;
or a pharmaceutically active salt thereof, for example the following compound
1-[6-(3-methyl-[1,2,4]oxadiazol-5-yl)-pyridine-3-carbonyl]-4-phenyl-piperidine-4-carboxylic acid [(S)-1-(4-fluoro-phenyl)-ethyl]-amide.

Further compounds encompassed by formula I are those of formula Id

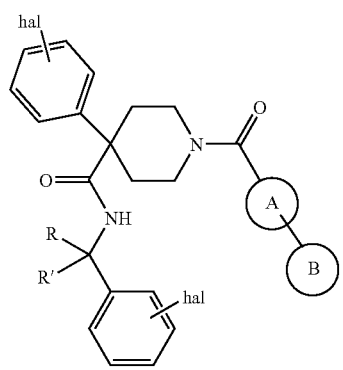

wherein
hal is halogen;
R and R' are each independently hydrogen, $(CH_2)_n$-cycloalkyl, lower alkyl, lower alkyl substituted by halogen or hydroxy, or
R and R' together with the carbon atom to which they are attached form a cycloalkyl ring;

is heterocycloalkyl optionally substituted by lower alkyl or =O;

is aryl, heteroaryl or heterocycloalkyl, each of which is optionally substituted by lower alkyl, lower alkoxy, halogen, lower alkyl substituted by halogen, cyano, amino, C(O)-lower alkyl, C(O)NH$_2$, S(O)$_2$-lower alkyl or =O, or is cycloalkyl;
or a pharmaceutically active salt thereof.
Compounds from formula Id include the following:
4-(4-fluoro-phenyl)-1-[4-(4-fluoro-phenyl)-piperazine-1-carbonyl]-piperidine-4-carboxylic acid [(S)-cyclopropyl-(3-fluoro-phenyl)-methyl]amide;
1-[4-(4-fluoro-phenyl)-piperazine-1-carbonyl]-4-phenyl-piperidine-4-carboxylic acid [(S)-1-(4-fluoro-phenyl)-ethyl]-amide;
1-[4-(4-fluoro-phenyl)-piperazine-1-carbonyl]-4-phenyl-piperidine-4-carboxylic acid ((S)-1-phenyl-ethyl)-amide;
1-[4-(3-methyl-[1,2,4]oxadiazol-5-yl)-piperidine-1-carbonyl]-4-phenyl-piperidine-4-carboxylic acid ((S)-1-phenyl-ethyl)-amide;
4-phenyl-1-(4-thiomorpholin-4-yl-piperidine-1-carbonyl)-piperidine-4-carboxylic acid ((S)-1-phenyl-ethyl)-amide;
1-[4-(4-fluoro-phenyl)-piperazine-1-carbonyl]-4-phenyl-piperidine-4-carboxylic acid ((S)-1-phenyl-propyl)-amide; and
1-[4-(4-fluoro-phenyl)-piperazine-1-carbonyl]-4-phenyl-piperidine-4-carboxylic acid ((S)-1-cyclohexyl-ethyl)-amide.

Other compounds encompassed by formula I are those of formula Ie

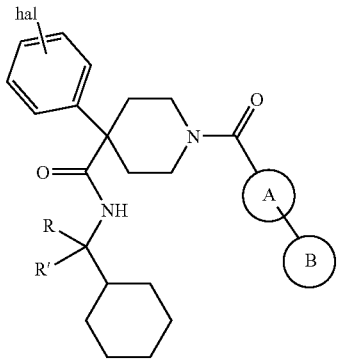

wherein
hal is halogen;
R and R' are each independently hydrogen, $(CH_2)_n$-cycloalkyl, lower alkyl, lower alkyl substituted by halogen or hydroxy, or
R and R' together with the carbon atom to which they are attached form a cycloalkyl ring;

is heterocycloalkyl optionally substituted by lower alkyl or =O;

is aryl, heteroaryl or heterocycloalkyl, each of which is optionally substituted by lower alkyl, lower alkoxy, halogen, lower alkyl substituted by halogen, cyano, amino, C(O)-lower alkyl, $C(O)NH_2$, $S(O)_2$-lower alkyl or =O, or is cycloalkyl;
or a pharmaceutically active salt thereof. An examples of such compound is
1-[4-(4-Fluoro-phenyl)-piperazine-1-carbonyl]-4-phenyl-piperidine-4-carboxylic acid ((S)-1-cyclohexyl-ethyl)-amide.

Further compounds of formula I are those, wherein R' is heteroaryl, which is optionally substituted by halogen, or is $(CH_2)_n$-cycloalkyl and n is 0, 1 or 2,
lower alkyl,
lower alkenyl or
lower alkyl substituted by halogen;
and the other definitions are as described above.
Examples of such compounds are
4-cyclohexyl-1-[4-(3-methyl-[1,2,4]oxadiazol-5-yl)-benzoyl]-piperidine-4-carboxylic acid [(S)-1-(4-fluoro-phenyl)-ethyl]-amide;
4-cyclopentyl-1-(4'-fluoro-biphenyl-4-carbonyl)-piperidine-4-carboxylic acid [(S)-1-(4-fluoro-phenyl)-ethyl]-amide;
4-cyclopentyl-1-[4-(3-methyl-[1,2,4]oxadiazol-5-yl)-benzoyl]-piperidine-4-carboxylic acid [(S)-1-(4-fluoro-phenyl)-ethyl]-amide;
4-cyclopentyl-1-[4-(5-methyl-[1,2,4]oxadiazol-3-yl)-benzoyl]-piperidine-4-carboxylic acid [(S)-1-(4-fluoro-phenyl)-ethyl]-amide;
1-(4'-fluoro-biphenyl-4-carbonyl)-4-(2-methyl-allyl)-piperidine-4-carboxylic acid [(S)-1-(4-fluoro-phenyl)-ethyl]-amide; and
5-fluoro-1'-[4-(3-methyl-[1,2,4]oxadiazol-5-yl)-benzoyl]-2', 3',5',6'-tetrahydro-1'H-[2,4']bipyridinyl-4'-carboxylic acid [(S)-1-(4-fluoro-phenyl)-ethyl]-amide.

Further compounds of formula I are those, wherein $R^2$ is —NR-aryl or NR-heteroaryl, wherein aryl and heteroaryl are each optionally substituted by halogen, lower alkyl, lower alkyl substituted by halogen or cyano, or is NR-cycloalkyl, indan-1-yl or indan-2-yl, each of which is optionally substituted by hydroxy;

The present compounds of formula I and their pharmaceutically acceptable salts can be prepared by methods, known in the art, for example by the process variant described below, which process comprises a) cleaving off the ether group of a compound of formula IV

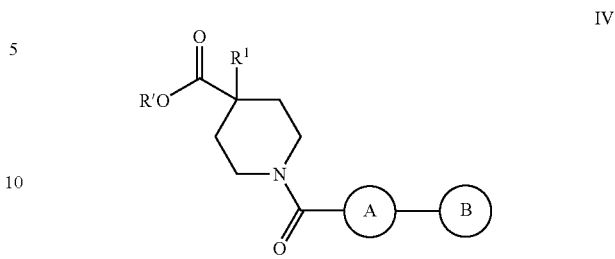

under basic-aqueous conditions (LiOH, NaOH, KOH) to access the respective acid derivatives, and then coupling with amines/hydrazines and coupling reagents (HATU, TBTU, EDCI) in the presence of a base ($NEt_3$, DIPEA) and with a suitable carbamoyl chloride, acid chloride or carboxylic acid to obtain piperidine derivatives of formula

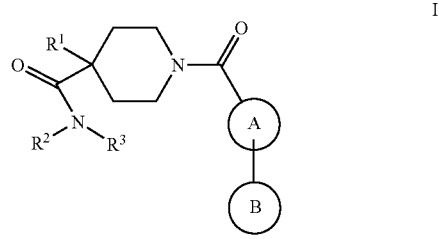

wherein the definitions are as described above
and if desired, converting the compounds obtained into pharmaceutically acceptable acid addition salts;
or
b)—coupling a compound of formula V

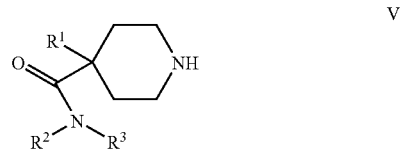

with corresponding acid chlorides/carbamoyl in the presence of a base or coupling a compound of formula V with the appropriate acid derivatives with coupling reagents (HATU, TBTU, EDCI) in the presence of a base ($NEt_3$, DIPEA) activating a compound of formula V with CDI or phosgene and subsequently coupling with the appropriate amine derivative,
wherein the definitions are as described above,
and if desired, converting the compounds obtained into pharmaceutically acceptable acid addition salts.

General Experimental Part:
The preparation of compounds of formula I and II of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary. In more detail, the compounds of formula I can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 2nd Edition, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction can also vary widely, depending on many factors, notably the reaction temperature and the nature of the reagents. However, a period of from 0.5 h to several days will usually suffice to yield the described intermediates and compounds. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

hexylamide and subsequent coupling with aryl/heteroaryl halides in the presence of $Pd_2(dba)_2$ and $Pd(tBu_3P)_2$ and the like as e.g. described by Jorgensen et al. JACS 2002, 124, 12557-12565 or Shetty et al. THL 2006, 47, 8021-8024. The introduction of R'=alkyl or $(CH_2)_n$-cycloalkyl can for example be done by deprotonation with an appropriate base (KOtBu, NaH, LDA and the like) and subsequent reaction with an alkyl/$(CH_2)_n$-cycloalkyl halide. Alternatively, an alkenyl substituent can be introduced by a Claisen-Ireland rearrangement (BMCL 2007, 17, 5720-5723) of the respective ester triggered through reaction with base and TMS-Cl. The respective product can be used in subsequent reactions as outlined in scheme 1 or alternatively hydrogenated/derivatized to the respective alkyl derivative and subsequently used as described in scheme 1.

b) The protecting group (PG) in piperidine derivatives III can be cleaved according to standard procedures depending on the nature of the protecting group. The liberated piperidine derivative can conveniently be coupled with acid chlorides/carbamoyl chlorides (commercially available or accessible through procedures described in literature) in the presence of a base to access piperidine derivatives IV. Alternatively, coupling can be done with the appropriate acid derivatives (commercially available or accessible through procedures described in literature) with coupling reagents (HATU, TBTU, EDCI and the like) in the presence of a base ($NEt_3$, DIPEA and the like).

c) The ester functionality in piperidine derivatives IV can conveniently be cleaved under basic-aqueous conditions (LiOH, NaOH, KOH and the like) to access the respective

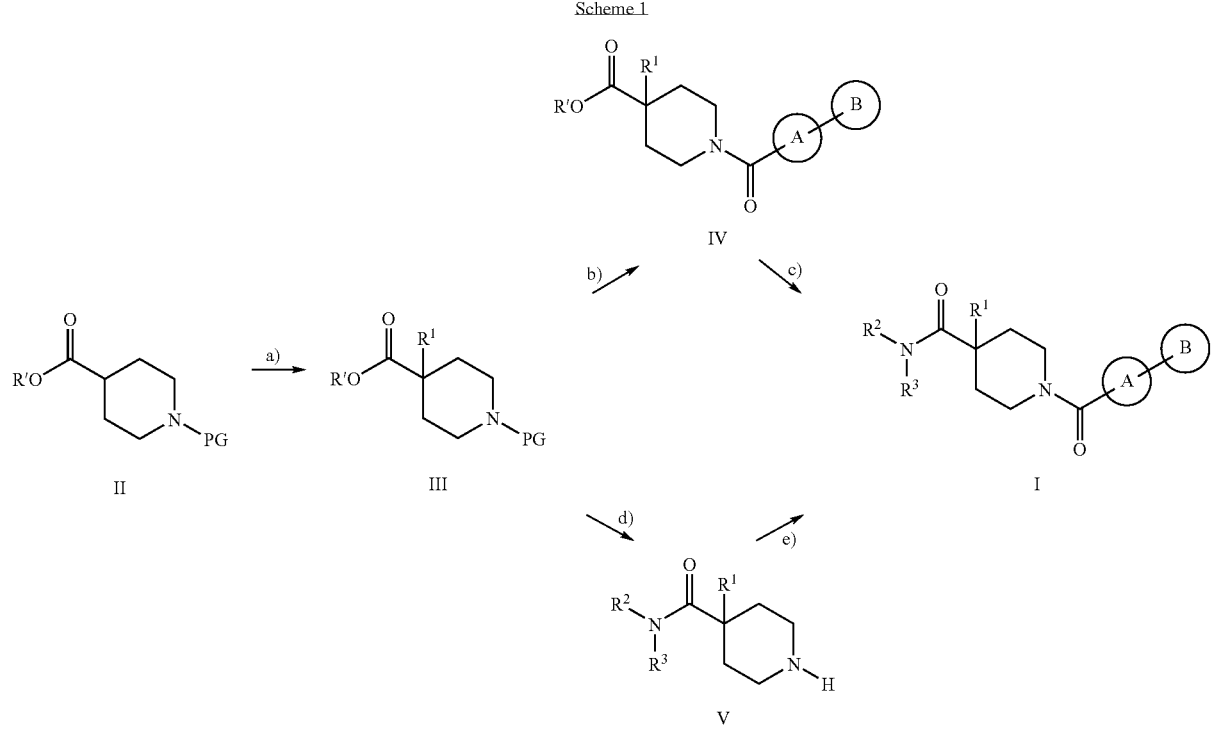

Scheme 1 a) Piperidine derivatives II are commercially available and be transferred to 4-substituted piperidine derivatives III in various ways. Introduction of R'=aryl or heteroaryl can conveniently be done by palladium catalyzed α-arylation via conversion to the respective enolates with lithium dicycloacid derivatives. The acid moiety can conveniently be coupled with amines/hydrazines with coupling reagents (HATU, TBTU, EDCI and the like) in the presence of a base ($NEt_3$, DIPEA and the like) to access piperidine derivatives I. These compounds can be final compounds, however, they can serve as starting materials for derivatisation for example at the amide/hydrazide-NH with electrophiles under basic conditions.

d) The ester functionality in piperidine derivatives III can conveniently be cleaved under basic-aqueous conditions (LiOH, NaOH, KOH and the like) to access the respective acid derivatives. The acid moiety can conveniently be coupled with amines/hydrazines with coupling reagents (HATU, TBTU, EDCI and the like) in the presence of a base (NEt$_3$, DIPEA and the like) to access the respective piperidine derivatives in which the protecting group PG can be cleaved according to standard procedures depending on the nature of the protecting group to access piperidine derivatives V.

e) Piperidine derivatives V can conveniently be coupled with acid chlorides/carbamoyl chlorides (commercially available or accessible through procedures described in literature) in the presence of a base to access piperidine derivatives I. Alternatively, coupling can be done with the appropriate acid derivatives (commercially available or accessible through procedures described in literature) with coupling reagents (HATU, TBTU, EDCI and the like) in the presence of a base (NEt$_3$, DIPEA and the like) to access piperidine derivatives I. Alternatively, piperidine derivatives V can be activated with CDI, phosgene and the like and subsequently coupled with the appropriate amine derivative (commercially available or accessible through procedures described in literature) to access piperidine derivative I. These compounds can be final compounds, however, they can serve as starting materials for derivatisation for example at the amide/hydrazide-NH with electrophiles under basic conditions.

EXPERIMENTAL PROCEDURES

Intermediate 1

4-(4-Fluoro-phenyl)-piperidine-4-carboxylic acid [(S)-1-(4-fluoro-phenyl)-ethyl]-amide; compound with trifluoro-acetic acid

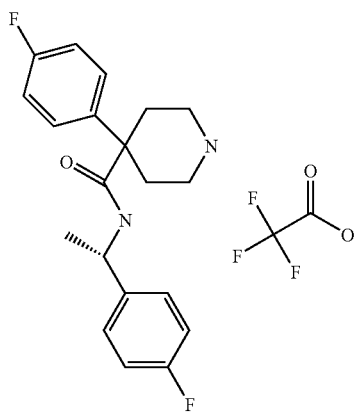

i) 4-(4-Fluoro-phenyl)-4-[(S)-1-(4-fluoro-phenyl)-ethylcarbamoyl]-piperidine-1-carboxylic acid tert-butyl ester 4-(4-Fluoro-phenyl)-piperidine-1,4-dicarboxylic acid mono-tert-butyl ester (1.0 g, 3.092 mmol) (commercially available) was suspended in dichloromethane (10 mL). EDC (949 mg, 4.948 mmol), HOBT (758 mg, 4.948 mmol) and triethylamine (1.6 mL, 11.442 mmol) were added at room temperature, followed by slow addition of a solution of (S-)-1-(4-fluorophenyl)ethylamine (0.50 mL, 3.711 mmol) in dichloromethane (5 mL). The reaction mixture was stirred at room temperature for 12 h. Water was added to the reaction mixture, the aqueous phase was extracted with ethyl acetate, the organic layers were combined and washed with aqueous ammonium chloride solution and brine, dried over Na$_2$SO$_4$ and the solvents were evaporated. The residue was purified by flash chromatography over a 70 g silica gel column with n-heptane and ethyl acetate to give 735 mg 4-(4-fluoro-phenyl)-4-[(S)-1-(4-fluoro-phenyl)-ethylcarbamoyl]-piperidine-1-carboxylic acid tert-butyl ester. MS ISN (m/e): 433.7 [(M−H)$^-$].

ii) 4-(4-Fluoro-phenyl)-piperidine-4-carboxylic acid [(S)-1-(4-fluoro-phenyl)-ethyl]-amide; compound with trifluoro-acetic acid To a solution of 4-(4-fluoro-phenyl)-4-[(S)-1-(4-fluoro-phenyl)-ethylcarbamoyl]-piperidine-1-carboxylic acid tert-butyl ester (735 mg, 1.653 mmol) in dichloromethane (8 mL) at 0° C. was added slowly trifluoroacetic acid (1.78 mL, 23.148 mmol) and stirring continued for 12 h at room temperature. The solvent was removed under reduced pressure. Toluene was added to the residue and evaporated under reduced pressure which was repeated two times. The residue was dried under high vacuum to yield 970 mg 4-(4-fluoro-phenyl)-piperidine-4-carboxylic acid [(S)-1-(4-fluoro-phenyl)-ethyl]-amide; compound with trifluoro-acetic acid. MS ISP (m/e): 345.3 [(M+H)$^+$].

In analogy to the procedure described for the synthesis of intermediate 1 further aryl-piperidine-4-carboxylic acid-amides have been synthesized from their respective starting materials as shown in table 1. Table 1 comprises intermediates 2-14. Tert.-butyloxy carbonyl protecting group cleavage can also be done with other acids like HCl yielding the respective hydrochloride salts.

TABLE 1

| Intermed. No | structure | MW calc. (parent cpd) | name | starting materials | MW found (MH+) |
|---|---|---|---|---|---|
| 1 | 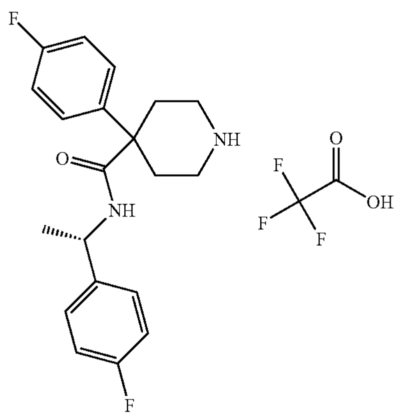 | 344.4 | 4-(4-Fluoro-phenyl)-piperidine-4-carboxylic acid [(S)-1-(4-fluoro-phenyl)-ethyl]-amide; compound with trifluoro-acetic acid | 4-(4-Fluoro-phenyl)-piperidine-1,4-dicarboxylic acid mono-tert-butyl ester and (S-)-1-(4-fluorophenyl)ethylamine (all commercially available) | 345.3 |
| 2 | 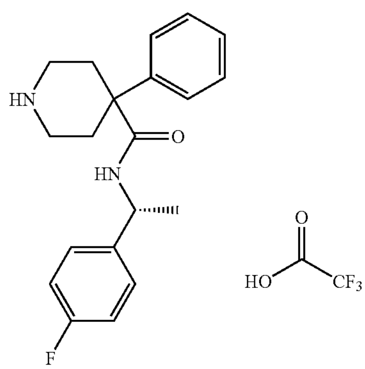 | 326.18 | 4-Phenyl-piperidine-4-carboxylic acid [(S)-1-(4-fluoro-phenyl)-ethyl]-amide; compound with trifluoro-acetic acid | 4-Phenyl-piperidine-1,4-dicarboxylic acid mono-tert-butyl ester and (S)-1-(4-fluorophenyl)ethylamine (all commercially available) | 327.2 |
| 3 | 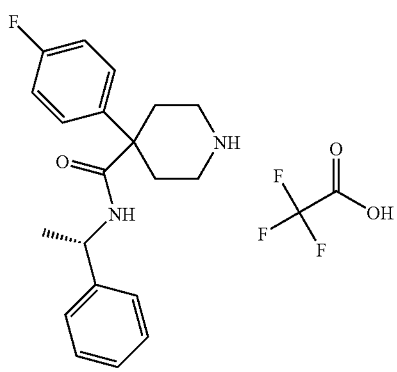 | 326.18 | 4-(4-Fluoro-phenyl)-piperidine-4-carboxylic acid ((S)-1-phenyl-ethyl)-amide; compound with trifluoro-acetic acid | 4-(4-Fluoro-phenyl)-piperidine-1,4-dicarboxylic acid mono-tert-butyl ester and (S)-1-phenyl-ethylamine (all commercially available) | 327.3 |
| 4 | 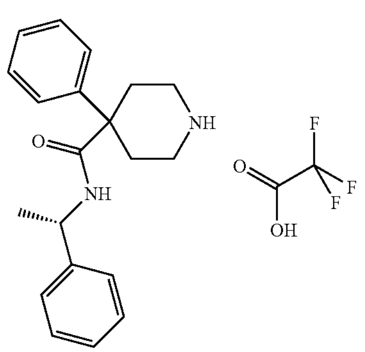 | 308.19 | 4-Phenyl-piperidine-4-carboxylic acid ((S)-1-phenyl-ethyl)-amide; compound with trifluoro-acetic acid | 4-Phenyl-piperidine-1,4-dicarboxylic acid mono-tert-butyl ester and (S)-1-phenyl-ethylamine (all commercially available) | 309.3 |

TABLE 1-continued

| Intermed. No | structure | MW calc. (parent cpd) | name | starting materials | MW found (MH+) |
|---|---|---|---|---|---|
| 5 | 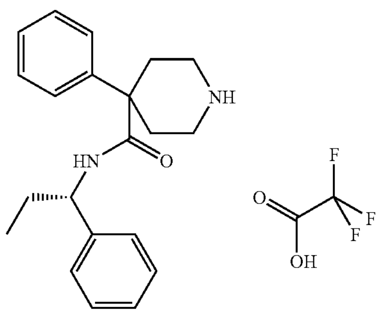 | 322.2 | 4-Phenyl-piperidine-4-carboxylic acid ((S)-1-phenyl-propyl)-amide; compound with trifluoro-acetic acid | 4-Phenyl-piperidine-1,4-dicarboxylic acid mono-tert-butyl ester and (S)-1-phenyl-propylamine (all commercially available) | 323.4 |
| 6 | 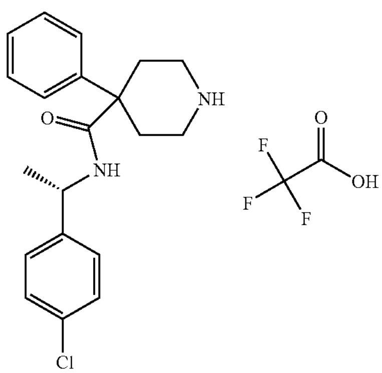 | 342.15 | 4-Phenyl-piperidine-4-carboxylic acid [(S)-1-(4-chloro-phenyl)-ethyl]-amide; compound with trifluoro-acetic acid | 4-Phenyl-piperidine-1,4-dicarboxylic acid mono-tert-butyl ester and (S)-1-(4-chloro-phenyl) ethylamine (all commercially available) | 343.2 |
| 7 | 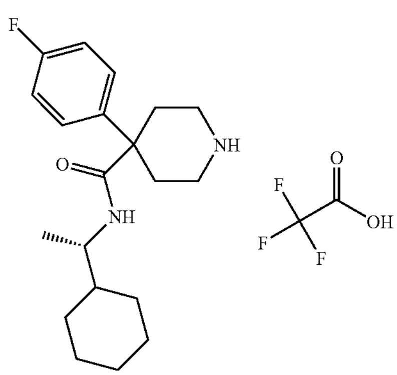 | 332.23 | 4-(4-Fluoro-phenyl)-piperidine-4-carboxylic acid ((S)-1-cyclohexyl-ethyl)-amide trifluoro-acetic acid | 4-(4-Fluoro-phenyl)-piperidine-1,4-dicarboxylic acid mono-tert-butyl ester and (S)-1-cyclohexyl-ethylamine (all commercially available) | 333.4 |
| 8 | 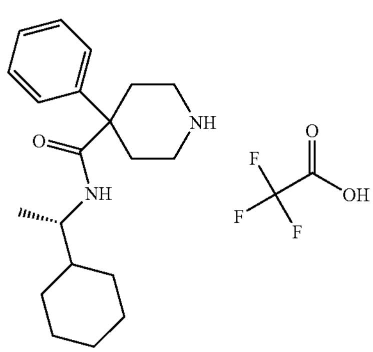 | 314.24 | 4-Phenyl-piperidine-4-carboxylic acid ((S)-1-cyclohexyl-ethyl)-amide; compound with trifluoro-acetic acid | 4-Phenyl-piperidine-1,4-dicarboxylic acid mono-tert-butyl ester and (S)-1-cyclohexyl-ethylamine (all commercially available) | 315.2 |

TABLE 1-continued

| Intermed. No | structure | MW calc. (parent cpd) | name | starting materials | MW found (MH+) |
|---|---|---|---|---|---|
| 9 | 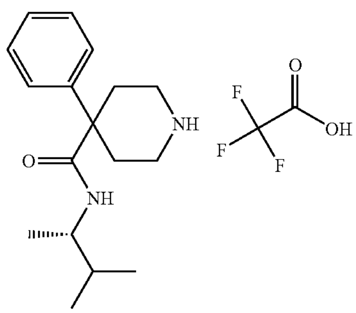 | 274.2 | 4-Phenyl-piperidine-4-carboxylic acid ((S)-1,2-dimethyl-propyl)-amide; compound with trifluoro-acetic acid | 4-Phenyl-piperidine-1,4-dicarboxylic acid mono-tert-butyl ester and (S)-1,2-dimethyl propylamine (all commercially available) | 275.2 |
| 10 | 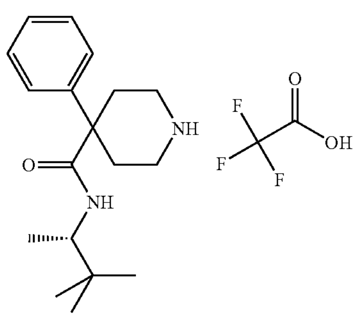 | 288.22 | 4-Phenyl-piperidine-4-carboxylic acid ((S)-1,2,2-trimethyl-propyl)-amide; compound with trifluoro-acetic acid | 4-Phenyl-piperidine-1,4-dicarboxylic acid mono-tert-butyl ester and (S)-1,2,2-trimethyl-propylamine (all commercially available) | 289.2 |
| 11 | 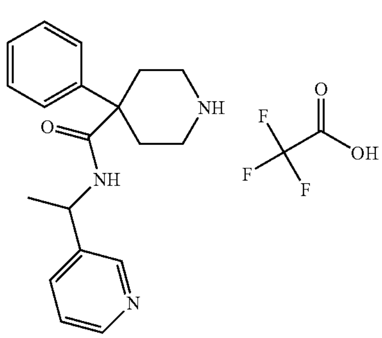 | 309.18 | rac-4-Phenyl-piperidine-4-carboxylic acid (1-pyridin-3-yl-ethyl)-amide; compound with trifluoro-acetic acid | 4-Phenyl-piperidine-1,4-dicarboxylic acid mono-tert-butyl ester and 1-pyridin-3-yl-ethylamine (all commercially available) | 310.3 |

TABLE 1-continued

| Intermed. No | structure | MW calc. (parent cpd) | name | starting materials | MW found (MH+) |
|---|---|---|---|---|---|
| 12 | 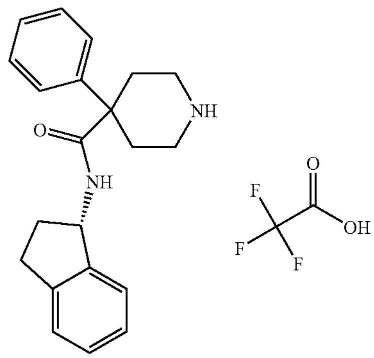 | 320.19 | 4-Phenyl-piperidine-4-carboxylic acid (S)-indan-1-ylamide; compound with trifluoro-acetic acid | 4-Phenyl-piperidine-1,4-dicarboxylic acid mono-tert-butyl ester and (S)-indan-1-ylamine (all commercially available) | 321.3 |
| 13 | 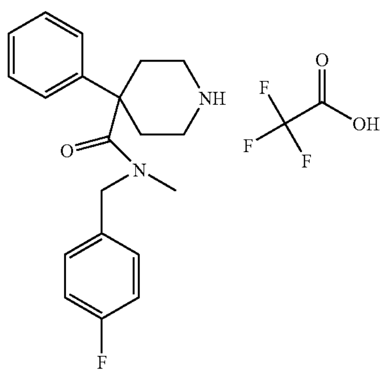 | 326.18 | 4-Phenyl-piperidine-4-carboxylic acid (4-fluoro-benzyl)-methyl-amide; compound with trifluoro-acetic acid | 4-Phenyl-piperidine-1,4-dicarboxylic acid mono-tert-butyl ester and (4-fluoro-benzyl) methyl-amine (all commercially available) | 327.3 |
| 14 | 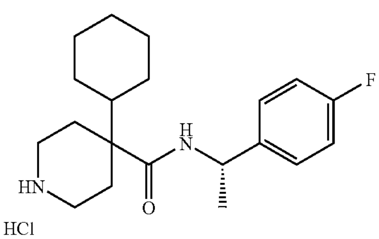 | 332.47 | 4-Cyclohexyl-piperidine-4-carboxylic acid [(S)-1-(4-fluoro-phenyl) ethyl]-amide; hydrochloride | 4-Cyclohexyl-1,4-piperidinedicarboxylic acid tert butyl ester and (S-)-1-(4-fluorophenyl)ethylamine (all commercially available) | 333.3 |

Intermediate 15

4-Cyclopentyl-piperidine-4-carboxylic acid [(S)-1-(4-fluoro-phenyl)-ethyl]-amide; hydrochloride

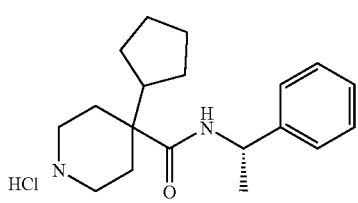

i) 4-Cyclopentyl-piperidine-1,4-dicarboxylic acid 1-tert-butyl ester 4-ethyl ester

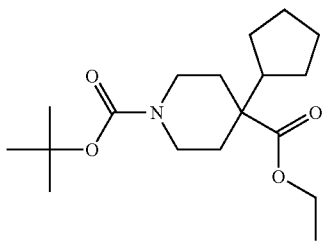

Under inert atmosphere a 500 mL four necked flask (flame dried) with a mechanical stirrer was charged with 3.29 mL diisopropylamine in 50 mL THF. The solution was cooled to −5° C./−10° C. To the colourless solution 14.57 mL BuLi in 1.6M hexane was added drop wise over 20 min. The light yellow solution was stirred for 30 min at −5° C. and then cooled to −75° C.

A solution of 5 g ethyl 1-tert-butoxycarbonylpiperidine-4-carboxylate in 50 mL THF was added at −75° C. drop wise over 50 min. The yellow solution was stirred at −75° C. for 2 h. A solution of 4.5 g cyclopentyliodide in 20 mL THF was added drop wise over 45 min. The reaction was stirred at −75° C. for 1 h. The reaction was allowed to warm to room temperature over the weekend. The reaction was cooled to 0° C., quenched with 150 mL 10% citric acid solution. The aqueous layer was separated and extracted once with 150 mL ethyl acetate. The organic layers were washed with 100 mL brine, dried over $Na_2SO_4$, filtered and concentrated under vacuum. The crude product (yellow viscous oil, 7.75 g) was purified over silica chromatography eluting with a gradient formed from heptane and TBME to yield after evaporation of the product containing fractions 5.54 g (88%) of the title compound as colourless viscous oil. MS ISP (m/e): 326.3 [(M+H)$^+$].

ii) 4-Cyclopentyl-piperidine-1,4-dicarboxylic acid mono-tert-butyl ester

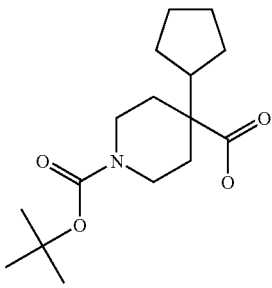

In a 250 mL round bottom flask with a magnetic stirrer, 5.4 g (16.7 mmol) 4-cyclopentyl-piperidine-1,4-dicarboxylic acid 1-tert-butyl ester 4-ethyl ester was dissolved in 40 mL EtOH. To the colourless solution 40 mL 4N NaOH was added. The orange solution was stirred under reflux for total of 6 days. The ethanol was removed and the reaction mixture was diluted with 100 mL ice water and extracted twice with 100 mL diethyl ether. The aqueous layer was acidified with 60 mL 4 N HCl to pH=2. A white precipitate formed and after addition of 200 mL ethyl acetate: THF 1:1 the white gelatinous suspension was filtered through a membrane filter. The aqueous layer from the filtrate was separated and extracted once with 100 mL ethyl acetate. The organic was layer dried with $Na_2SO_4$, filtered and concentrated under vacuum. The crude product (2.54 g, yellow viscous oil) was purified over silica chromatography eluting with a gradient formed from heptane and ethyl acetate to yield after evaporation of the product containing fractions 1.89 g (38%) of the title compound as off-white solid. MS ISP (m/e): 298.2 [(M+H)$^+$].

iii) 4-Cyclopentyl-piperidine-4-carboxylic acid [(S)-1-(4-fluoro-phenyl)-ethyl]-amide; hydrochloride In analogy to the procedure described for the synthesis of intermediate 1 the title compound was prepared from 4-cyclopentyl-piperidine-1,4-dicarboxylic acid mono-tert-butyl ester and (S-)-1-(4-fluorophenyl)ethylamine through coupling with HATU, in DMF/DIPEA followed by removal of the tert.-butyloxycarbonyl group with HCl in dioxane. MS ISP (m/e): 319.2 [(M+H)$^+$].

Intermediate 16

4-(2-Methyl-allyl)-piperidine-4-carboxylic acid [(S)-1-(4-fluoro-phenyl)-ethyl]-amide

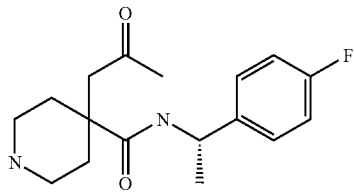

i) Piperidine-1,4-dicarboxylic acid 1-tert-butyl ester 4-(2-methyl-allyl) ester

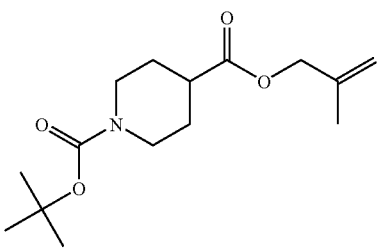

Under inert condition a 500 mL round bottom flask with a magnetic stirrer was charged with 6.87 g (30 mmol) of 1-tert.-butyloxycarbonyl-piperidine-4-carboxylic acid, 110 mg (0.09 mmol) DMAP and 11.5 g (60 mmol) 1-(3-dimethylaminopropyl)-3-ethylcarbodiimide, hydrochloride and 150 mL DCM. To the light yellow solution 3.25 g (45 mmol) 2-methyl-2-propen-1-ol was added. The reaction mixture was stirred over night at room temperature. The mixture was concentrated under vacuum, isolute-HM-N was added and evaporated to dryness. The residue was purified over silica eluting with heptane and ethyl acetate to yield after evaporation of the product containing fractions 7.3 g (86%) of the title compound as colourless oil. MS ISP (m/e): 306.2 [(M+H)+].

ii) 4-(2-Methyl-allyl)-piperidine-1,4-dicarboxylic acid mono-tert-butyl ester

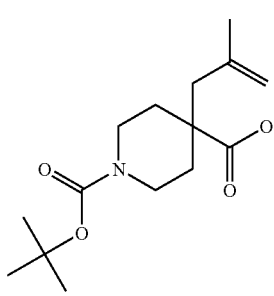

A flame dried 500 mL four-necked round bottom flask with a mechanic stirrer was charged under inert condition with 4 mL (28 mmol) of diisopropylamine and 65 mL THF. At −5° C. 17.7 mL (28 mmol) 1.6 N butyllithium/hexane-solution was added drop wise over a period of 20 min. The light yellow solution was stirred for 30 min at −5°/−10° C. and afterwards cooled to −75° C. A solution of 7.3 g (26 mmol) piperidine-1,4-dicarboxylic acid 1-tert-butyl ester 4-(2-methyl-allyl) ester in 25 mL THF was added drop wise during 20 min and stirred for 45 min at −75° C. Addition of a solution of 3.6 mL (28 mmol) TMSCl in 10 mL THF during 15 min was followed by stirring for 30 min at −75° C. and warming up over 45 minutes to ambient temperature. The colorless solution was heated for 67 h at reflux. The light yellow reaction solution was cooled to 5° C., dropwise 50 mL 2 N aq. HCl was added, stirred for 10 min and 100 mL water and 100 mL ethyl acetate was added. The aqueous layer was separated and extracted once with 150 mL ethyl acetate. The organic layers were washed twice with 200 mL brine, dried over Na₂SO₄, filtered and concentrated under vacuum. The residue was purified on silica eluting with a gradient formed from heptane, ethyl acetate and acetic acid to yield after evaporation of the product containing fractions 4.2 g (57%) of the title compound as off-white solid. MS ISP (m/e): 282.5 [(M+H)+].

iii) 4-(2-Methyl-allyl)-piperidine-4-carboxylic acid [(S)-1-(4-fluoro-phenyl)-ethyl]-amide In analogy to the procedure described for the synthesis of intermediate 1 the title compound was prepared from 4-(2-Methyl-allyl)-piperidine-1,4-dicarboxylic acid mono-tert-butyl ester and (S-)-1-(4-fluorophenyl)ethylamine through coupling with HATU, in DMF/DIPEA followed by removal of the tert.-butyl oxycarbonyl group with TFA in DCM and liberation of the free amine with Na₂CO₃. aq. MS ISP (m/e): 305.2 [(M+H)+].

Intermediate 17

6-(3-methyl-[1,2,4]oxadiazol-5-yl)-nicotinic acid

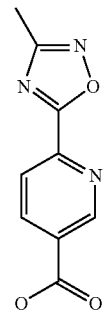

i) 6-Chlorocarbonyl-nicotinic acid methyl ester

A mixture of pyridine-2,5-dicarboxylic acid 5-methyl ester (150 mg, 0.828 mmol) and thionyl chloride (1 mL) was heated at 80° C. for 5 h. The thionyl chloride was evaporated under reduced pressure, the residue was dried in high vacuum and used crude for the next reaction.

ii) O-(5-Methoxycarbonyl-pyridine-2-carbonyl)acetamide oxime

To a solution of 6-chlorocarbonyl-nicotinic acid methyl ester in THF (5 mL) were added acetamide oxime (75 mg, 1.017 mmol) and triethylamine (0.211 mL, 1.526 mmol). After 12 h at room temperature water was added. The aqueous phase was extracted with ethyl acetate, the organic layers were combined, dried over Na₂SO₄, and the solvents were evaporated. The residue was dried in high vacuum and used crude for the next reaction. MS ISP (m/e): 220.2 [(M+H)+].

iii) 6-(3-Methyl-[1,2,4]oxadiazol-5-yl)-nicotinic acid methyl ester

To a solution of O-(5-methoxycarbonyl-pyridine-2-carbonyl)acetamide oxime (113 mg, 0.476 mmol) in dry tetrahydrofuran (1 mL) was added a solution of tetrabutyl ammonium fluoride in tetrahydrofuran (1M, 0.274 mL, 0.953 mmol). After 12 h at room temperature brine was added. The aqueous phase was extracted with ethyl acetate, the organic layers were combined, dried over Na₂SO₄, and the solvents were evaporated and the residue was subjected to flash chromatography with n-heptane and ethyl acetate over a 20 g silica gel column to give 60 mg 6-(3-methyl-[1,2,4]oxadiazol-5-yl)-nicotinic acid methyl ester.

iv) 6-(3-Methyl-[1,2,4]oxadiazol-5-yl)-nicotinic acid

To a solution of 6-(3-methyl-[1,2,4]oxadiazol-5-yl)-nicotinic acid methyl ester (54 mg, 0.246 mmol) in methanol (5 mL) was added an aqueous solution of KOH (3M, 0.49 mL, 1.48 mmol) and the mixture was heated at 70° C. for 12 h. The reaction mixture was neutralized under ice cooling with 2M HCl solution. The solvents were evaporated under reduced pressure, co-evaporated three times with toluene and dried under high vacuum. The acid was used crude for the next reaction. MS ISN (m/e): 204.2 [(M−H)−].

Intermediate 18

6-(1,1-Dioxo-1λ$^6$-thiomorpholin-4-yl)-nicotinic acid

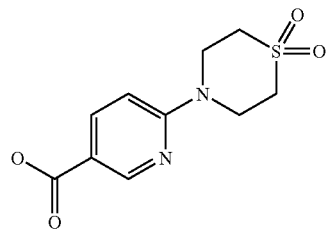

i) 6-(1,1-Dioxo-1λ$^6$-thiomorpholin-4-yl)-nicotinic acid methyl ester

A solution of methyl 6-chloronicotinate (3.43 g, 20 mmol), thiomorpholine 1,1-dioxide (2.70 g, 20 mmol) and sodium carbonate (2.54 g, 24 mmol) in NMP (40 mL) was heated to 90° C. for 3 days. The reaction mixture was poured into water and the white solid formed was filtered off to give 2.22 g 6-(1,1-dioxo-1λ$^6$-thiomorpholin-4-yl)-nicotinic acid methyl ester. The aqueous phase was extracted with ethyl acetate, the combined organic phases were dried over Na$_2$SO$_4$, filtered and the solvents were evaporated. The residue was triturated with diethyl ether and the solid filtered off to yield another 1.18 g 6-(1,1-dioxo-1λ$^6$-thiomorpholin-4-yl)-nicotinic acid methyl ester.

ii) 6-(1,1-Dioxo-1λ$^6$-thiomorpholin-4-yl)-nicotinic acid

To a solution of 6-(1,1-dioxo-1λ$^6$-thiomorpholin-4-yl)-nicotinic acid methyl ester (156 mg, 0.577 mmol) in methanol (10 mL) was added aqueous KOH (3M, 1.2 mL, 3.463 mmol) and the mixture was heated at 70° C. for 12 h. The methanol was evaporated, water was added and the mixture acidified to pH=6 with 2N HCl. The water was evaporated and the residue dried in high vacuum to give 6-(1,1-dioxo-1λ$^6$-thiomorpholin-4-yl)-nicotinic acid which was used crude for the next step.

Example 1

1-[4-(1,1-Dioxo-1λ$^6$-thiomorpholin-4-yl)-benzoyl]-4-(4-fluoro-phenyl)-piperidine-4-carboxylic acid [(S)-1-(4-fluoro-phenyl)-ethyl]-amide

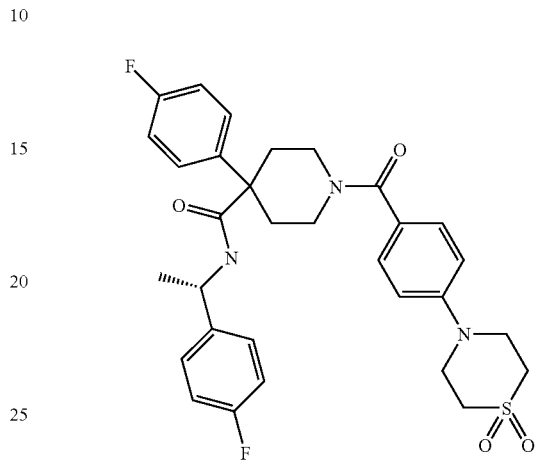

To a solution of 4-(1,1-dioxo-1λ$^6$-4-thiazinan-4-yl)benzenecarboxylic acid (26 mg, 0.102 mmol), EDC (31 mg, 0.163 mmol), HOBT (25 mg, 0.163 mmol) and triethylamine (53 µl., 0.378 mmol)) in dichloromethane (2 mL) at room temperature was added slowly a solution of 4-(4-fluoro-phenyl)-piperidine-4-carboxylic acid [(S)-1-(4-fluoro-phenyl)-ethyl]-amide; TFA salt (47 mg, 0.102 mmol) in DCM (1 mL). The reaction mixture was stirred at room temperature for 12 h. The reaction mixture was subjected to flash chromatography with dichloromethane and methanol over a 10 g silica gel column to yield 51 mg 1-[4-(1,1-dioxo-1λ$^6$-thiomorpholin-4-yl)-benzoyl]-4-(4-fluoro-phenyl)-piperidine-4-carboxylic acid [(S)-1-(4-fluoro-phenyl)-ethyl]-amide. MS ISP (m/e): 582.3 (100) [(M+H)+].

In analogy to the procedure described for the synthesis of 1-[4-(1,1-Dioxo-1λ6-thiomorpholin-4-yl)-benzoyl]-4-(4-fluoro-phenyl)-piperidine-4-carboxylic acid [(S)-1-(4-fluoro-phenyl)-ethyl]-amide (example 1) further piperidine derivatives have been synthesized from their respective starting materials as mentioned in table 2. Table 2 comprises example 2-example 113.

TABLE 2

| No | structure | MW | Systematic Name | starting materials | MW (MH+) |
|---|---|---|---|---|---|
| 2 | 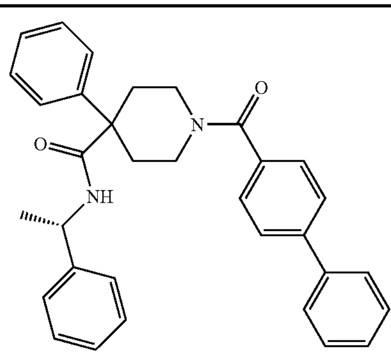 | 488.628 | 1-(Biphenyl-4-carbonyl)-4-phenyl-piperidine-4-carboxylic acid ((S)-1-phenyl-ethyl)-amide | 4-Phenyl-pipendine-4-carboxylic acid ((S)-1-phenyl-ethyl)-amide; compound with trifluoro-acetic acid (intermediate 4) and biphenyl-4-carboxylic acid (commercially available) | 489.3 |

TABLE 2-continued

| No | structure | MW | Systematic Name | starting materials | MW (MH+) |
|---|---|---|---|---|---|
| 3 | 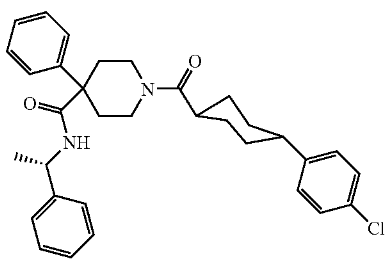 | 529.12 | 1-[4-(4-Chloro phenyl) cyclohexane carbonyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(4-chloro-phenyl)-cyclohexanecarboxylic acid (commercially available) | 529.2 |
| 4 | 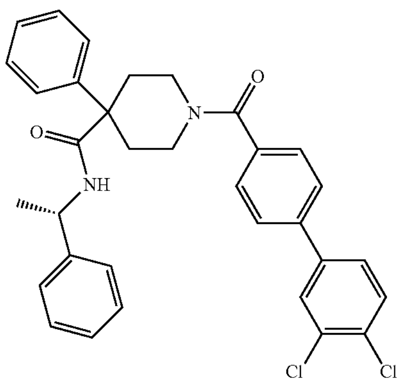 | 557.518 | 1-(3',4'-Dichloro-biphenyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 3',4'-dichloro-biphenyl-4-carboxylic acid (commercially available) | 557.1 |
| 5 | 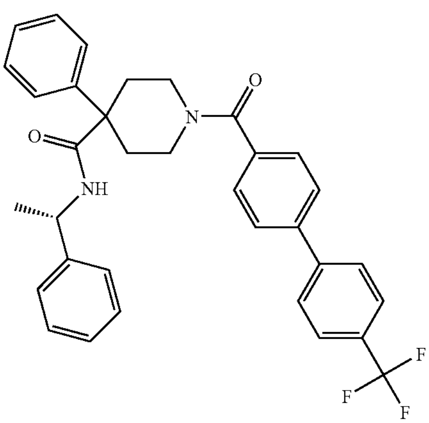 | 556.625 | 4-Phenyl-1-(4'-trifluoromethyl-biphenyl-4-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4'-trifluoromethyl-biphenyl-4-carboxylic acid (commercially available) | 557.2 |
| 6 | 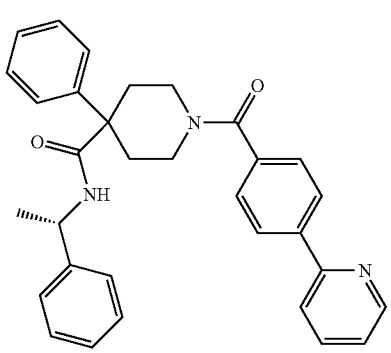 | 489.616 | 4-Phenyl-1-(4-pyridin-2-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-pyridin-2-yl-benzoic acid (commercially available) | 490.3 |

TABLE 2-continued

| No | structure | MW | Systematic Name | starting materials | MW (MH+) |
|---|---|---|---|---|---|
| 7 | 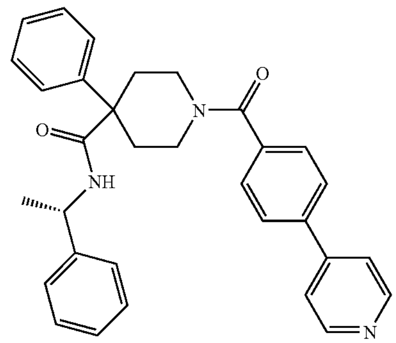 | 489.616 | 4-Phenyl-1-(4-pyridin-4-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-pyridin-4-yl-benzoic acid (commercially available) | 490.2 |
| 8 | 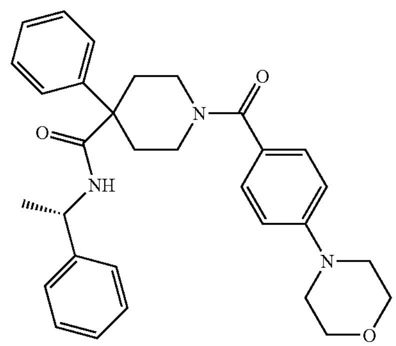 | 497.635 | 1-(4-Morpholin-4-yl-benzoyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-morpholin-4-yl-benzoic acid (commercially available) | 498.4 |
| 9 | 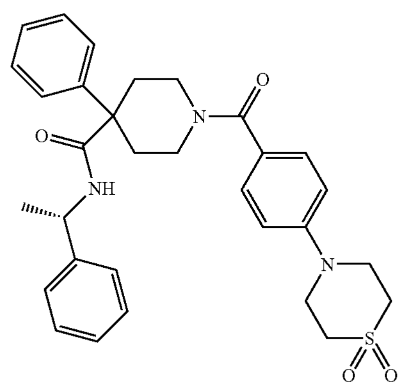 | 545.7 | 1-[4-(1,1-Dioxo-1λ6-thiomorpholin-4-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(1,1-dioxo-1λ6-thiomorpholin-4-yl)-benzoic acid (commercially available) | 546.2 |
| 10 | 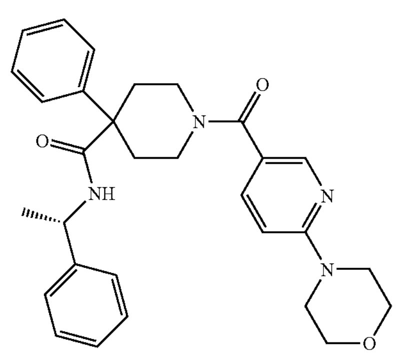 | 498.624 | 1-(6-Morpholin-4-yl-pyridine-3-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 6-morpholin-4-yl-nicotinic acid (commercially available) | 499.4 |

TABLE 2-continued

| No | structure | MW | Systematic Name | starting materials | MW (MH+) |
|---|---|---|---|---|---|
| 11 | 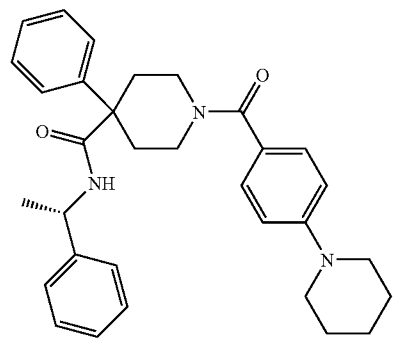 | 495.663 | 4-Phenyl-1-(4-piperidin-1-yl-benzoyl)-piperidine-4-carboxylic acid ((S)-1-phenyl-ethyl)-amide | 4-Phenyl-piperidine-4-carboxylic acid ((S)-l-phenyl-ethyl)-amide; compound with trifluoro-acetic acid (intermediate 4) and 4-piperidin-1-yl-benzoic acid (commercially available) | 496.4 |
| 12 | 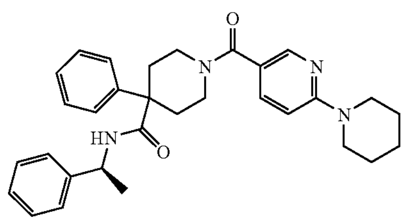 | 496.65 | 4-Phenyl-1-(3,4,5,6-tetrahydro-2H-[1,2']bipyridinyl-5'-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 3,4,5,6-tetrahydro-2H-[1,2']bipyridinyl-5'-carboxylic acid (commercially available) | 497.4 |
| 13 | 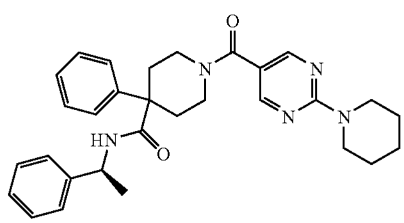 | 497.64 | 4-Phenyl-1-(2-piperidin-1-yl-pyrimidine-5-carbonyl)-piperidine-4-carboxylic acid ((S)-l-phenyl-ethyl)-amide | 4-Phenyl-piperidine-4-carboxylic acid ((S)-1-phenyl-ethyl)-amide; compound with trifluoro-acetic acid (intermediate 4) and 2-piperidin-l-yl-pyrimidine-5-carboxylic acid (commercially available) | 498.4 |
| 14 | 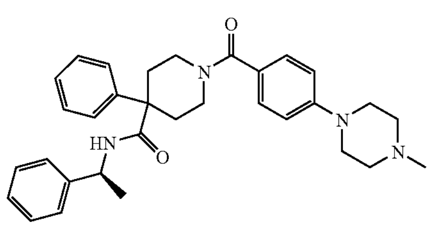 | 510.68 | 1-[4-(4-Methyl-piperazin-1-yl)-benzoyl]-4-phenyl-piperidine-4-carboxylic acid ((S)-l-phenyl-ethyl)-amide | 4-Phenyl-piperidine-4-carboxylic acid ((S)-1-phenyl-ethyl)-amide; compound with trifluoro-acetic acid (intermediate 4) and 4-(4-methyl-piperazin-1-yl)-benzoic acid (commercially available) | 511.4 |
| 15 | 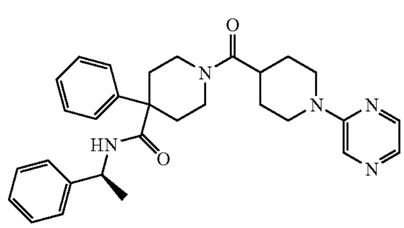 | 497.64 | 4-Phenyl-1-(1-pyrazin-2-yl-piperidine-4-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 1-pyrazin-2-yl-piperidine-4-carboxylic acid (commercially available) | 498.3 |

TABLE 2-continued

| No | structure | MW | Systematic Name | starting materials | MW (MH+) |
|---|---|---|---|---|---|
| 16 | 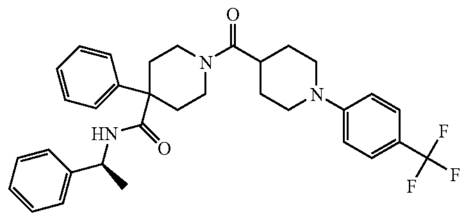 | 563.66 | 4-Phenyl-1-[1-(4-trifluoromethyl-phenyl)-piperidine-4-carbonyl]-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 1-(4-trifluoromethyl-phenyl)-piperidine-4-carboxylic acid (commercially available) | 564.4 |
| 17 | 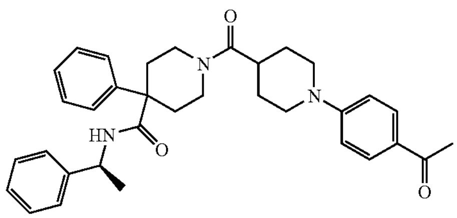 | 537.7 | 1-[1-(4-Acetyl-phenyl)-piperidine-4-carbonyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 1-(4-acetyl-phenyl)-piperidine-4-carboxylic acid (commercially available) | 538.4 |
| 18 | 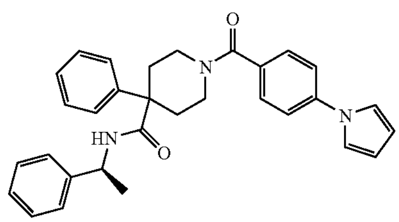 | 477.61 | 4-Phenyl-1-(4-pyrrol-1-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-pyrrol-1-yl-benzoic acid (commercially available) | 478.3 |
| 19 | 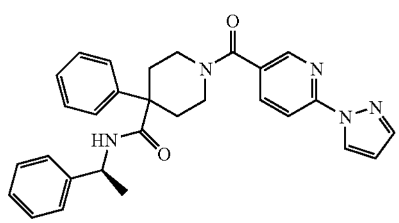 | 479.58 | 4-Phenyl-1-(6-pyrazol-1-yl-pyridine-3-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 6-pyrazol-1-yl-nicotinic acid (commercially available) | 480.3 |
| 20 | 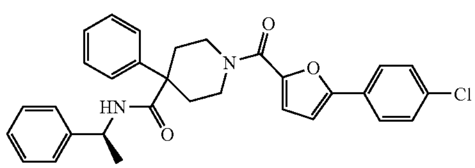 | 513.04 | 1-[5-(4-Chloro-phenyl)-furan-2-carbonyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 5-(4-chloro-phenyl)-furan-2-carboxylic acid (commercially available) | 513.4 |
| 21 | 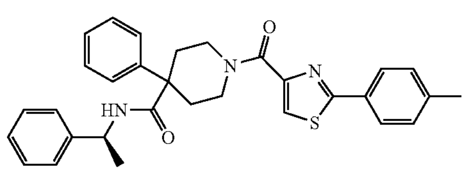 | 509.67 | 4-Phenyl-1-(2-p-tolyl-thiazole-4-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 2-p-tolyl-thiazole-4-carboxylic acid (commercially available) | 510.3 |

TABLE 2-continued

| No | structure | MW | Systematic Name | starting materials | MW (MH+) |
|---|---|---|---|---|---|
| 22 | 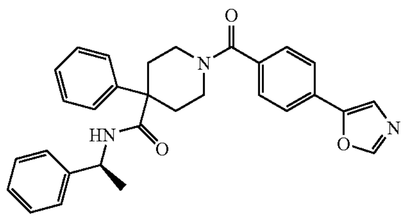 | 479.58 | 1-(4-Oxazol-5-yl-benzoyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-oxazol-5-yl-benzoic acid (commercially available) | 480.3 |
| 23 | 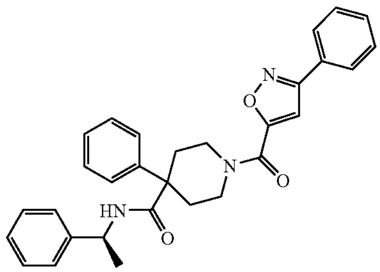 | 479.58 | 4-Phenyl-1-(3-phenyl-isoxazole-5-carbonyl)-piperidine-4-carboxylic acid ((S)-1-phenyl-ethyl)-amide | 4-Phenyl-pipendine-4-carboxylic acid ((S)-1-phenyl-ethyl)-amide; compound with trifluoro-acetic acid (intermediate 4) and 3-phenyl-isoxazole-5-carboxylic acid (commercially available) | 480.3 |
| 24 | 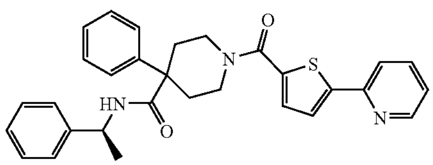 | 495.64 | 4-Phenyl-1-(5-pyridin-2-yl-thiophene-2-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-aceticacid (intermediate 4) and 5-pyridin-2-yl-thiophene-2-carboxylic acid (commercially available) | 496.4 |
| 25 | 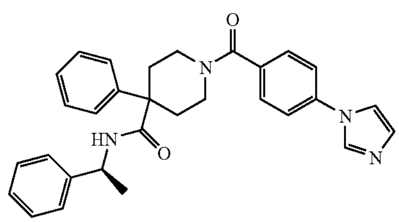 | 478.6 | 1-(4-Imidazol-1-yl-benzoyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-imidazol-1-yl-benzoic acid (commercially available) | 479.3 |
| 26 | 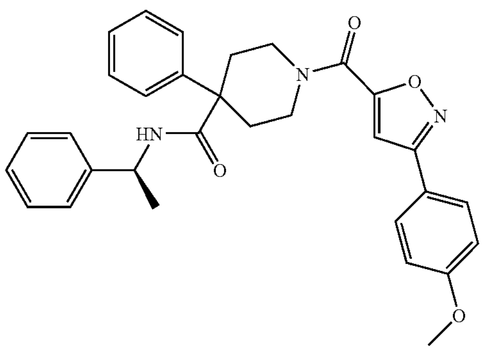 | 509.61 | 1-[3-(4-Methoxy-phenyl)*isoxazole-5-carbonyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 3-(4-methoxy-phenyl)-isoxazole-5-carboxylic acid (commercially available) | 510.4 |
| 27 | 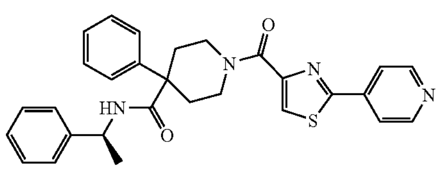 | 496.63 | 4-Phenyl-1-(2-pyridin-4-yl-thiazole-4-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 2-pyridin-4-yl-thiazole-4-carboxylic acid (commercially available) | 497.3 |

TABLE 2-continued

| No | structure | MW | Systematic Name | starting materials | MW (MH+) |
|---|---|---|---|---|---|
| 28 | 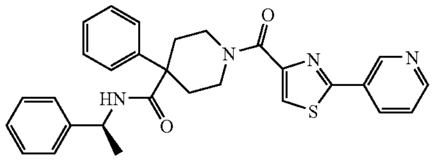 | 496.63 | 4-Phenyl-1-(2-pyridin-3-yl-thiazole-4-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 2-pyridin-3-yl-thiazole-4-carboxylic acid (commercially available) | 497.3 |
| 29 | 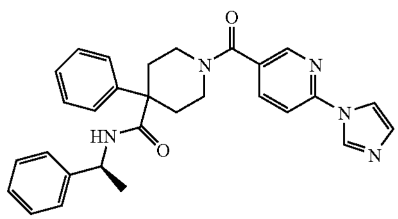 | 479.58 | 1-(6-Imidazol-1-yl-pyridine 3-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 6-imidazol-1-yl-nicotinic acid (commercially available) | 480.2 |
| 30 | 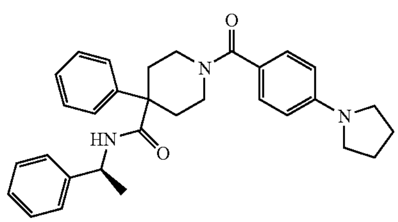 | 481.64 | 4-Phenyl-1-(4-pyrrolidin-1-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-pyrrolidin-1-yl-benzoic acid (commercially available) | 482.4 |
| 31 | 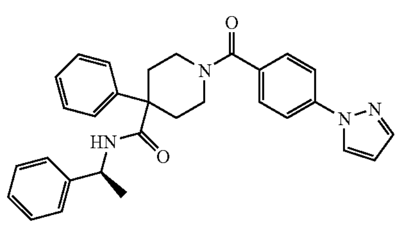 | 478.6 | 4-Phenyl-1-(4-pyrazol-1-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-imidazol-1-yl-benzoic acid (commercially available | 479.2 |
| 32 | 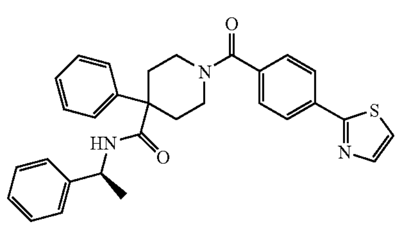 | 495.64 | 4-Phenyl-1-(4-thiazol-2-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-thiazol-2-yl-benzoic acid (commercially available) | 496.3 |
| 33 | 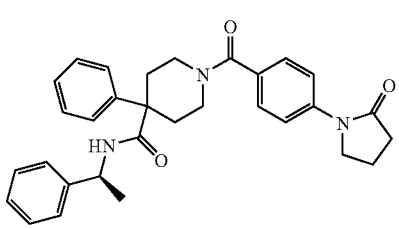 | 495.62 | 1-[4-(2-Oxo-pyrrolidin-1-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(2-oxo-pyrrolidin-1-yl)-benzoic acid (commercially available) | 496.4 |

TABLE 2-continued

| No | structure | MW | Systematic Name | starting materials | MW (MH+) |
|---|---|---|---|---|---|
| 34 | 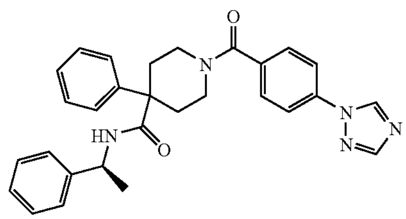 | 479.58 | 4-Phenyl-1-(4-[1,2,4]triazol-1-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-[1,2,4]triazol-1-yl-benzoic acid (commercially available) | 480.3 |
| 35 | 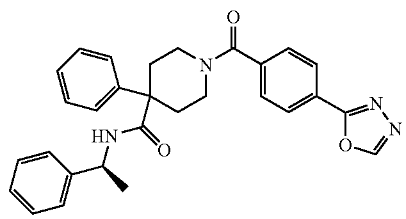 | 480.57 | 1-(4-[1,3,4]Oxadiazol-2-yl-benzoyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-[1,3,4]oxadiazol-2-yl-benzoic acid (commercially available) | 481.3 |
| 36 | 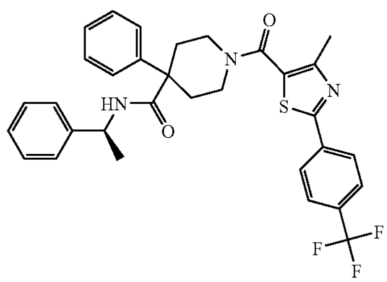 | 577.67 | 1-[4-Methyl-2-(4-trifluoromethyl-phenyl)-thiazole-5-carbonyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-methyl-2-(4-trifluoromethyl-phenyl)-thiazole-5-carboxylic acid (commercially available) | 578.2 |
| 37 | 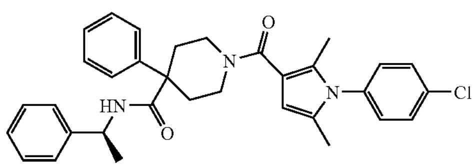 | 540.11 | 1-[1-(4-Chloro-phenyl)-2,5-dimethyl-1H-pyrrole-3-carbonyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 1-(4-chloro-phenyl)-2,5-dimethyl-1H-pyrrole-3-carboxylic acid (commercially available) | 540.2 |
| 38 | 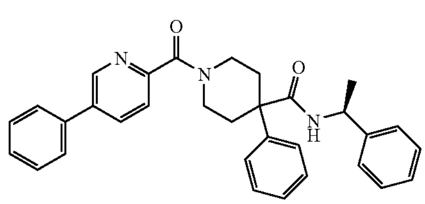 | 489.62 | 4-Phenyl-1-(5-phenyl-pyridine-2-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 5-phenyl-pyridine-2-carboxylic acid (commercially available) | 490.4 |
| 39 | 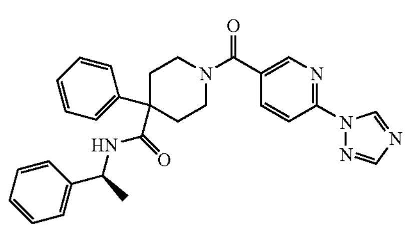 | 480.57 | 4-Phenyl-1-(6-[1,2,4]triazol-1-yl-pyridine-3-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 6-[1,2,4]triazol-1-yl nicotinic acid (commercially available) | 481.3 |

TABLE 2-continued

| No | structure | MW | Systematic Name | starting materials | MW (MH+) |
|---|---|---|---|---|---|
| 40 | 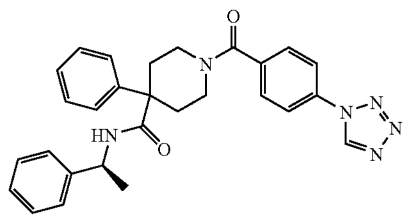 | 480.57 | 4-Phenyl-1-(4-tetrazol-1-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-tetrazol-1-yl-benzoic acid (commercially available) | 481.3 |
| 41 | 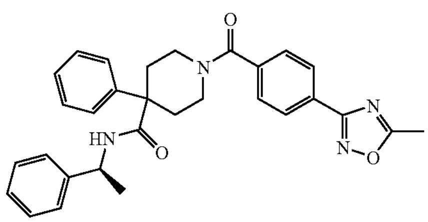 | 494.59 | 1-[4-(5-Methyl-[1,2,4]oxadiazol-3-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(5-methyl-[1,2,4]oxadiazol-3-yl)-benzoic acid (commercially available) | 495.4 |
| 42 | 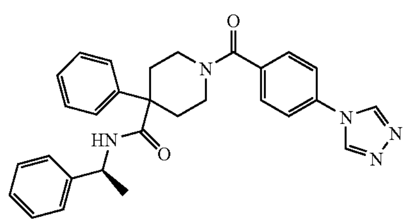 | 479.58 | 4-Phenyl-1-(4-[1,2,4]triazol-4-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-[1,2,4]triazol-4-yl-benzoic acid (commercially available) | 480.3 |
| 43 | 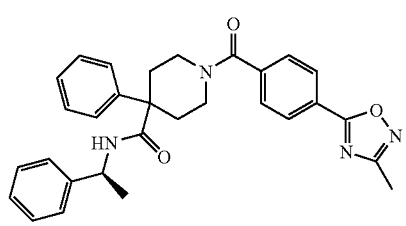 | 494.59 | 1-[4-(3-Methyl-[1,2,4]oxadiazol-5-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(3-methyl-[1,2,4]oxadiazol-5-yl)-benzoic acid (commercially available) | 495.4 |
| 44 | 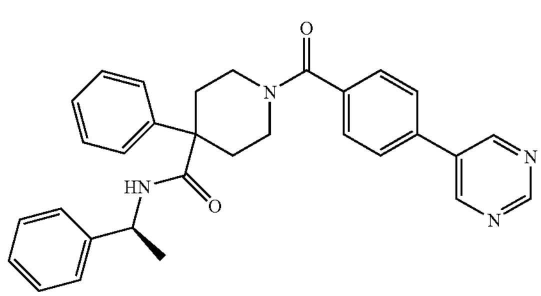 | 490.61 | 4-Phenyl-1-(4-pyrimidin-5-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-pyrimidin-5-yl-benzoic acid (commercially available) | 491.3 |

TABLE 2-continued

| No | structure | MW | Systematic Name | starting materials | MW (MH+) |
|---|---|---|---|---|---|
| 45 | 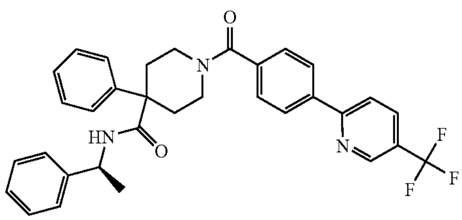 | 557.62 | 4-Phenyl-1-[4-(5-trifluoromethyl-pyridin-2-yl)benzoyl]-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(5-trifluoromethyl-pyridin-2-yl)-benzoic acid (commercially available) | 558.1 |
| 46 | 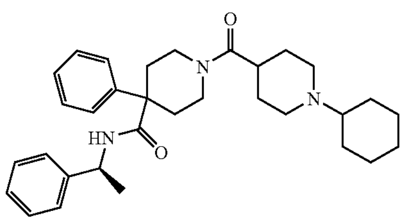 | 501.71 | 1-(1-Cyclohexyl-piperidine-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 1-cyclohexyl-piperidine 4-carboxylic acid (commercially available) | 502.4 |
| 47 | 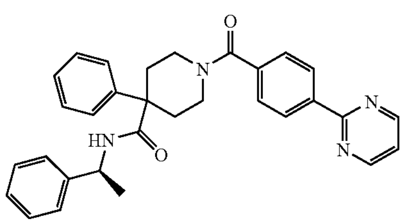 | 490.61 | 4-Phenyl-1-(4-pyrimidin-2-yl-benzoyl)-piperidine-4-carboxylic acid((S)-1-phenyl-ethyl)-amide | 4-Phenyl-piperidine-4-carboxylic acid((S)-1-phenyl-ethyl)-amide; compound with trifluoro-acetic acid (intermediate 4) and 4-pyrimidin-2-yl-benzoic acid (commercially available) | 491.2 |
| 48 | 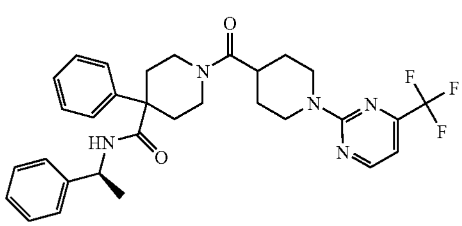 | 565.64 | 4-Phenyl-1-[1-(4-trifluoromethyl-pyrimidin-2-yl)-piperidine-4-carbonyl]-piperidine-4-carboxylic acid ((S)-1-phenyl-ethyl) amide | 4-Phenyl-piperidine-4-carboxylic acid ((S)-1-phenyl-ethyl)-amide; compound with trifluoro-acetic acid (intermediate 4) and 1-(4-trifluoromethyl-pyrimidin-2-yl)-piperidine-4-carboxylic acid (commercially available) | 566.3 |
| 49 | 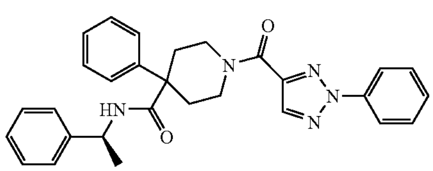 | 479.58 | 4-Phenyl-1-(2-phenyl-2H-[1,2,3]triazole-4-carbonyl)-piperidine-4-carboxylic acid ((S)-1-phenyl-ethyl)-amide | 4-Phenyl-pipendine-4-carboxylic acid ((S)-1-phenyl-ethyl)-amide; compound with trifluoro-acetic acid (intermediate 4) and 2-phenyl-2H-[1,2,3]triazole-4-carboxylic acid (commercially available) | 480.3 |

TABLE 2-continued

| No | structure | MW | Systematic Name | starting materials | MW (MH+) |
|---|---|---|---|---|---|
| 50 | 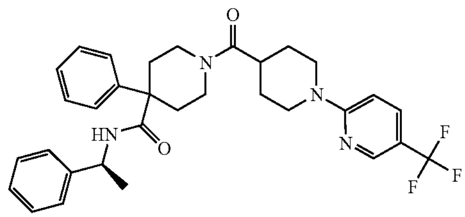 | 564.65 | 4-Phenyl-1-(5'-trifluoromethyl-3,4,5,6-tetrahydro-2H-[1,2']bipyridinyl-4-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 5'-trifluoromethyl-3,4,5,6-tetrahydro-2H-[1,2']bipyridinyl-4-carboxylic acid (commercially available) | 565.3 |
| 51 | 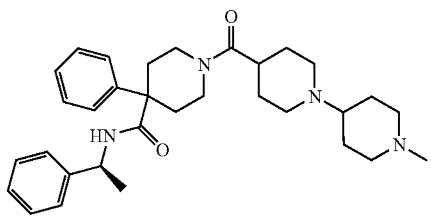 | 516.73 | 1-(1'-Methyl-[1,4']bipiperidinyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 1'-methyl-[1,4']bipiperidinyl-4-carboxylic acid (commercially available) | 517.4 |
| 52 | 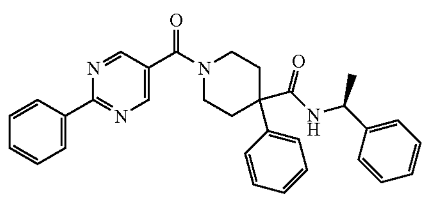 | 490.61 | 4-Phenyl-1-(2-phenyl-pyrimidine-5-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 2-phenyl-pyrimidine-5-carboxylic acid (commercially available) | 491.2 |
| 53 | 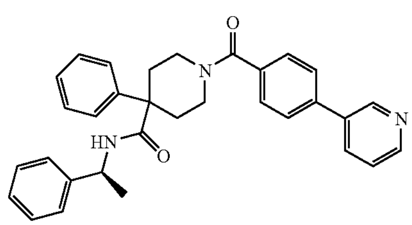 | 489.62 | 4-Phenyl-1-(4-pyridin-3-yl-benzoyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-pyridin-3-yl-benzoic acid (commercially available) | 490.3 |
| 54 | 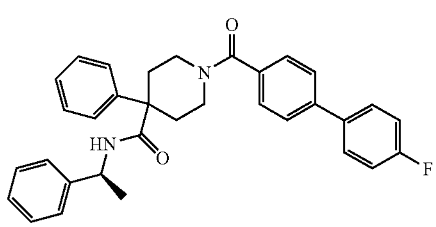 | 506.62 | 1-(4'-Fluoro-biphenyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4'-fluoro-biphenyl-4-carboxylic acid (commercially available) | 507.3 |
| 55 | 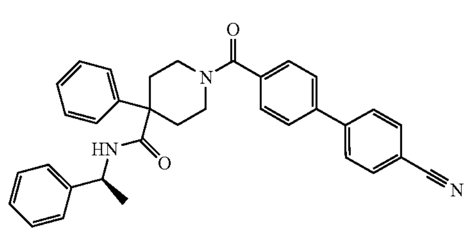 | 513.64 | 1-(4'-Cyano-biphenyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with (intermediate 4) and 4'-trifluoro-acetic acid cyano-biphenyl-4-carboxylic acid (commercially available) | 514.3 |

TABLE 2-continued

| No | structure | MW | Systematic Name | starting materials | MW (MH+) |
|---|---|---|---|---|---|
| 56 | 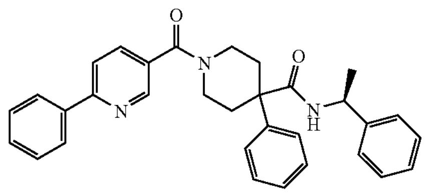 | 489.62 | 1-(4'-Cyano-biphenyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 6-phenyl-nicotinic acid (commercially available) | 490.3 |
| 57 | 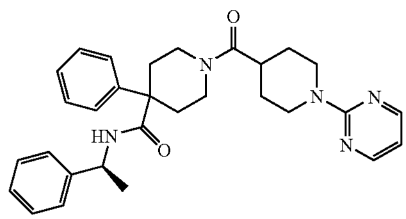 | 497.64 | 4-Phenyl-1-(1-pyrimidin-2-yl-piperidine-4-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 1-pyrimidin-2-yl-piperidine-4-carboxylic acid (commercially available) | 498.4 |
| 58 | 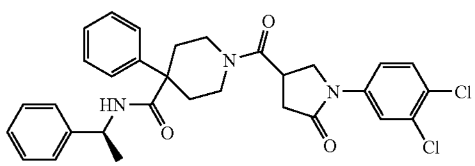 | 564.51 | 1-[1-(3,4-Dichloro-phenyl)-5-oxo-pyrrolidine-3-carbonyl]-4-phenyl-piperidine-4-carboxylic acid ((S)-1-phenyl ethyl) amide | 4-Phenyl-piperidine-4-carboxylic acid ((S)-1-phenyl-ethyl)-amide; compound with trifluoro-acetic acid (intermediate 4) and 1-(3,4-dichloro-phenyl)-2-oxo-pyrrolidine-3-carboxylic acid (commercially available) | 564.3 |
| 59 | 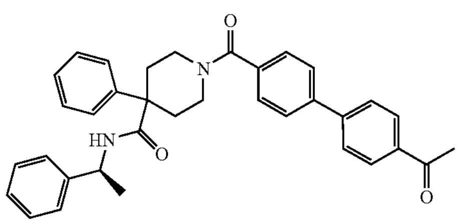 | 530.67 | 1-(4'-Acetyl-biphenyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4'-acetyl-biphenyl-4-carboxylic acid (commercially available) | 531.2 |
| 60 | 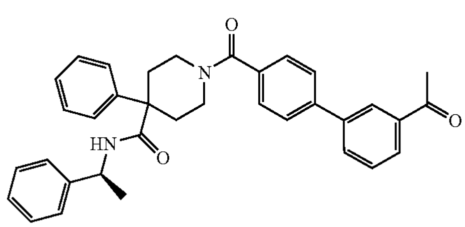 | 530.67 | 1-(3'-Acetyl-biphenyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 3'-acetyl-biphenyl-4-carboxylic acid (commercially available) | 531.2 |
| 61 | 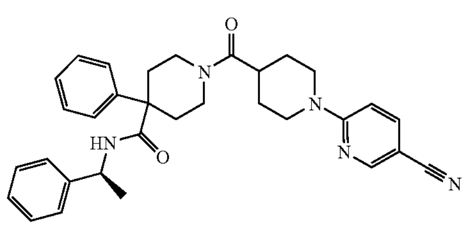 | 521.66 | 1-(5'-Cyano-3,4,5,6-tetrahydro-2H-[1,2']bipyridinyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 5'-cyano-3,4,5,6-tetrahydro-2H-[1,2']bipyridinyl-4-carboxylic acid (commercially available) | 522.4 |

TABLE 2-continued

| No | structure | MW | Systematic Name | starting materials | MW (MH+) |
|---|---|---|---|---|---|
| 62 | 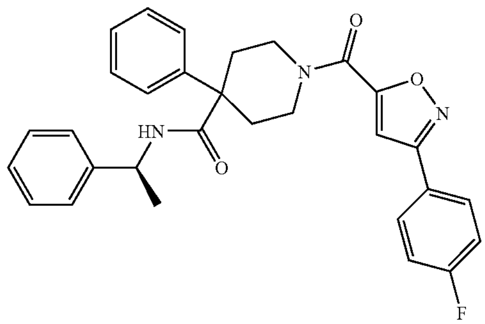 | 497.57 | 1-[3-(4-Fluoro-phenyl)-isoxazole-5-carbonyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 3-(4-fluoro-phenyl)-isoxazole-5-carboxylic acid (commercially available) | 498.3 |
| 63 | 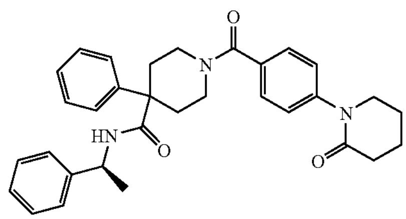 | 509.65 | 1-[4-(2-Oxo-piperidin-1-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-aceticacid (intermediate 4) and 4-(2-oxo-piperidin-1-yl)-benzoic acid (commercially available) | 510.5 |
| 64 | 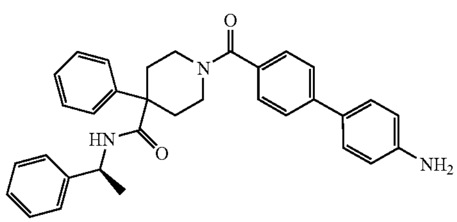 | 503.65 | 1-(4'-Amino-biphenyl-4-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4'-amino-biphenyl-4-carboxylic acid (commercially available) | 504.3 |
| 65 | 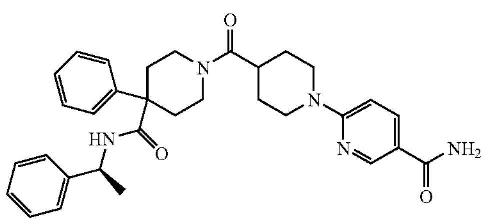 | 539.68 | 4-[4-Phenyl-4-((S)-1-phenyl-ethylcarbamoyl)-piperidine-1-carbonyl]-3,4,5,6-tetrahydro-2H-[1,2']bipyridinyl-5'-carboxylic acid amide | 4-Phenyl-piperidine-4-carboxylic acid ((S)-1-phenyl-ethyl)-amide; compound with trifluoro-acetic acid (intermediate 4) and 5'-carbamoyl-3,4,5,6-tetrahydro-2H-[1,2']bipyridinyl-4-carboxylic acid (commercially available) | 540.4 |
| 66 | 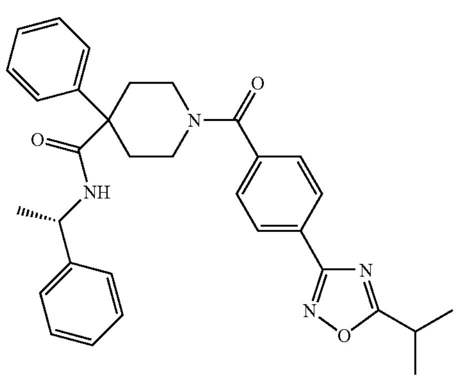 | 522.646 | 1-[4-(5-Isopropyl-[1,2,4]oxadiazol-3-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(5-isopropyl-[1,2,4]oxadiazol-3-yl)-benzoic acid (commercially available) | 523.4 |

TABLE 2-continued

| No | structure | MW | Systematic Name | starting materials | MW (MH+) |
|---|---|---|---|---|---|
| 67 | 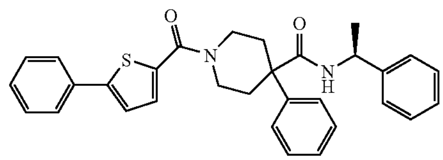 | 494.66 | 4-Phenyl-1-(5-phenyl-thiophene-2-carbonyl)-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 5-phenyl-thiophene-2-carboxylic acid (commercially available) | 495.4 |
| 68 | 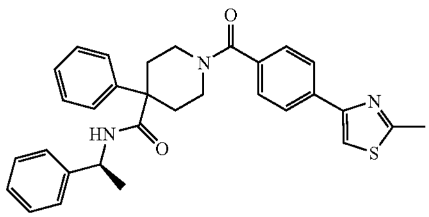 | 509.67 | 1-[4-(2-Methyl-thiazol-4-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(2-methyl-thiazol-4-yl)-benzoic acid (commercially available) | 510.4 |
| 69 | 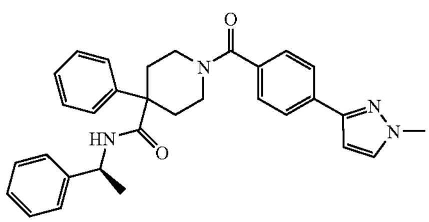 | 492.62 | 1-[4-(1-Methyl-1H-pyrazol-3-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(1-methyl-1-H-pyrazol 3-yl)-benzoic acid (commercially available) | 493.3 |
| 70 | 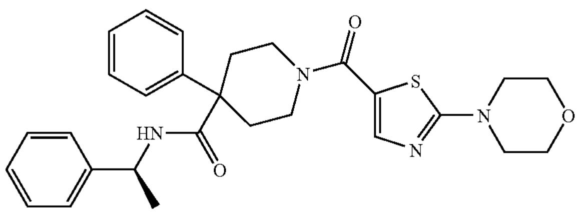 | 504.65 | 1-(2-Morpholin 4-yl-thiazole-5-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 2-morpholin-4-yl-thiazole-5-carboxylic acid (commercially available) | 505.2 |
| 71 | 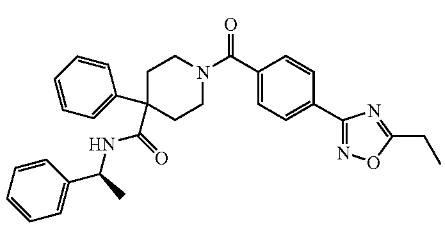 | 508.62 | 1-[4-(5-Ethyl-[1,2,4]oxa-diazol-3-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(5-ethyl-[1,2,4]oxadiazol-3-yl) benzoic acid (commercially available) | 509.3 |

TABLE 2-continued

| No | structure | MW | Systematic Name | starting materials | MW (MH+) |
|---|---|---|---|---|---|
| 72 | 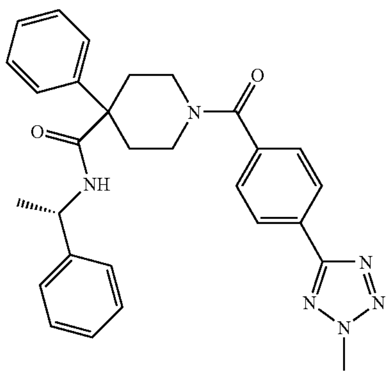 | 494.59 | 1-[4-(2-Methyl-2H-tetrazol-5-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(2-methyl-2H-tetrazol-5-yl)-benzoic acid (commercially available) | 495.4 |
| 73 | 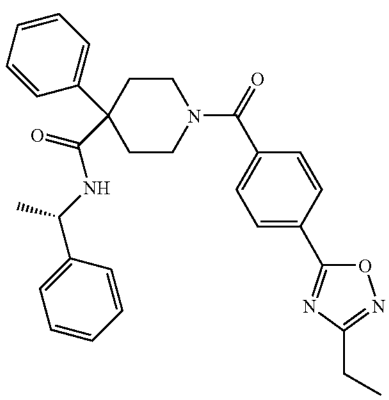 | 508.619 | 1-[4-(3-Ethyl-[1,2,4]oxadiazol-5-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(3-ethyl-[1,2,4]oxadiazol-5-yl)-benzoic acid (commercially available) | 509.4 |
| 74 | 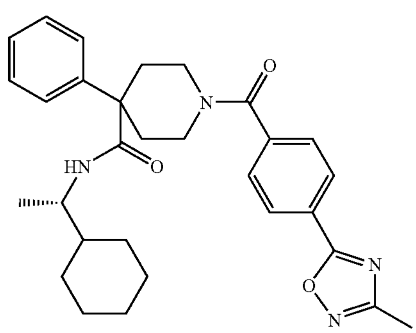 | 500.639 | 1-[4-(3-Methyl-[1,2,4]oxadiazol-5-yl)-benzoyl]-4-phenyl-piperidine-4-carboxylic acid ((S)-1-cyclohexyl-ethyl)-amide | 4-Phenyl-piperidine-4-carboxylic acid ((S)-1-cyclohexyl-ethyl) amide; compound with trifluoro-acetic acid (intermediate 8) and 4-(3-methyl-[1,2,4]oxadiazol-5yl)-benzoic acid (commercially available) | 501.4 |
| 75 | 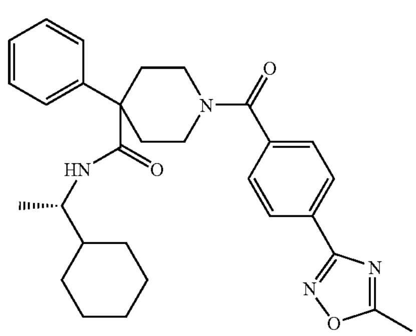 | 500.639 | 1-[4-(5-Methyl-[1,2,4]oxadiazol-3-yl)-benzoyl]-4-phenyl-piperidine-4-carboxylic acid ((S)-1-cyclohexyl-ethyl)-amide | 4-Phenyl-piperidine-4-carboxylic acid ((S)-1-cyclohexyl-ethyl)-amide; compound with trifluoro-acetic acid (intermediate 8) and 4-(5-methyl-[1,2,4]oxadiazol-3-yl)-benzoic acid (commercially available) | 501.4 |

TABLE 2-continued

| No | structure | MW | Systematic Name | starting materials | MW (MH+) |
|---|---|---|---|---|---|
| 76 | 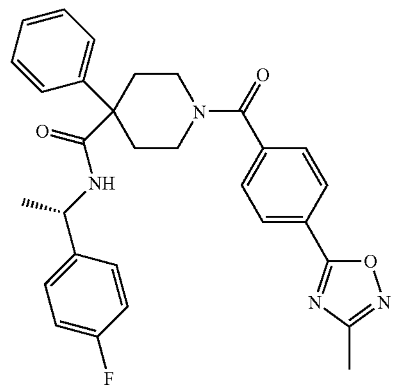 | 512.582 | 1-[4-(3-Methyl-[1,2,4]oxadiazol-5-yl)-benzoyl]-4-phenyl-piperidine-4-carboxylic acid [(S)-1-(4-fluoro-phenyl)-ethyl]-amide | 4-Phenyl-piperidine-4-carboxylic acid [(S)-1-(4-fluoro-phenyl)-ethyl]-amide; compound with trifluoro-acetic acid (intermediate 2) and 4-(3-methyl-[1,2,4]oxadiazol-5yl)-benzoic acid (commercially available) | 513.4 |
| 77 | 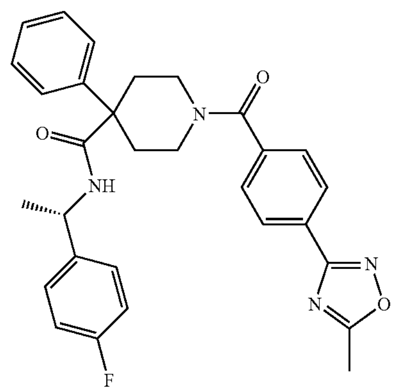 | 512.528 | 1-[4-(5-Methyl-[1,2,4]oxadiazol-3-yl)-benzoyl]-4-phenyl-piperidine-4-carboxylic acid [(S)-1-(4-fluoro-phenyl)-ethyl]-amide | 4-Phenyl-piperidine-4-carboxylic acid [(S)-1-(4-fluoro-phenyl)-ethyl]-amide; compound with trifluoro-acetic acid (intermediate 2) and 4-(5-methyl-[1,2,4]oxadiazol-3-yl)-benzoic acid (commercially available) | 513.4 |
| 78 | 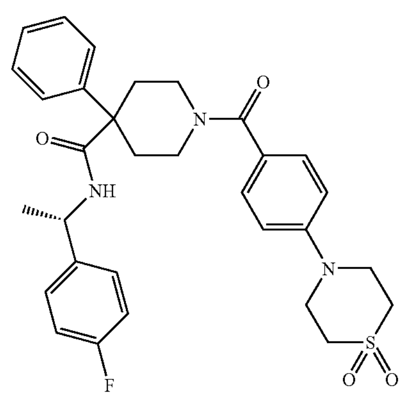 | 563.691 | 1-[4-(1,1-Dioxo-1λ6-thiomorpholin-4-yl)-benzoyl]-4-phenyl-piperidine-4-carboxylic acid [(S)-1-(4-fluoro-phenyl)-ethyl]-amide | 4-Phenyl-piperidine-4-carboxylic acid [(S)-1-(4-fluoro-phenyl)-ethyl]-amide; compound with trifluoro-acetic acid (intermediate 2) and 4-(1,1-dioxo-1λ6-4-thiazinan-4-yl)benzenecarboxylic acid (commercially available) | 564.3 |
| 79 | 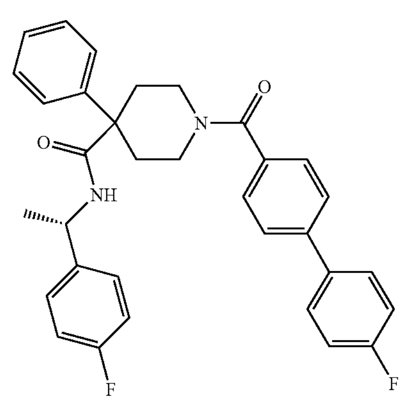 | 524.608 | 1-(4'-Fluoro-biphenyl-4-carbonyl)-4-phenyl-piperidine-4-carboxylic acid [(S)-1-(4-fluoro-phenyl)-ethyl]-amide | 4-Phenyl-piperidine-4-carboxylic acid [(S)-1-(4-fluoro-phenyl)-ethyl]-amide; compound with trifluoro-acetic acid (intermediate 2) and 4'-fluoro-biphenyl-4-carboxylic acid (commercially available) | 525.4 |

TABLE 2-continued

| No | structure | MW | Systematic Name | starting materials | MW (MH+) |
|---|---|---|---|---|---|
| 80 | 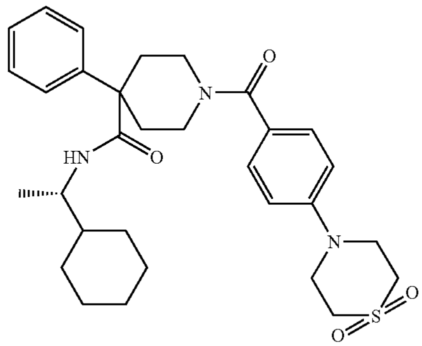 | 551.748 | 1-[4-(1,1-Dioxo-1λ6-thiomorpholin-4-yl)-benzoyl]-4-phenyl-piperidine-4-carboxylic acid ((S)-1-cyclohexyl-ethyl)-amide | 4-Phenyl-piperidine-4-carboxylic acid ((S)-1-cyclohexyl-ethyl)-amide; compound with trifluoro-acetic acid (intermediate 8) and 4-(1,1-dioxo-1λ6-4-thiazinan-4-yl)benzenecarboxylic acid (commercially available) | 552.4 |
| 81 | 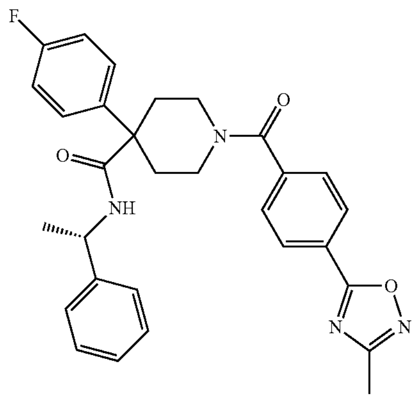 | 512.582 | 4-(4-Fluoro-phenyl)-1-[4-(3-methyl-[1,2,4]oxadiazol-5-yl)-benzoyl]-piperidine-4-carboxylic acid ((S)-1-phenyl-ethyl)-amide | 4-(4-Fluoro-phenyl)-piperidine-4-carboxylic acid ((S)-1-phenyl-ethyl)-amide; compound with trifluoro-acetic acid (intermediate 3) and 4-(3-methyl-[1,2,4]oxadiazol-5yl)-benzoic acid | 513.5 |
| 82 | 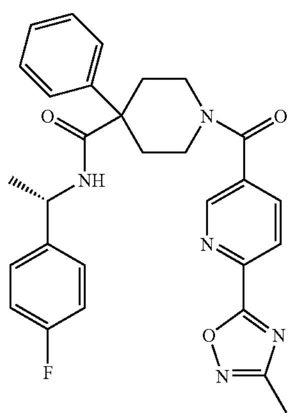 | 513.57 | 1-[6-(3-Methyl-[1,2,4]oxadiazol-5-yl)-pyridine-3-carbonyl]-4-phenyl-piperidine-4-carboxylic acid [(S)-1-(4-fluoro-phenyl)-ethyl]-amide | 4-Phenyl-piperidine-4-carboxylic acid [(S)-1-(4-fluoro-phenyl)-ethyl]-amide; compound with trifluoro-acetic acid (intermediate 2) and 6-(3-methyl-[1,2,4]oxadiazol-5-yl)-nicotinic acid (intermediate 17) | 514.4 |
| 83 | 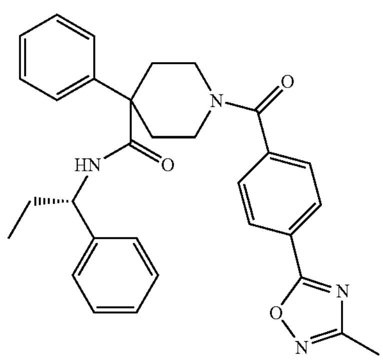 | 508.619 | 1-[4-(3-Methyl-[1,2,4]oxadiazol-5-yl)-benzoyl]-4-phenyl-piperidine 4-carboxylic acid ((S)-1-phenyl-propyl)-amide | 4-Phenyl-piperidine-4-carboxylic acid ((S)-1-phenyl-propyl)-amide; compound with trifluoro-acetic acid (intermediate 5) and 4-(3-methyl-[1,2,4]oxadiazol-5yl)-benzoic acid (commercially available) | 509.3 |

TABLE 2-continued

| No | structure | MW | Systematic Name | starting materials | MW (MH+) |
|---|---|---|---|---|---|
| 84 | 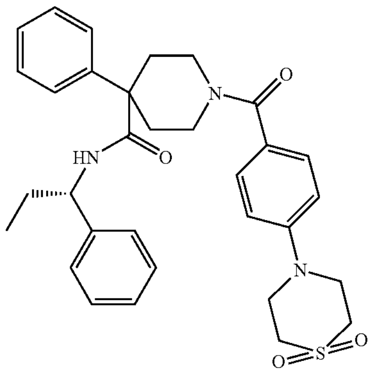 | 559.727 | 1-[4-(1,1-Dioxo-1λ6-thiomorpholin-4-yl)-benzoyl]-4-phenyl-piperidine-4-carboxylic acid ((S)-1-phenyl-propyl)-amide | 4-Phenyl-piperidine-4-carboxylic acid ((S)-1-phenyl-propyl)-amide; compound with trifluoro-acetic acid (intermediate 5) and 4-(1,1-dioxo-1λ6-4-thiazinan-4-yl)benzenecarboxylic acid (commercially available) | 560.3 |
| 85 | 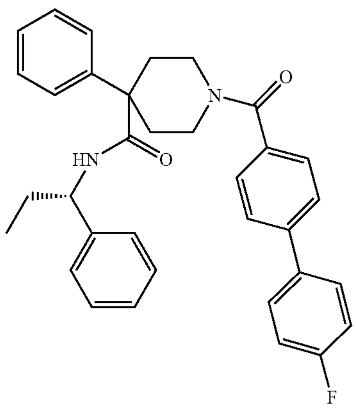 | 520.645 | 1-(4'-Fluoro-biphenyl-4-carbonyl)-4-phenyl-piperidine-4-carboxylic acid ((S)-1-phenyl-propyl)-amide | 4-Phenyl-piperidine-4-carboxylic acid ((S)-1-phenyl-propyl)-amide; compound with trifluoro-acetic acid (intermediate 5) and 4'-fluoro-biphenyl-4-carboxylic acid (commercially available) | 521.4 |
| 86 | 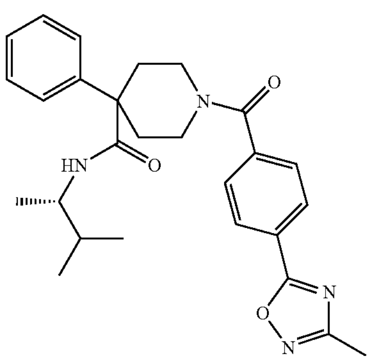 | 460.575 | 1-[4-(3-Methyl-[1,2,4]oxadiazol-5-yl)-benzoyl]-4-phenyl-piperidine-4-carboxylic acid ((S)-1,2-dimethyl-propyl)-amide | 4-Phenyl-piperidine-4-carboxylic acid ((S) 1,2-dimethyl-propyl)-amide; compound with trifluoro-acetic acid (intermediate 9) and 4-(3-methyl-[1,2,4]oxadiazol-5yl)-benzoic acid (commercially available) | 461.3 |
| 87 | 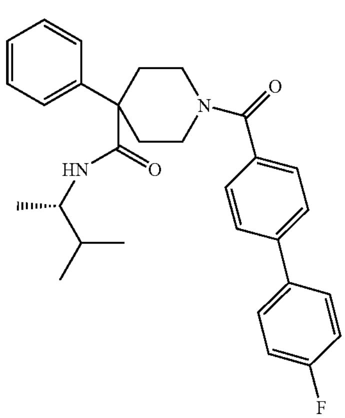 | 472.601 | 1-(4'-Fluoro-biphenyl-4-carbonyl)-4-phenyl-piperidine-4-carboxylic acid ((S)-1,2-dimethyl-propyl)-amide | 4-Phenyl-piperidine-4-carboxylic acid ((S)-1,2-dimethyl-propyl)-amide; compound with trifluoro-acetic acid (intermediate 9) and 4'-fluoro-biphenyl-4-carboxylic acid (commercially available) | 473.3 |

TABLE 2-continued

| No | structure | MW | Systematic Name | starting materials | MW (MH+) |
|---|---|---|---|---|---|
| 88 | 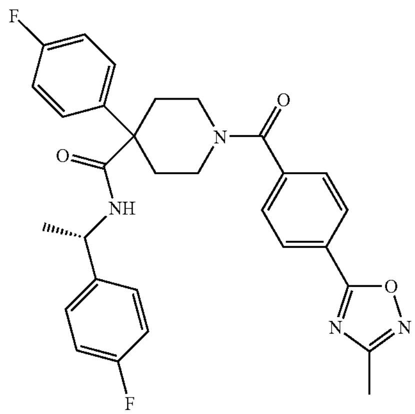 | 530.572 | 4-(4-Fluoro-phenyl)-1-{4-(3-methyl-[1,2,4]oxa-diazol-5-yl)-benzoyl]piperidine-4-carboxylic acid [(S)-1-(4-fluoro-phenyl)-ethyl]-amide | 4-(4-Fluoro-phenyl)-piperidine-4-carboxylic acid [(S)-1-(4-fluoro-phenyl)-ethyl]-amide; compound with trifluoro-acetic acid (intermediate 1) and 4-(3-methyl-[1,2,4]oxadiazol-5y1)-benzoic acid (commercially available) | 531.3 |
| 89 | 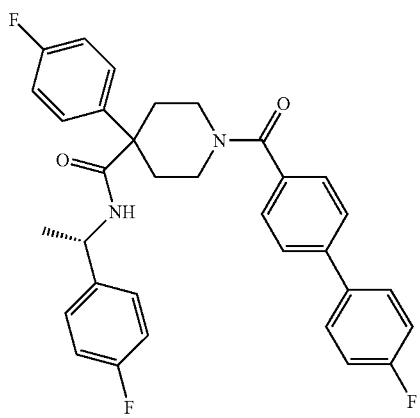 | 542.598 | 1-(4'-Fluoro-biphenyl-4-carbonyl)-4-(4-fluoro-piperidine-phenyl)-4-carboxylic acid [(S)-1-(4-fluoro-phenyl)-ethyl]-amide | 4-(4-Fluoro-phenyl)-piperidine-4-carboxylic acid [(S)-1-(4-fluoro-phenyl)-ethyl]-amide; trifluoro-acetic acid compound with (intermediate 1) and 4'-fluoro-biphenyl-4-carboxylic acid (commercially available) | 543.4 |
| 90 | 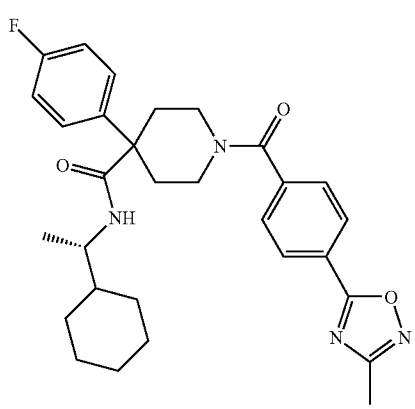 | 518.629 | 4-(4-Fluoro-phenyl)-1-methyl-[1,2,4]oxa-diazol-5-yl)-benzoyl]-piperidine-4-carboxylic acid ((S)-1-cyclohexyl-ethyl)-amide | 4-(4-Fluoro-phenyl)-piperidine-4-carboxylic acid ((S)-1-cyclohexyl-ethyl)-amide trifluoro acetic acid (intermediate 7) and 4-(3-methyl-[1,2,4]oxadiazol-5yl)-benzoic acid (commercially available) | 519.3 |

TABLE 2-continued

| No | structure | MW | Systematic Name | starting materials | MW (MH+) |
|---|---|---|---|---|---|
| 91 | 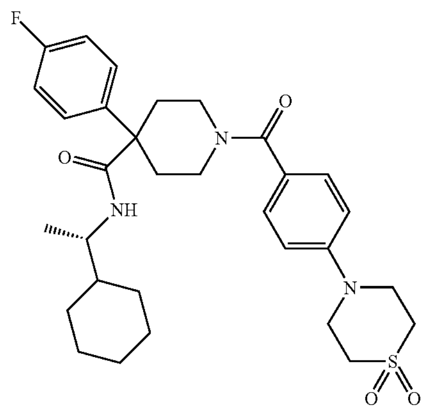 | 569.738 | 1-[4-(1,1-Dioxo-1λ6-thiomorpholin-4-yl)-benzoyl]-4-(4-fluoro-phenyl)-piperidine-4-carboxylic acid ((S)-1-cyclohexyl-ethyl)-amide | 4-(4-Fluoro-phenyl)-piperidine-4-carboxylic acid ((S)-1-cyclohexyl ethyl)-amide trifluoro acetic acid (intermediate 7) and 4-(1,1-dioxo-1λ6-4-thiazinan-4-yl)benzenecarboxylic acid (commercially available) | 570.5 |
| 92 | 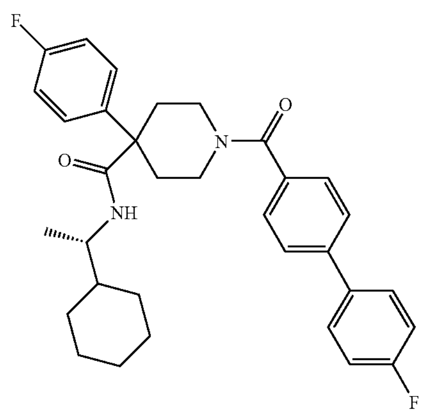 | 530.655 | 1-(4'-Fluoro-biphenyl-4-carbonyl)-4-(4-fluoro-phenyl)-piperidine-4-carboxylic acid ((S)-1-cyclohexyl-ethyl)-amide | 4-(4-Fluoro-phenyl)-piperidine-4-carboxylic acid ((S)-1-cyclohexyl-ethyl)-amide trifluoro acetic acid (intermediate 7) and 4'-fluoro-biphenyl-4-carboxylic acid (commercially available) | 531.3 |
| 93 | 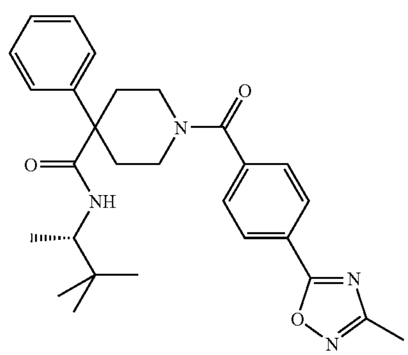 | 474.602 | 1-[4-(3-Methyl-[1,2,4]oxadiazol-5-yl)-benzoyl]-4-phenyl-piperidine-4-carboxylic acid ((S)-1,2,2-trimethyl-propyl) amide | 4-Phenyl-piperidine-4-carboxylic acid ((S)-1,2,2-trimethyl-propyl)-amide; compound with trifluoro-acetic acid (intermediate 10) and 4-(3-methyl-[1,2,4]oxadiazol-5yl)-benzoic acid (commercially available) | 475.4 |
| 94 | 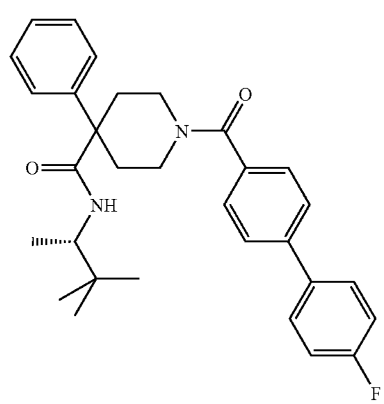 | 486.627 | 1-(4-Fluoro-biphenyl-4-carbonyl)-4-phenyl-piperidine-4-carboxylic acid ((S)-1,2,2-trimethyl-propyl)-amide | 4-Phenyl-piperidine-4-carboxylic acid ((S)-1,2,2-trimethyl-propyl)-amide; compound with trifluoro-acetic acid (intermediate 10) and 4'-fluoro-biphenyl-4-carboxylic acid (commercially available) | 487.4 |

TABLE 2-continued

| No | structure | MW | Systematic Name | starting materials | MW (MH+) |
|---|---|---|---|---|---|
| 95 | 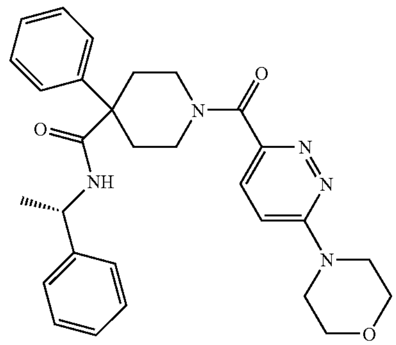 | 499.612 | 1-(6-Morpholin-4-yl-pyridazine-3-carbonyl)-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 6-morpholin-4-yl-pyridazine-3-carboxylic acid (commercially available) | 500.3 |
| 96 | 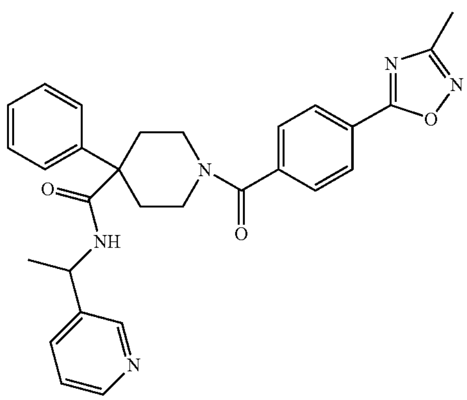 | 495.58 | 1-[4-(3-Methyl-[1,2,4]oxa-diazol-5-yl)-benzoyl]-4-phenyl-piperidine-4-carboxylic acid (1-pyridin-3-yl-ethyl)-amide | rac-4-Phenyl-piperidine-4-carboxylic acid (1-pyridin-3-yl-ethyl)-amide; compound with trifluoro-acetic acid (intermediate 11) and 4-(3-methyl-[1,2,4]oxadiazol-5yl)-benzoic acid (commercially available) | 496.5 |
| 97 | 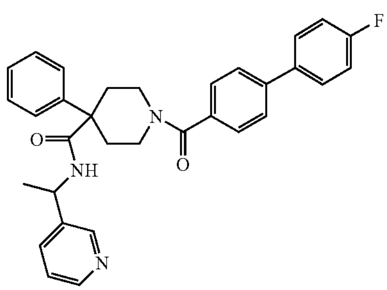 | 507.606 | 1-(4'-Fluoro-biphenyl-4-carbonyl)-4-phenyl-piperidine-4-carboxylic acid (1-pyridin-3-yl-ethyl)-amide | rac-4-Phenyl-piperidine-4-carboxylic acid (1-pyridin-3-yl-ethyl)-amide; compound with trifluoro-acetic acid (intermediate 11) and 4'-fluoro-biphenyl-4-carboxylic acid (commercially available) | 508.3 |
| 98 | 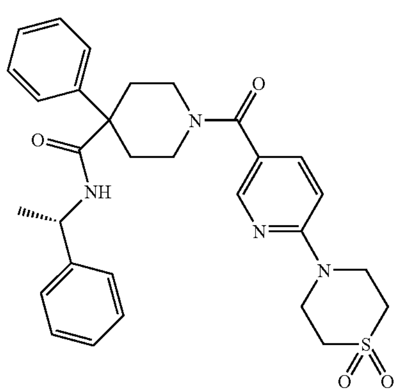 | 546.689 | 1-[6-(1,1-Dioxo-1λ6-thiomor-pholin-4-yl)-pyridine-3-carbonyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 6-(1,1-Dioxo-1λ6-thiomorpholin-4-yl)-nicotinic acid (intermediate 18) | 547.3 |

TABLE 2-continued

| No | structure | MW | Systematic Name | starting materials | MW (MH+) |
|---|---|---|---|---|---|
| 99 | 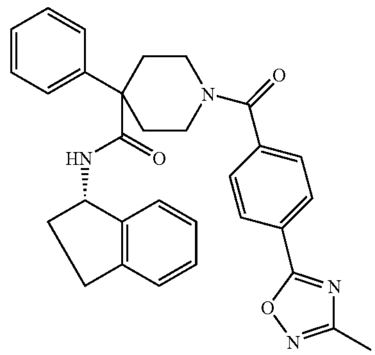 | 506.603 | 1-[4-(3-Methyl-[1,2,4]oxadiazol-5-yl)-benzoyl]-4-phenyl-piperidine 4-carboxylic acid (S)-indan-1-ylamide | 4-Phenyl-piperidine-4-carboxylic acid (S)-indan-1-ylamide; compound with trifluoro-acetic acid (intermediate 12) and 4-(3-methyl-[1,2,4]oxadiazol-5yl)-benzoic acid (commercially available) | 507.3 |
| 100 | 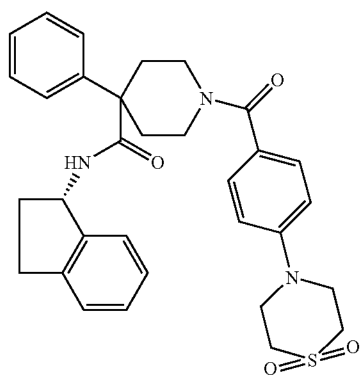 | 557.711 | 1-[4-(1,1-Dioxo-1λ6-thiomorpholin-4-yl)-benzoyl]-4-phenyl-piperidine-4-carboxylic acid (S)-indan-1-ylamide | 4-Phenyl-piperidine-4-carboxylic acid (S)-indan-1-ylamide; compound with trifluoro-acetic acid (intermediate 12) and 4-(1,1-dioxo-1λ6-4-thiazinan-4-yl)benzenecarboxylic acid (commercially available) | 558.3 |
| 101 | 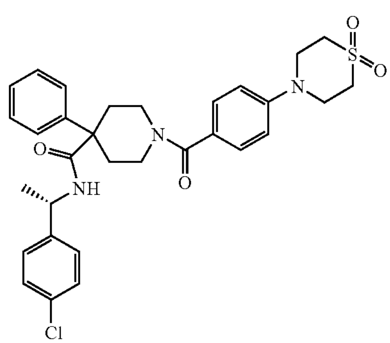 | 580.146 | 1-[4-(1,1-Dioxo-1λ6-thiomorpholin-4-yl)-benzoyl]-4-phenyl-pipendine-4-carboxylic acid [(S)-1-(4-chloro-phenyl)-ethyl]-amide | 4-Phenyl-piperidine-4-carboxylic acid [(S)-1-(4-chloro-phenyl)-ethyl]-amide; compound with trifluoro-acetic acid (intermediate 6) and 4-(1,1-dioxo-1λ6-4-thiazinan-4-yl)benzenecarboxylic acid (commercially available) | 580.2 |
| 102 | 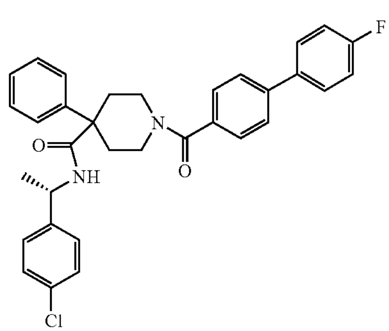 | 541.063 | 1-(4'-Fluoro-biphenyl-4-carbonyl)-4-phenyl-piperidine-4-carboxylic acid [(S)-1-(4-chloro-phenyl)-ethyl]-amide | 4-Phenyl-piperidine-4-carboxylic acid [(S)-1-(4-chloro-phenyl)-ethyl]-amide; compound with trifluoro-acetic acid (intermediate 6) and 4'-fluoro-biphenyl-4-carboxylic acid (commercially available) | 541.3 |

TABLE 2-continued

| No | structure | MW | Systematic Name | starting materials | MW (MH+) |
|---|---|---|---|---|---|
| 103 | 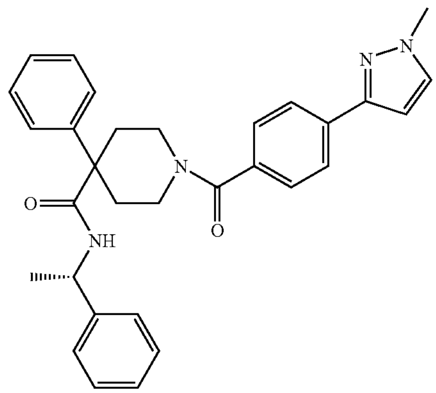 | 492.62 | 1-[4-(1-Methyl-1H-pyrazol-3-yl)-benzoyl]-4-phenyl-piperidine-4-carboxylic acid ((S)-1-phenyl-ethyl)-amide | 4-Phenyl-piperidine-4-carboxylic acid ((S)-1-phenyl-ethyl)-amide; compound with trifluoro-acetic acid (intermediate 4) and 4-(1-Methyl-1H-pyrazol-3-yl)-benzoic acid (commercially available) | 493.3 |
| 104 | 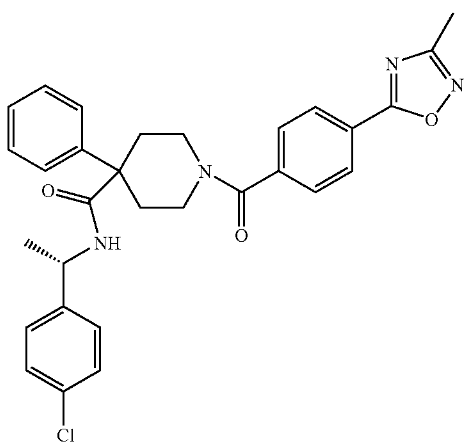 | 529.037 | 1-[4-(3-Methyl-[1,2,4]oxadiazol-5-yl)-benzoyl]-4-phenyl-piperidine-4-carboxylic acid [(S)-1-(4-chloro-phenyl)-ethyl]-amide | 4-Phenyl-piperidine-4-carboxylic acid [(S)-1-(4-chloro-phenyl)-ethyl]-amide; compound with trifluoro-acetic acid (intermediate 6) and 4-(3-methyl-[1,2,4]oxadiazol-5yl)-benzoic acid (commercially available) | 529.2 |
| 105 | 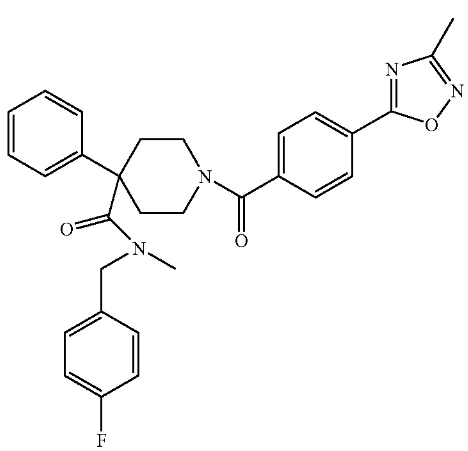 | 512.582 | 1-[4-(3-Methyl-[1,2,4]oxadiazol-5-yl)-benzoyl]-4-phenyl-piperidine-4-carboxylic acid (4-fluoro-benzyl)-methyl-amide | 4-Phenyl-piperidine-4-carboxylic acid (4-fluoro-benzyl)-methyl-amide; compound with trifluoro-acetic acid (intermediate 13) and 4-(3-methyl-[1,2,4]oxadiazol-5y1)-benzoic acid (commercially available) | 513.3 |

TABLE 2-continued

| No | structure | MW | Systematic Name | starting materials | MW (MH+) |
|---|---|---|---|---|---|
| 106 | 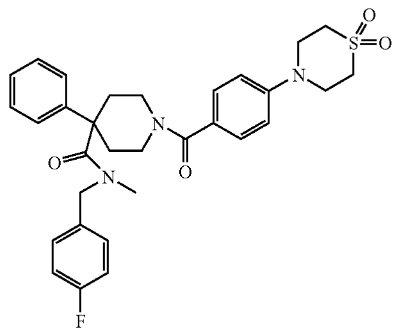 | 563.691 | 1-[4-(1,1-Dioxo-1λ6-thiomorpholin-4-yl)-benzoyl]-4-phenyl-piperidine-4-carboxylic acid (4-fluoro-benzyl)-methyl-amide | 4-Phenyl-piperidine-4-carboxylic acid (4-fluoro-benzyl)-methyl amide; compound with trifluoro-acetic acid (intermediate 13) and 4-(1,1-dioxo-1λ6-4-thiazinan-4-yl)benzenecarboxylic acid (commercially available) | 564.4 |
| 107 | 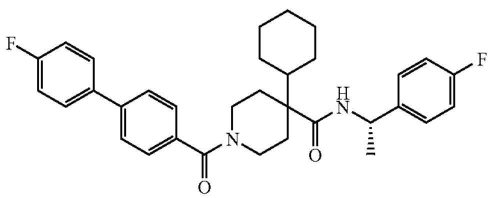 | 530.655 | 4-Cyclohexyl-1-(4'-fluoro-biphenyl-4-carbonyl)-piperidine-4-carboxylic acid [(S)-1-(4-fluoro-phenyl)-ethyl]-amide | 4-Cyclohexyl-piperidine-4-carboxylic acid [(S)-1-(4-fluoro-phenyl)-ethyl]-amide; hydrochloride (intermediate 14) and 4'-fluoro-biphenyl-4-carboxylic acid (commercially available) | 531.2 |
| 108 | 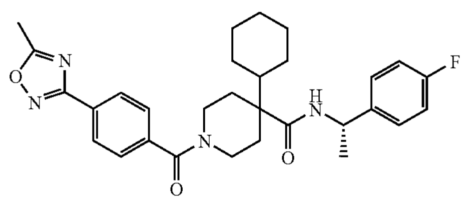 | 518.629 | 4-Cyclohexyl-1-[4-(5-methyl-[1,2,4]oxadiazol-3-yl)-benzoyl]-piperidine-4-carboxylic acid [(S)-1-(4-fluoro-phenyl)-ethyl]-amide | 4-Cyclohexyl-piperidine-4-carboxylic acid [(S)-1-(4-fluoro-phenyl)-ethyl]-amide; hydrochloride (intermediate 14) and 4-(5-methyl-[1,2,4]oxadiazol-3-yl)-benzoic acid (commercially available) | 519.3 |
| 109 | 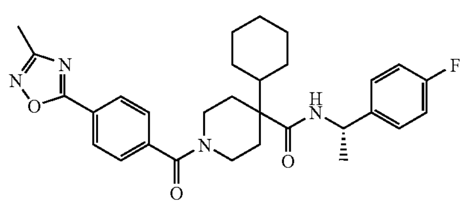 | 518.629 | 4-Cyclohexyl-1-[4-(3-methyl-[1,2,4]oxadiazol-5-yl)-benzoyl]-piperidine-4-carboxylic acid [(S)-1-(4-fluoro-phenyl)-ethyl]-amide | 4-Cyclohexyl-piperidine-4-carboxylic acid [(S)-1-(4-fluoro-phenyl)-ethyl]-amide; hydrochloride (intermediate 14) and 4-(3-methyl-[1,2,4]oxadiazol-5yl)-benzoic acid (commercially available) | 519.3 |
| 110 | 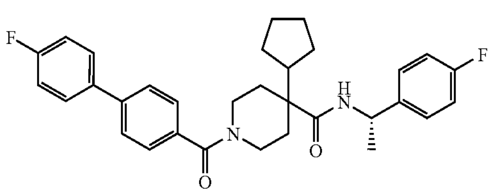 | 516.629 | 4-Cyclopentyl-1-(4'-fluoro-biphenyl-4-carbonyl)-piperidine-4-carboxylic acid [(S)-1-(4-fluoro-phenyl)-ethyl]-amide | 4-Cyclopentyl-piperidine-4-carboxylic acid [(S)-1-(4-fluoro-phenyl)-ethyl]-amide; hydrochloride (intermediate 15) and 4'-fluoro-biphenyl-4-carboxylic acid (commercially available) | 517.3 |

TABLE 2-continued

| No | structure | MW | Systematic Name | starting materials | MW (MH+) |
|---|---|---|---|---|---|
| 111 | 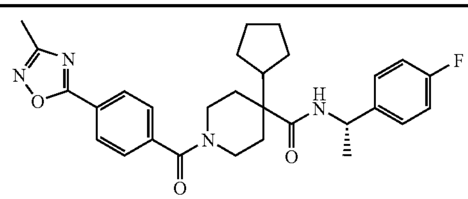 | 504.603 | 4-Cyclopentyl-1-[4-(3-methyl-[1,2,4]oxadiazol-5-yl)-benzoyl]-piperidine-4-carboxylic acid [(S)-1-(4-fluoro-phenyl)-ethyl]-amide | 4-Cyclopentyl-piperidine-4-carboxylic acid [(S)-1-(4-fluoro-phenyl)-ethyl]-amide; hydrochloride (intermediate 15) and 4-(3-methyl-[1,2,4]oxadiazol-5yl)-benzoic acid (commercially available) | 505.3 |
| 112 | 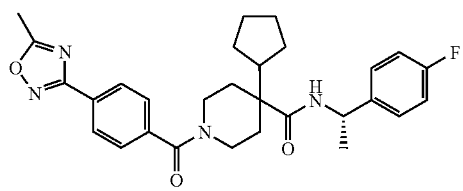 | 504.603 | 4-Cyclopentyl-1-[4-(5-methyl-[1,2,4]oxadiazol-3-yl)-benzoyl]-piperidine-4-carboxylic acid [(S)-1-(4-fluoro-phenyl)-ethyl]-amide | 4-Cyclopentyl-piperidine-4-carboxylic acid [(S)-1-(4-fluoro-phenyl)-ethyl]-amide; hydrochloride (intermediate 15) and 4-(5-methyl-[1,2,4]oxadiazol-3-yl)-benzoic acid (commercially available) | 505.3 |
| 113 | 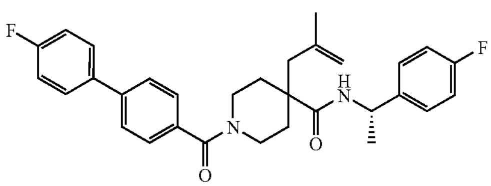 | 502.62 | 1-(4'-Fluoro-biphenyl-4-carbonyl)-4-(2-methyl-allyl)-piperidine-4-carboxylic acid [(S)-1-(4-fluoro-phenyl)-ethyl]-amide | 4-(2-Methyl-allyl)-piperidine-4-carboxylic acid [(S)-1-(4-fluoro-phenyl)-ethyl]-amide (intermediate 16) and 4'-fluoro-biphenyl-4-carboxylic acid (commercially available) | 503.2 |

Intermediate 19

1-[4-(3-Methyl-[1,2,4]oxadiazol-5-yl)-benzoyl]-4-phenyl-piperidine-4-carboxylic acid

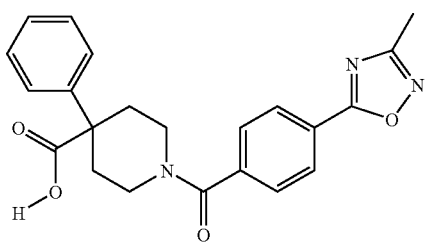

i) 4-Phenyl-piperidine-4-carboxylic acid methyl ester

To a solution of 4-phenyl-piperidine-4-carboxylic acid 4-toluene sulfonate (3.0 g, 0.008, mol) in methanol was added sulfuric acid (1.28 mL, 0.023 mol) and heated under reflux for 12 h. Excess methanol was evaporated and the residue poured into a cooled mixture of ice and 32% aqueous NaOH (if necessary adjust pH to >10). The aqueous phase was extracted with DCM, the combined organic phases were dried over Na$_2$SO$_4$ and the solvent was evaporated. The residue was evaporated several times with toluene and used crude for the next reaction.

ii) 1-[4-(3-Methyl-[1,2,4]oxadiazol-5-yl)-benzoyl]-4-phenyl-piperidine-4-carboxylic acid methyl ester To a mixture of 4-(3-methyl-1,2,4-oxadiazol-5-yl)benzoic acid (408 mg, 2.0 mmol) (commercially available), EDC (614 mg, 3.2 mmol), HOBT (490 mg, 3.2 mmol) and triethylamine (1031 µL, 7.4 mmol) in DCM (6 ml) at room temperature was added slowly a solution of 4-phenyl-piperidine-4-carboxylic acid methyl ester (439 mg, 2.0 mmol) in DCM (3 mL). The reaction mixture was stirred at room temperature for 12 h. The reaction mixture was subjected to flash chromatography with n-heptane and ethyl acetate over a 70 g silica gel column to give 690 mg 1-[4-(3-methyl-[1,2,4]oxadiazol-5-yl)-benzoyl]-4-phenyl-piperidine-4-carboxylic acid methyl ester. MS ISP (m/e): 406.3 [(M+H)$^+$].

iii) 1-[4-(3-Methyl-[1,2,4]oxadiazol-5-yl)-benzoyl]-4-phenyl-piperidine-4-carboxylic acid To a solution of 1-[4-(3-methyl-[1,2,4]oxadiazol-5-yl)-benzoyl]-4-phenyl-piperidine-4-carboxylic acid methyl ester (156 mg, 0.385 mmol) in methanol (2 mL) was added an aqueous solution of KOH (3M, 770 µL, 2.31 mmol) and stirred at 65° C. for 12 h. The mixture was cooled to 0° C. and adjusted to pH=7 with 1N aqueous HCl. The solvent was evaporated under reduced pressure and the residue was co-evaporated with toluene to give 316 mg (purity ~48%) 1-[4-(3-methyl-[1,2,4]oxadiazol-5-yl)-benzoyl]-4-phenyl-piperidine-4-carboxylic acid which was used directly for the next step. MS ISP (m/e): 392.2 [(M+H)$^+$].

Intermediate 20

4-Cyclopropylmethyl-1-(4'-fluoro-biphenyl-4-carbonyl)-piperidine-4-carboxylic acid

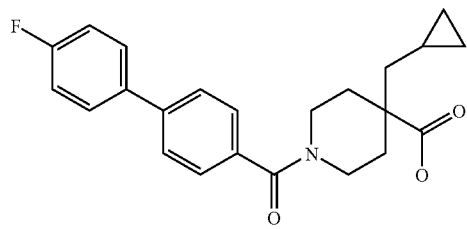

i) 4-Cyclopropylmethyl-piperidine-4-carboxylic acid ethyl ester, hydrochloride

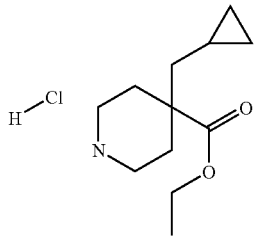

A mixture of 0.5 g (1.6 mmol) 1-tert-butyl 4-ethyl 4-(cyclopropylmethyl)piperidine-1,4-dicarboxylate (commercially available) in 20 mL dioxane was treated with 4 mL 4N HCl in dioxane and stirred at room temperature over night. The mixture was evaporated to dryness and used without further purification in the consecutive step.

ii) 4-Cyclopropylmethyl-1-(4'-fluoro-biphenyl-4-carbonyl)-piperidine-4-carboxylic acid ethyl ester

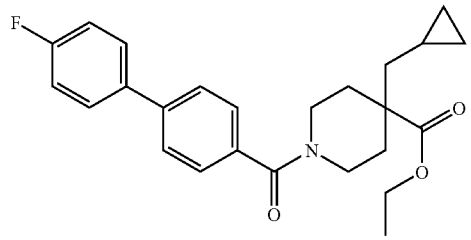

A mixture of 0.31 g (1.4 mmol) 4'-fluoro-biphenyl-4-carboxylic acid, 0.426 g (1.71 mmol) 4-cyclopropylmethyl-piperidine-4-carboxylic acid ethyl ester, hydrochloride, 0.552 g (1.71 mmol) TBTU and 1.23 mL DIPEA in 25 mL DMF was stirred at room temperature over night. After evaporation to dryness the residue was purified by column chromatography on silica eluting with a gradient formed from ethyl acetate and heptane to yield after evaporation of the product containing fractions 0.51 g (87%) of the title compound as light yellow viscous oil. MS ISP (m/e): 410.3 [(M+H)$^+$].

iii) 4-Cyclopropylmethyl-1-(4'-fluoro-biphenyl-4-carbonyl)-piperidine-4-carboxylic acid A mixture of 0.51 g (1.24 mmol) 4-cyclopropylmethyl-1-(4'-fluoro-biphenyl-4-carbonyl)-piperidine-4-carboxylic acid ethyl ester and 1.87 mL 4N NaOH aq. in 5 mL ethanol was stirred at 75° C. for a prolonged period of time. After concentration of the mixture ice-water was added and the pH was adjusted to pH=2 with HCl aq. The mixture was extracted with ethyl acetate, the combined organic layers were dried with Na$_2$SO$_4$, filtered, evaporated to dryness and purified by column chromatography on silica eluting with a gradient formed from ethyl acetate, heptane and formic acid to yield after evaporation of the product containing fractions 0.146 g (31%) of the title compound as white foam. MS ISP (m/e): 382.3 [(M+H)$^+$].

Intermediate 21

1-(4'-Fluoro-biphenyl-4-carbonyl)-4-(2,2,2-trifluoro-ethyl)-piperidine-4-carboxylic acid

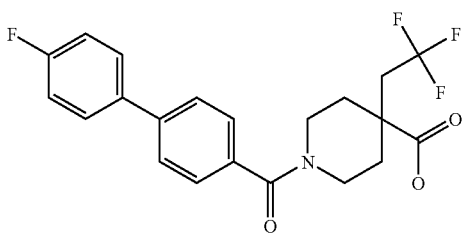

i) 4-(2,2,2-Trifluoro-ethyl)-piperidine-1,4-dicarboxylic acid 1-tert-butyl ester 4-ethyl ester

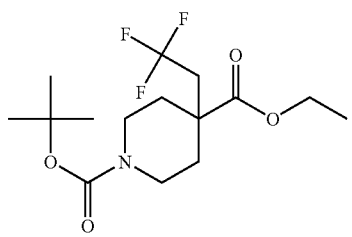

Under a argon atmosphere a vacuum dried 750 mL four necked flask (with mechanical stirrer) was charged with 6.6 mL diisopropylamine and 100 mL THF. The solution was cooled to −5° C./−10° C. 29.1 mL of 1.6M n-butyllithium in hexane was added over a period of 20 min. The light yellow solution was stirred for 30 min at −5°/−10° C. and afterwards cooled to −75° C. A solution of 10 g (38.8 mmol) ethyl 1-tert-butoxycarbonylpiperidine in 75 mL THF was added over a period of 50 min. The yellow solution was stirred at −75° C. for 2 h. A solution of 9.8 g (46.7 mmol) 2,2,2-trifluoroethyl iodide in 25 mL THF was added dropwise over a period of 45 min. The reaction was stirred for 1 h at −75° C. and allowed to warm up over night to ambient temperature. The reaction was cooled down to 0° C., quenched with 250 mL 10% citric acid aq. solution The aqueous layer was separated and extracted twice with 200 mL ethyl acetate. The organic layers were washed once with 200 mL brine, dried over Na$_2$SO$_4$, filtered and evaporated.

The crude oil was purified by column chromatography on silica with a gradient formed from heptane and TBME to yield after evaporation of the product containing fractions 5.2 g (39%) of the title compound as light yellow oil. MS ISP (m/e): 357.1 [(M+H)$^+$].

ii) 4-(2,2,2-Trifluoro-ethyl)-piperidine-4-carboxylic acid ethyl Ester, hydrochloride

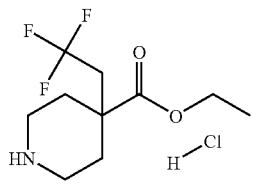

In analogy to the procedure described for the synthesis of 4-cyclopropylmethyl-piperidine-4-carboxylic acid ethyl ester, hydrochloride (intermediate 20, step i) the title compound was prepared from 4-(2,2,2-Trifluoro-ethyl)-piperidine-1,4-dicarboxylic acid 1-tert-butyl ester 4-ethyl ester through cleavage of the Boc-group with HCl in dioxane. MS ISP (m/e): 357.1 [(M+H)$^+$].

iii) 1-(4'-Fluoro-biphenyl-4-carbonyl)-4-(2,2,2-trifluoro-ethyl)-piperidine-4-carboxylic acid ethyl ester

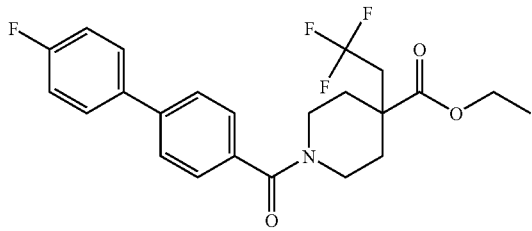

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 4-(2,2,2-Trifluoro-ethyl)-piperidine-4-carboxylic acid ethyl ester, hydrochloride and 4'-fluoro-biphenyl-4-carboxylic acid (commercially available). MS ISP (m/e): 438.2 [(M+H)$^+$].

iv) 1-(4'-Fluoro-biphenyl-4-carbonyl)-4-(2,2,2-trifluoro-ethyl)-piperidine-4-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 1-(4'-fluoro-biphenyl-4-carbonyl)-4-(2,2,2-trifluoro-ethyl)-piperidine-4-carboxylic acid ethyl ester. MS ISP (m/e): 410.2 [(M+H)$^+$].

Intermediate 22

4-Cyclobutylmethyl-1-(4'-fluoro-biphenyl-4-carbonyl)-piperidine-4-carboxylic acid

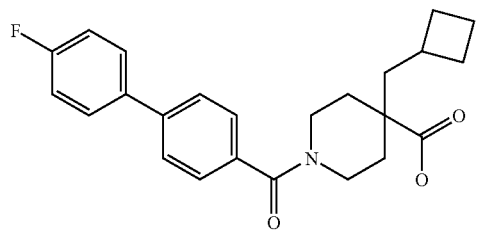

i) 4-Cyclobutylmethyl-piperidine-1,4-dicarboxylic acid 1-tert-butyl ester 4-ethyl ester

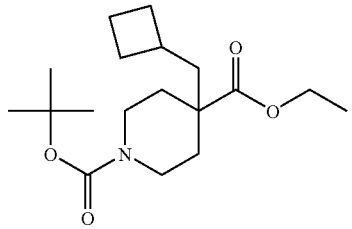

In analogy to the procedure described for the synthesis of 4-(2,2,2-trifluoro-ethyl)-piperidine-1,4-dicarboxylic acid 1-tert-butyl ester 4-ethyl ester (intermediate 21, step i) the title compound was prepared from 1-tert-butoxycarbonylpiperidine and cyclobutylmethyl bromide. MS (m/e): 326.3 (M+H$^+$)

ii) 4-Cyclobutylmethyl-piperidine-4-carboxylic acid ethyl ester, hydrochloride

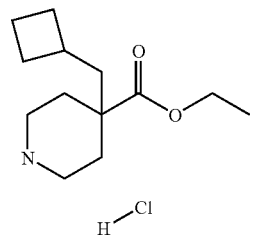

In analogy to the procedure described for the synthesis of 4-cyclopropylmethyl-piperidine-4-carboxylic acid ethyl ester, hydrochloride (intermediate 20, step i) the title compound was prepared from 4-cyclobutylmethyl-piperidine-1, 4-dicarboxylic acid 1-tert-butyl ester 4-ethyl ester through cleavage of the Boc-group with HCl in dioxane. MS ISP (m/e): 226.3 [(M+H)$^+$].

iii) 4-Cyclobutylmethyl-1-(4'-fluoro-biphenyl-4-carbonyl)-piperidine-4-carboxylic acid ethyl ester

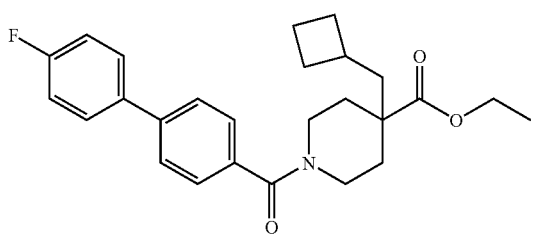

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 4-cyclobutylmethyl-piperidine-4-carboxylic acid ethyl ester, hydrochloride and 4'-fluoro-biphenyl-4-carboxylic acid (commercially available). MS ISP (m/e): 424.2 [(M+H)$^+$].

iv) 4-Cyclobutylmethyl-1-(4'-fluoro-biphenyl-4-carbonyl)-piperidine-4-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 4-cyclobutylmethyl-1-(4'-fluoro-biphenyl-4-carbonyl)-piperidine-4-carboxylic acid ethyl ester. MS ISP (m/e): 396.2 [(M+H)$^+$].

Intermediate 23

1-(4'-Fluoro-biphenyl-4-carbonyl)-4-isobutyl-piperidine-4-carboxylic acid

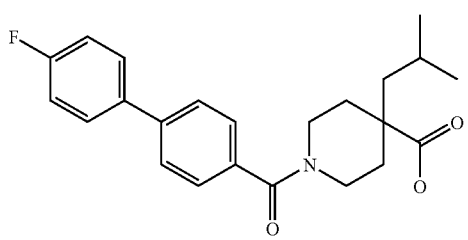

i) 4-Isobutyl-piperidine-1,4-dicarboxylic acid 1-tert-butyl ester 4-ethyl ester

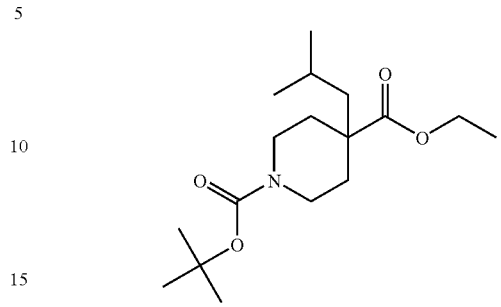

In analogy to the procedure described for the synthesis of 4-(2,2,2-trifluoro-ethyl)-piperidine-1,4-dicarboxylic acid 1-tert-butyl ester 4-ethyl ester (intermediate 21, step i) the title compound was prepared from 1-tert-butoxycarbonylpiperidine and 1-iodo-2-methylpropane. MS ISP (m/e): 326.2 [(M+NH$_4$)$^+$].

ii) 4-Isobutyl-piperidine-4-carboxylic acid ethyl ester, hydrochloride

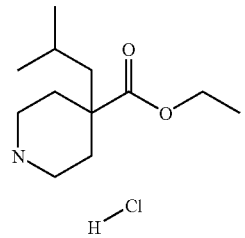

In analogy to the procedure described for the synthesis of 4-cyclopropylmethyl-piperidine-4-carboxylic acid ethyl ester, hydrochloride (intermediate 20, step i) the title compound was prepared from 4-isobutylmethyl-piperidine-1,4-dicarboxylic acid 1-tert-butyl ester 4-ethyl ester through cleavage of the Boc-group with HCl in dioxane. MS ISP (m/e): 214.3 [(M+H)$^+$].

iii) 1-(4'-Fluoro-biphenyl-4-carbonyl)-4-isobutyl-piperidine-4-carboxylic acid ethyl ester

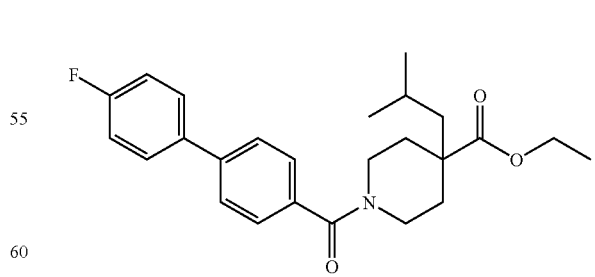

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 4-isobutylmethyl-piperidine-4-carboxylic acid ethyl ester, hydrochloride and 4'-fluoro-biphenyl-4-carboxylic acid (commercially available). MS ISP (m/e): 412.3 [(M+H)+].

iv) 1-(4'-Fluoro-biphenyl-4-carbonyl)-4-isobutyl-piperidine-4-carboxylic acid

In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 4-isobutylmethyl-1-(4'-fluoro-biphenyl-4-carbonyl)-piperidine-4-carboxylic acid ethyl ester. MS ISP (m/e): 384.2 [(M+H)+].

Intermediate 24

5-Fluoro-1'-(4'-fluoro-biphenyl-4-carbonyl)-2',3',5',6'-tetrahydro-1'H-[2,4']bipyridinyl-4'-carboxylic acid

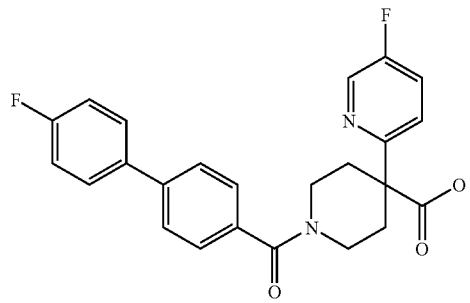

i) 5-Fluoro-2',3',5',6'-tetrahydro-[2,4']bipyridinyl-1',4'-dicarboxylic acid 1'-tert-butyl ester 4'-ethyl ester

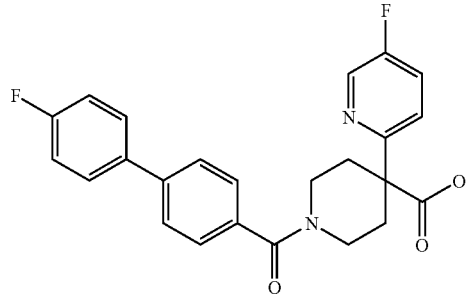

Under an inert atmosphere a 250 mL three necked round bottom flask (flame dried) with a magnetic stirring bar was charged with 4 g (22.7 mmol) 2-bromo-5-fluoropyridine, 11.7 g (45 mmol) ethyl 1-tert.-butyloxycarbonylpiperidine-4-carboxylate, 416 mg (0.04 mmol) tris(dibenzylideneacetone)palladium(0), 0.91 mL tri-tert-butylphosphine (1M in toluene) and 60 ml toluene. To the dark red solution, 50 mL lithium-bis-(trimethylsilyl)-amid (1M in hexane) was added dropwise during 1 h at 18 to 23° C. The dark brown reaction solution was stirred for 87 h at room temperature. The reaction was quenched with saturated aqueous NH4Cl-solution. The aqueous layer was separated and extracted once with 200 mL ethyl acetate. The organic layers were washed once with 150 mL brine, dried over Na2SO4, filtered off and concentrated under vacuum. The residue was purified on silica eluting with a gradient formed from heptane and TBME to yield after evaporation of the product fractions 4 g (50%) of the title compound as yellow viscous oil. MS ISP (m/e): 253.3 (M-Boc)/353.2 [(M+H)+].

ii) 5-Fluoro-2',3',5',6'-tetrahydro-1'H-[2,4']bipyridinyl-4'-carboxylic acid ethyl ester, hydrochloride

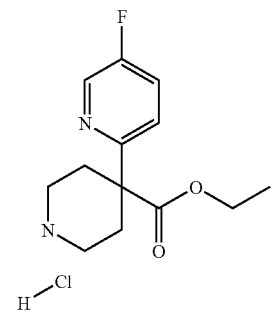

In analogy to the procedure described for the synthesis of 4-cyclopropylmethyl-piperidine-4-carboxylic acid ethyl ester, hydrochloride (intermediate 20, step i) the title compound was prepared from 5-fluoro-2',3',5',6'-tetrahydro-[2,4']bipyridinyl-1',4'-dicarboxylic acid 1'-tert-butyl ester 4'-ethyl ester through cleavage of the Boc-group with HCl in dioxane. MS ISP (m/e): 253.1 [(M+H)+].

iii) 5-Fluoro-1'-(4'-fluoro-biphenyl-4-carbonyl)-2',3', 5',6'-tetrahydro-1'H-[2,4']bipyridinyl-4'-carboxylic acid ethyl ester

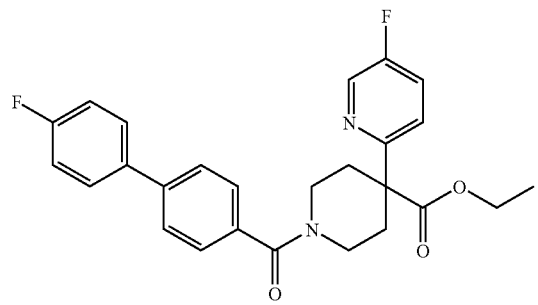

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 5-Fluoro-2',3',5',6'-tetrahydro-1'H-[2,4']bipyridinyl-4'-carboxylic acid ethyl ester, hydrochloride and 4'-fluoro-biphenyl-4-carboxylic acid (commercially available). MS ISP (m/e): 451.2 [(M+H)⁺].

iv) 5-Fluoro-1'-(4'-fluoro-biphenyl-4-carbonyl)-2',3',5',6'-tetrahydro-1'H-[2,4']bipyridinyl-4'-carboxylic acid

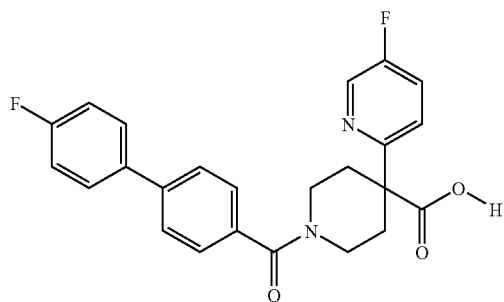

In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 5-Fluoro-F-(4'-fluoro-biphenyl-4-carbonyl)-2',3',5',6'-tetrahydro-1'H-[2,4']-bipyridinyl-4'-carboxylic acid ethyl ester through ester cleavage with LiOH.H$_2$O. MS ISP (m/e): 423.3 [(M+H)⁺].

Intermediate 25

1'-(4'-Fluoro-biphenyl-4-carbonyl)-6-tritluoromethyl-2',3',5',6'-tetrahydro-1'H-[3,4']bipyridinyl-4'-carboxylic acid

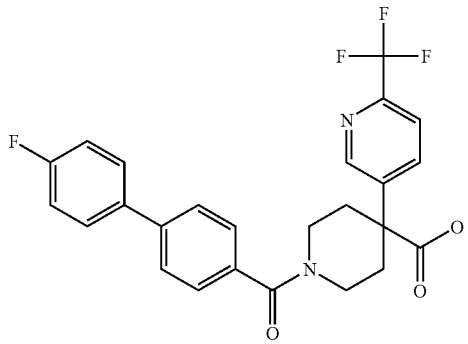

i) 6-Trifluoromethyl-2',3',5',6'-tetrahydro-[3,4']bipyridinyl-1',4'-dicarboxylic acid 1'-tert-butyl ester 4'-ethyl ester

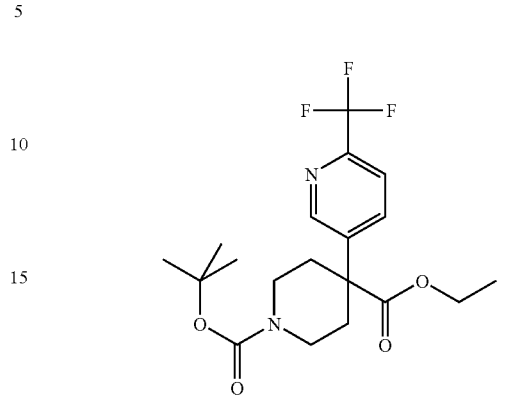

In analogy to the procedure described for the synthesis of 5-fluoro-2',3',5',6'-tetrahydro-[2,4']bipyridinyl-1',4'-dicarboxylic acid 1'-tert-butyl ester 4'-ethyl ester (intermediate 24, step i) the title compound was prepared from ethyl 1-tert.-butyloxycarbonylpiperidine-4-carboxylate and 5-bromo-2-(trifluoromethyl)pyridine. MS ISP (m/e): 403.2 [(M+H)⁺].

ii) 6-Trifluoromethyl-2',3',5',6'-tetrahydro-1'H-[3,4']bipyridinyl-4'-carboxylic acid ethyl ester, hydrochloride

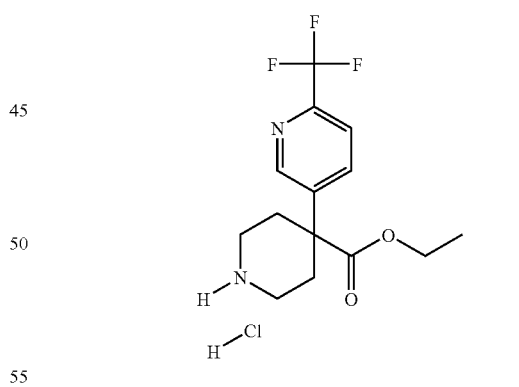

In analogy to the procedure described for the synthesis of 4-cyclopropylmethyl-piperidine-4-carboxylic acid ethyl ester, hydrochloride (intermediate 20, step i) the title compound was prepared from 6-trifluoromethyl-2',3',5',6'-tetrahydro-[3,4']bipyridinyl-1',4'-dicarboxylic acid 1'-tert-butyl ester 4'-ethyl ester through cleavage of the Boc-group with HCl in dioxane. MS ISP (m/e): 303.3 [(M+H)⁺].

iii) 1'-(4'-Fluoro-biphenyl-4-carbonyl)-6-trifluoromethyl-2',3',5',6'-tetrahydro-1'H-[3,4']bipyridinyl-4'-carboxylic acid ethyl ester

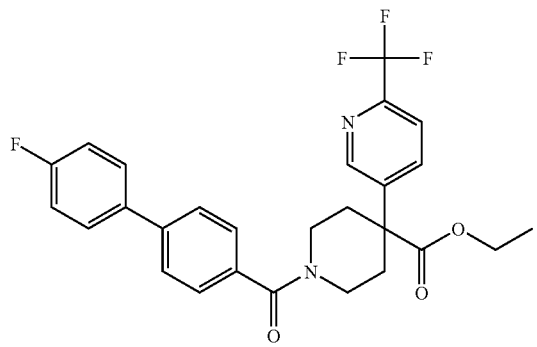

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 6-trifluoromethyl-2',3',5',6'-tetrahydro-1'H-[3,4']bipyridinyl-4'-carboxylic acid ethyl ester, hydrochloride and 4'-fluoro-biphenyl-4-carboxylic acid (commercially available). MS ISP (m/e): 501.1 [(M+H)⁺].

iv) 1'-(4'-Fluoro-biphenyl-4-carbonyl)-6-trifluoromethyl-2',3',5',6'-tetrahydro-1'H-[3,4']bipyridinyl-4'-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 1'-(4'-fluoro-biphenyl-4-carbonyl)-6-trifluoromethyl-2',3',5',6'-tetrahydro-1'H-[3,4']bipyridinyl-4'-carboxylic acid ethyl ester through ester cleavage with LiOH.H₂O. MS ISP (m/e): 473.1 [(M+H)⁺].

Intermediate 26

5-Fluoro-1'-[4-(5-methyl-[1,2,4]oxadiazol-3-yl)-benzoyl]-2',3',5',6'-tetrahydro-1'H-[2,4']bipyridinyl-4'-carboxylic acid

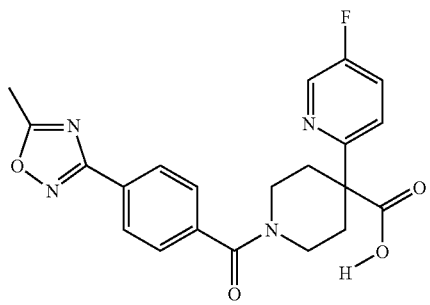

i) 5-Fluoro-1'-[4-(5-methyl-[1,2,4]oxadiazol-3-yl)-benzoyl]-2',3',5',6'-tetrahydro-1'H-[2,4']bipyridinyl-4'-carboxylic acid ethyl ester

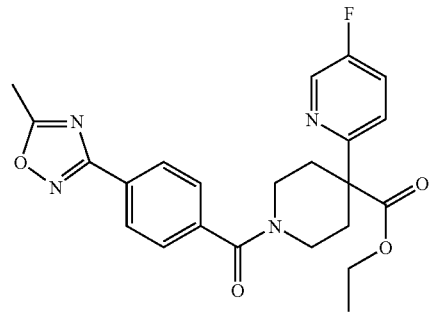

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 5-fluoro-2',3',5',6'-tetrahydro-1'H-[2,4']bipyridinyl-4'-carboxylic acid ethyl ester, hydrochloride and 4-(5-methyl-[1,2,4]oxadiazol-3-yl)-benzoic acid (commercially available). MS ISP (m/e): 439.3 [(M+H)⁺].

ii) 5-Fluoro-1'-[4-(5-methyl-[1,2,4]oxadiazol-3-yl)-benzoyl]-2',3',5',6'-tetrahydro-1'H-[2,4']bipyridinyl-4'-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 5-fluoro-1'-[4-(5-methyl-[1,2,4]oxadiazol-3-yl)-benzoyl]-2',3',5',6'-tetrahydro-1'H-[2,4']bipyridinyl-4'-carboxylic acid ethyl ester through ester cleavage with LiOH.H₂O. MS ISP (m/e): 411.2 [(M+H)⁺].

Intermediate 27

5-Fluoro-1'-[4-(3-methyl-[1,2,4]oxadiazol-5-yl)-benzoyl]-2',3',5',6'-tetrahydro-1'H-[2,4']bipyridinyl-4'-carboxylic acid

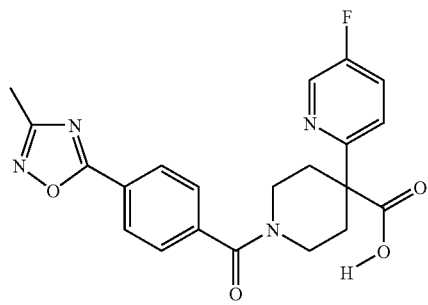

i) 5-Fluoro-1'-[4-(3-methyl-[1,2,4]oxadiazol-5-yl)-benzoyl]-2',3',5',6'-tetrahydro-1'H-[2,4']bipyridinyl-4'-carboxylic acid ethyl ester

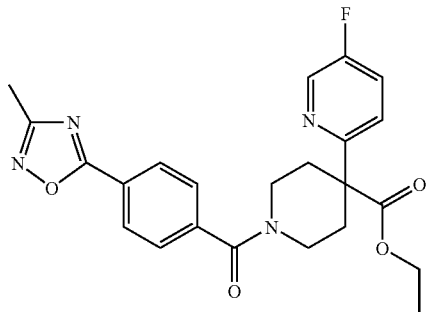

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 5-fluoro-2',3',5',6'-tetrahydro-1'H-[2,4']bipyridinyl-4'-carboxylic acid ethyl ester, hydrochloride and 4-(3-Methyl-[1,2,4]oxadiazol-5-yl)-benzoic acid (commercially available). MS ISP (m/e): 439.2 [(M+H)$^+$].

ii) 5-Fluoro-1'-[4-(3-methyl-[1,2,4]oxadiazol-5-yl)-benzoyl]-2',3',5',6'-tetrahydro-1'H-[2,4']bipyridinyl-4'-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 5-fluoro-1'-[4-(3-methyl-[1,2,4]oxadiazol-5-yl)-benzoyl]-2',3',5',6'-tetrahydro-1'H-[2,4']bipyridinyl-4'-carboxylic acid ethyl ester through ester cleavage with LiOH.H$_2$O. MS ISP (m/e): 411.2 [(M+H)$^+$].

Intermediate 28

1-(4'-Fluoro-biphenyl-4-carbonyl)-4-(4-fluoro-phenyl)-piperidine-4-carboxylic acid

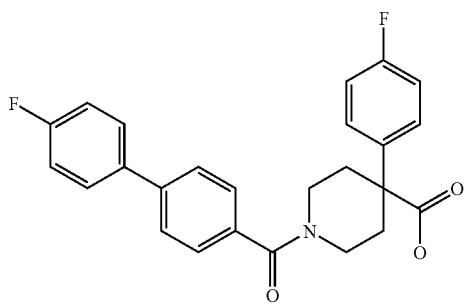

i) 1-(4'-Fluoro-biphenyl-4-carbonyl)-4-(4-fluoro-phenyl)-piperidine-4-carboxylic acid ethyl ester

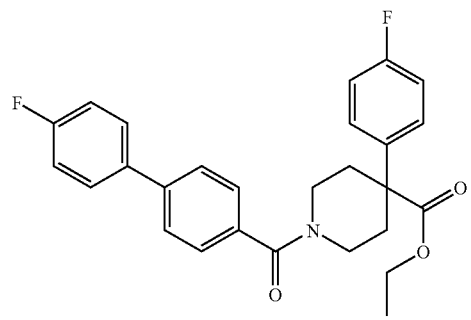

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 4-(4-fluoro-phenyl)-piperidine-4-carboxylic acid ethyl ester (WO2000071517) and 4'-fluoro-biphenyl-4-carboxylic acid (commercially available). MS ISP (m/e): 450.2 [(M+H)$^+$].

ii) 1-(4'-Fluoro-biphenyl-4-carbonyl)-4-(4-fluoro-phenyl)-piperidine-4-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 1-(4'-Fluoro-biphenyl-4-carbonyl)-4-(4-fluoro-phenyl)-piperidine-4-carboxylic acid ethyl ester through ester cleavage with LiOH.H$_2$O. MS ISP (m/e): 422.1 [(M+H)$^+$].

Intermediate 29

1-(5'-Cyano-3,4,5,6-tetrahydro-2H-[1,2']bipyridinyl-4-carbonyl)-4-(4-fluoro-phenyl)-piperidine-4-carboxylic acid

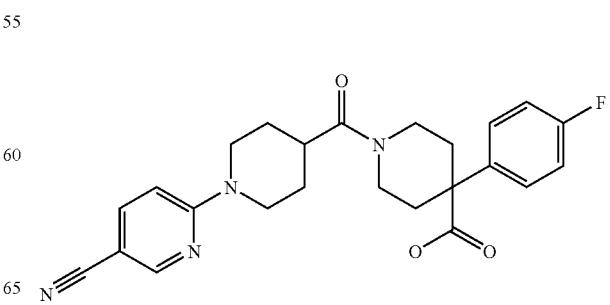

91 i) 1-(5'-Cyano-3,4,5,6-tetrahydro-2H-[1,2']bipyridinyl-4-carbonyl)-4-(4-fluoro-phenyl)-piperidine-4-carboxylic acid ethyl ester

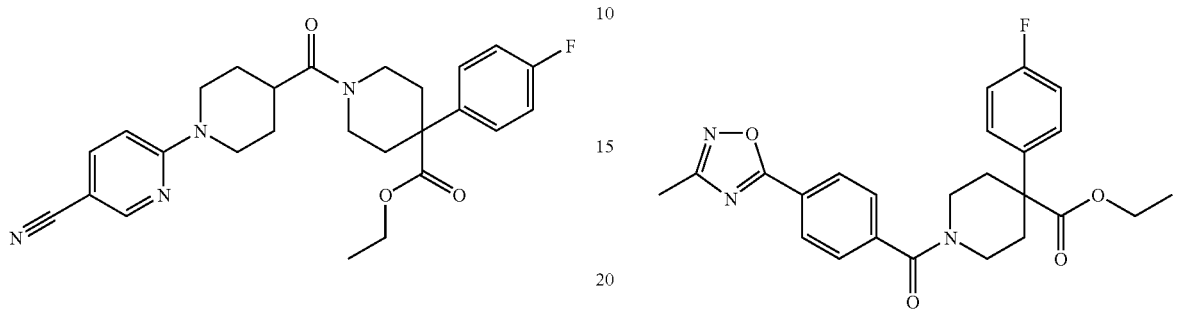

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 4-(4-fluoro-phenyl)-piperidine-4-carboxylic acid ethyl ester (WO2000071517) and 5'-Cyano-3,4,5,6-tetrahydro-2H-[1,2']bipyridinyl-4-carboxylic acid (commercially available). MS ISP (m/e): 465.2 [(M+H)$^+$].

ii) 1-(5'-Cyano-3,4,5,6-tetrahydro-2H-[1,2]bipyridinyl-4-carbonyl)-4-(4-fluoro-phenyl)-piperidine-4-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 1-(5'-Cyano-3,4,5,6-tetrahydro-2H-[1,2']-bipyridinyl-4-carbonyl)-4-(4-fluoro-phenyl)-piperidine-4-carboxylic acid ethyl ester through ester cleavage with LiOH.H$_2$O. MS ISP (m/e): 435.5 [(M+H)$^+$].

Intermediate 30

4-(4-Fluoro-phenyl)-1-[4-(3-methyl-[1,2,4]oxadiazol-5-yl)-benzoyl]-piperidine-4-carboxylic acid

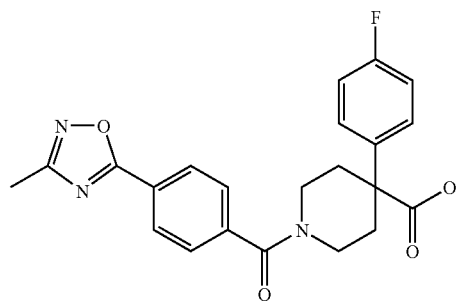

92 i) 4-(4-Fluoro-phenyl)-1-[4-(3-methyl-[1,2,4]oxadiazol-5-yl)-benzoyl]-piperidine-4-carboxylic acid ethyl ester In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 4-(4-fluoro-phenyl)-piperidine-4-carboxylic acid ethyl ester (WO2000071517) and 4-(3-methyl-1,2,4-oxadiazol-5-yl) benzoic acid (commercially available). MS ISP (m/e): 438.2 [(M+H)$^+$].

ii) 4-(4-Fluoro-phenyl)-1-[4-(3-methyl-[1,2,4]oxadiazol-5-yl)-benzoyl]-piperidine-4-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 4-(4-fluoro-phenyl)-1-[4-(3-methyl-[1,2,4]oxadiazol-5-yl)-benzoyl]-piperidine-4-carboxylic acid ethyl ester through ester cleavage with LiOH.H$_2$O. MS ISP (m/e): 410.2 [(M+H)$^+$].

Intermediate 31

4-(4-Fluoro-phenyl)-1-[4-(5-methyl-[1,2,4]oxadiazol-3-yl)-benzoyl]-piperidine-4-carboxylic acid

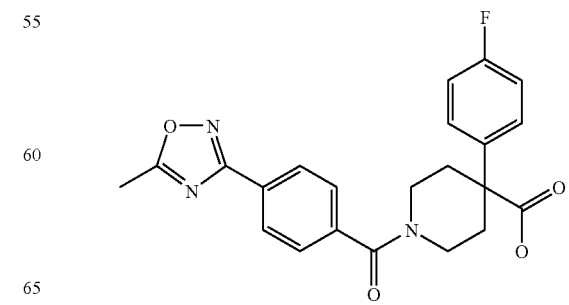

i) 4-(4-Fluoro-phenyl)-1-[4-(5-methyl-[1,2,4]oxadiazol-3-yl)-benzoyl]-piperidine-4-carboxylic acid ethyl ester

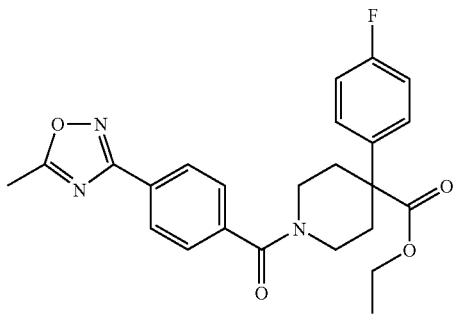

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 4-(4-fluoro-phenyl)-piperidine-4-carboxylic acid ethyl ester (WO2000071517) and 4-(5-methyl-1,2,4-oxadiazol-3-yl) benzoic acid (commercially available). MS ISP (m/e): 438.2 [(M+H)$^+$].

ii) 4-(4-Fluoro-phenyl)-1-[4-(5-methyl-[1,2,4]oxadiazol-3-yl)-benzoyl]-piperidine-4-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 4-(4-fluoro-phenyl)-1-[4-(3-methyl-[1,2,4]oxadiazol-5-yl)-benzoyl]-piperidine-4-carboxylic acid ethyl ester through ester cleavage with LiOH.H$_2$O. MS ISN (m/e): 408.4 (M−H).

Intermediate 32

4-(4-Fluoro-phenyl)-1-[4-(2-oxo-piperidin-1-yl)-benzoyl]-piperidine-4-carboxylic acid

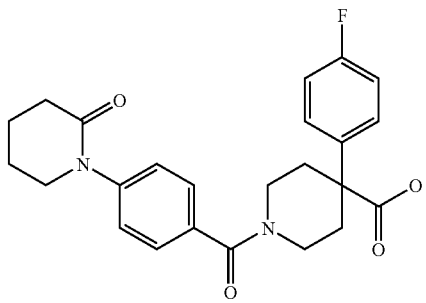

i) 4-(4-Fluoro-phenyl)-1-[4-(2-oxo-piperidin-1-yl)-benzoyl]-piperidine-4-carboxylic acid ethyl ester

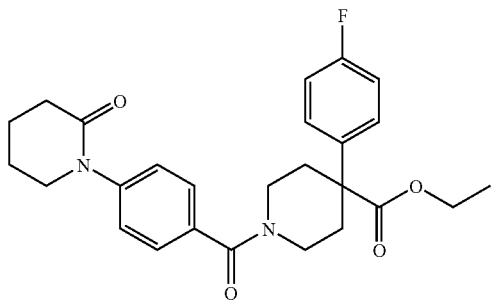

In analogy to the procedure described for the synthesis of 4-cyclopropylmethyl-1-(4'-fluoro-biphenyl-4-carbonyl)-piperidine-4-carboxylic acid ethyl ester (intermediate 20, step ii) the title compound was prepared from 4-(4-fluoro-phenyl)-piperidine-4-carboxylic acid ethyl ester (WO2000071517) and 4-(2-Oxo-piperidin-1-yl)benzoic acid (commercially available). MS ISP (m/e): 453.2 [(M+H)$^+$].

ii) 4-(4-Fluoro-phenyl)-1-[4-(2-oxo-piperidin-1-yl)-benzoyl]-piperidine-4-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 4-(4-Fluoro-phenyl)-1-[4-(2-oxo-piperidin-1-yl)-benzoyl]-piperidine-4-carboxylic acid ethyl ester through ester cleavage with LiOH.H$_2$O. MS ISN (m/e): 423.4 (M−H).

Intermediate 33

4-(4-Fluoro-phenyl)-1-[4-(4-fluoro-phenyl)-piperazine-1-carbonyl]-piperidine-4-carboxylic acid

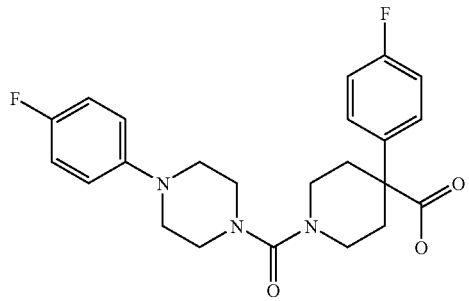

i) 4-(4-Fluoro-phenyl)-1-[4-(4-fluoro-phenyl)-piperazine-1-carbonyl]-piperidine-4-carboxylic acid ethyl ester

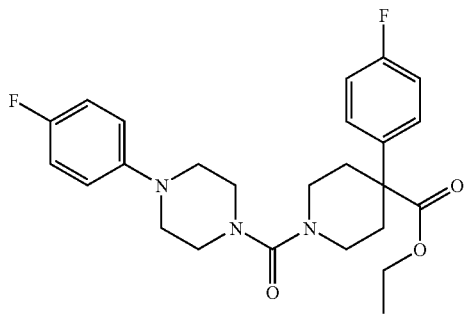

Under inert conditions a 100 mL four necked flask with a magnetic stirrer bar was charged with 0.89 g (5.5 mmol) of CDI in 10 mL MeCN. At 0-5° C. a solution of 0.99 g (5.5 mmol) 1-(4-fluorophenyl)piperazine in 10 mL MeCN was added drop wise during 15 min. The light yellow solution was stirred for 15 min at 0-5° C. and 3 h at 20° C. After 90 min an additional 70 mg CDI was added. 1.2 g (4.8 mmol) 4-(4-fluoro-phenyl)-piperidine-4-carboxylic acid ethyl ester (WO2000071517) in 5 ml MeCN was added. The mixture was heated for in total 5 days to reflux. The reaction mixture was concentrated under vacuum. The residue was dissolved in 15 ml N,N-dimethylacetamide and heated twice for 30 min at 200° C. under micro wave irradiations. The dark brown reaction solution was concentrated under high vacuum. The residue was taken up between 100 mL water and 100 mL ethyl acetate and extracted. The aqueous layers were extracted once with 100 mL ethyl acetate and the organic layers were washed once with 100 mL brine, dried over $Na_2SO_4$, filtered off, concentrated under vacuum and purified through column chromatography over silica eluting with a gradient formed from i-propanol and heptane. The product containing fractions were evaporated to yield 0.65 g (29%) of the title compound as light yellow viscous oil. MS ISP (m/e): 458.3 [(M+H)$^+$].

ii) 4-(4-Fluoro-phenyl)-1-[4-(4-fluoro-phenyl)-piperazine-1-carbonyl]-piperidine-4-carboxylic acid In analogy to the procedure described for the synthesis of 4-cyclopropylmethyl-1-(4'-fluoro-biphenyl-4-carbonyl)-piperidine-4-carboxylic acid (intermediate 20, step iii) the title compound was prepared from 4-(4-Fluoro-phenyl)-1-[4-(2-oxo-piperidin-1-yl)-benzoyl]-piperidine-4-carboxylic acid ethyl ester through ester cleavage with LiOH.H$_2$O. MS ISP (m/e): 430.3 [(M+H)$^+$].

Example 114

1-[4-(3-Methyl-[1,2,4]oxadiazol-5-yl)-benzoyl]-4-phenyl-piperidine-4-carboxylic acid [(S)-1-(4-trifluoromethyl-phenyl)-ethyl]-amide

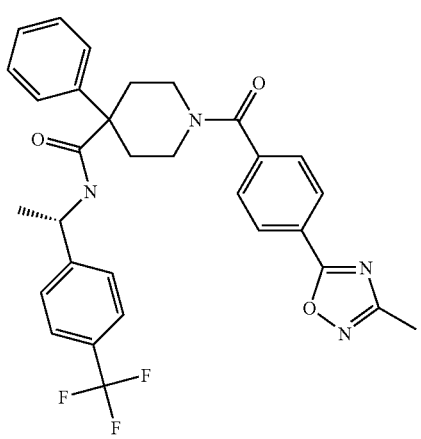

To a mixture of 1-[4-(3-methyl-[1,2,4]oxadiazol-5-yl)-benzoyl]-4-phenyl-piperidine-4-carboxylic acid (105 mg, purity ~48%, 0.128 mmol), EDC (39 mg, 0.205 mmol), HOBT (31 mg, 0.205 mmol) and triethylamine (66 pt, 0.473 mmol) in dichloromethane (2 mL) at room temperature was added slowly a solution of (S)-[4-(trifluoromethyl)phenyl]ethylamine (29 mg, 0.154 mmol) in dichloromethane (1 mL). The reaction mixture was stirred at room temperature for 12 h. The reaction mixture was subjected to flash chromatography with n-heptane and ethyl acetate over a 10 g silica gel column to yield 23 mg 1-[4-(3-methyl-[1,2,4]oxadiazol-5-yl)-benzoyl]-4-phenyl-piperidine-4-carboxylic acid [(S)-1-(4-trifluoromethyl-phenyl)-ethyl]-amide. MS ISP (m/e): 563.3 [(M+H)$^+$].

In analogy to the procedure described for the synthesis of 1-[4-(3-Methyl-[1,2,4]oxadiazol-5-yl)-benzoyl]-4-phenyl-piperidine-4-carboxylic acid [(S)-1-(4-trifluoromethyl-phenyl)-ethyl]-amide (example 114) further piperidine derivatives have been synthesized from their respective starting materials as mentioned in table 3. Table 3 comprises example 115-example 200.

TABLE 3

| No | structure | MW calc. | systematic Name | starting materials | MW (MH+) |
|---|---|---|---|---|---|
| 115 | 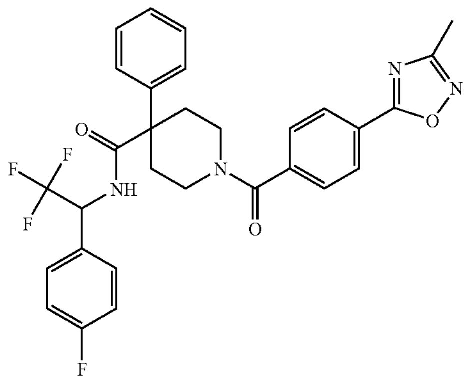 | 566.552 | rac-1-[4-(3-Methyl-[1,2,4]oxadiazol-5-yl)-benzoyl]-4-phenyl-piperirdine-4-carboxylic acid [2,2,2-trifluoro-1-(4-fluoro-phenyl)-ethyl]-amide | 1-[4-(3-Methyl-[1,2,4]oxadiazol-5-yl)-benzoyl]-4-phenyl-piperidine-4-carboxylic acid (intermediate 19) and 2,2,2-trifluoro-1-(4-fluoro-phenyl)-ethylamine (commercially available) | 567 |
| 116 | 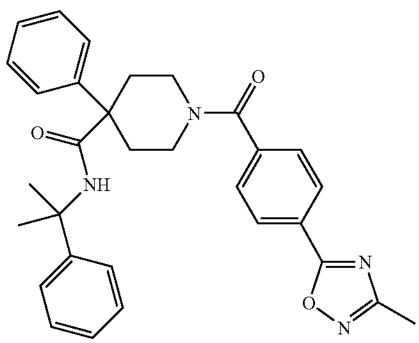 | 508.619 | 1-[4-(3-Methyl-[1,2,4]oxadiazol-5-yl)-benzoyl]-4-phenyl-piperidine-4-carboxylic acid (1-methyl-1-phenyl-ethyl)-amide | 1-[4-(3-Methyl-[1,2,4]oxadiazol-5-yl)-benzoyl]-4-phenyl-piperidine-4-carboxylic acid (intermediae 19) and 1-methyl-1-phenyl-ethylamine (commercially available) | 509.3 |
| 117 | 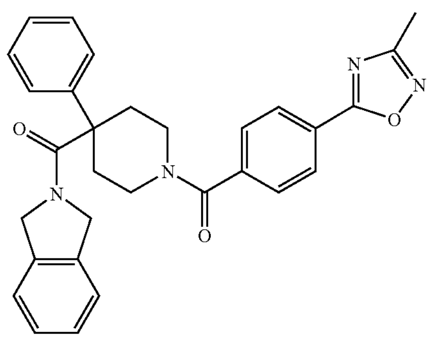 | 492.576 | (1,3-Dihydro-isoindol-2-yl)-{1-[4-(3-methyl-[1,2,4]oxadiazol-5-yl)-benzoyl]-4-phenyl-piperidine-4-yl}-methanone | 1-[4-(3-Methyl-[1,2,4]oxadiazol-5-yl)-benzoyl]-4-phenyl-piperidine-4-carboxylic acid (intermediate 19) and 2,3-dihydro-1H-isoindole (commercially available) | 493.3 |
| 118 | 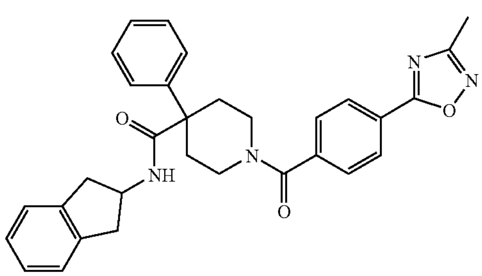 | 506.603 | 1-[4-(3-Methyl-[1,2,4]oxadiazol-5-yl)-benzoyl]-4-phenyl-piperidine-4-carboxylic acid indan-2-ylamide | 1-[4-(3-Methyl-[1,2,4]oxadiazol-5-yl)-benzoyl]-4-phenyl-piperidine-4-carboxylic acid (intermediate 19) and indan-2-ylamine (commercially available) | 507.2 |
| 119 | 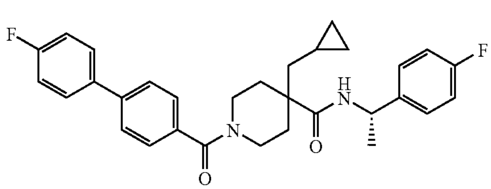 | 506.602 | 4-Cyclopropylmethyl-1-(4'-fluoro-biphenyl-4-carbonyl)-piperidine-4-carboxylic acid [(S)-1-(4-fluoro-phenyl)-ethyl]-amide | 4-Cyclopropylmethyl-1-(4'-fluoro-biphenyl-4-carbonyl)-piperidine-4-carboxylic acid (intermediate 20) and (S)-1-(4-fluoro-phenyl)-ethylamine (commercially available) | 503.2 |

TABLE 3-continued

| No | structure | MW calc. | systematic Name | starting materials | MW (MH+) |
|---|---|---|---|---|---|
| 120 | 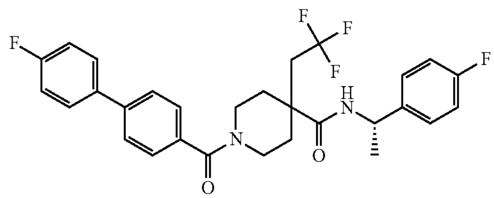 | 530.534 | 1-(4'-Fluoro-biphenyl-4-carbonyl)-4-(2,2,2-trifluoro-ethyl)-piperidine-4-carboxylic acid [(S)-1-(4-fluoro-phenyl)-ethyl]-amide | 1-(4'-Fluoro-biphenyl-4-carbonyl)-4-(2,2,2-trifluoro-ethyl)-piperidine-4-carboxylic acid (intermediate 21) and (S)-1-(4-fluoro-phenyl)-ethylamine (commercially available) | 531.2 |
| 121 | 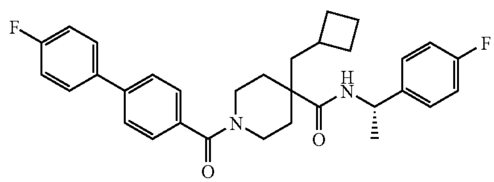 | 516.629 | 4-Cyclobutylmethyl-1-(4'-fluoro-biphenyl-4-carbonyl)-piperidine-4-carboxylic acid [(S)-1-(4-fluoro-phenyl)-ethyl]-amide | 4-Cyclobutylmethyl-1-(4'-fluoro-biphenyl-4-carbonyl)-piperidine-4-carboxylic acid (intermediate 22) and (S)-1-(4-fluoro-phenyl)-ethylamine (commercially available) | 517.4 |
| 122 | 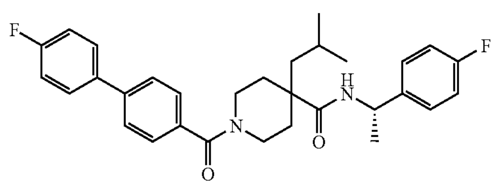 | 504.618 | 1-(4'-Fluoro-biphenyl-4-carbonyl)-4-isobutyl-piperidine-4-carboxylic acid [(S)-1-(4-fluoro-phenyl)-ethyl]-amide | 1-(4'-Fluoro-biphenyl-4-carbonyl)-4-isobutyl-piperidine-4-carboxylic acid (intermediate 23) and (S)-1-(4-fluoro-phenyl)-ethylamine (commercially available) | 505.3 |
| 123 | 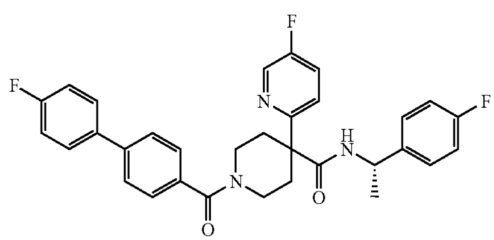 | 543.586 | 5-Fluoro-1'-(4'-fluoro-biphenyl-4-carbonyl)-2',3',5',6'-tetrahydro-1'H-[2,4']bipyridinyl-4'-carboxylic acid [(S)-1-(4-fluoro-phenyl)-ethyl]-amide | 5-Fluoro-1'-(4'-fluoro-biphenyl-4-carbonyl)-2',3',5',6'-tetrahydro-1'H-[2,4']bipyridinyl-4'-carboxylic acid (intermediate 24) and (S)-1-(4-fluoro-phenyl)-ethylamine (commercially available) | 544.2 |
| 124 | 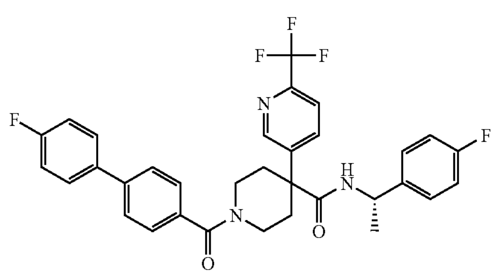 | 593.593 | 1'-(4'-Fluoro-biphenyl-4-carbonyl)-6-trifluoromethyl-2',3',4',5',6'-tetrahydro-1'H-[3,4']bipyridinyl-4'-carboxylic acid [(S)-1-(4-fluoro-phenyl)-ethyl]-amide | 1'-(4'-Fluoro-biphenyl-4-carbonyl)-6-trifluoromethyl-2',3',5',6'-tetrahydro-1'H-[3,4']bipyridinyl-4'-carboxylic acid (intermediate 25) and (S)-1-(4-fluoro-phenyl)-ethylamine (commerically available) | 594.2 |
| 125 | 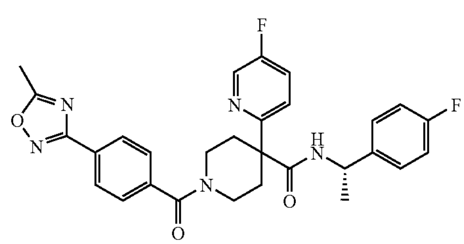 | 531.56 | 5-Fluoro-1'-[4-(5-methyl-[1,2,4]oxadiazol-3-yl)-benzoyl]-2',3',5',6'-tetrahydro-1'H-[2,4']bipyridinyl-4'-carboxylic acid [(S)-1-(4-fluoro-phenyl)-ethyl]-amide | 5-Fluoro-1'-[4-(5-methyl-[1,2,4]oxadiazol-3-yl)-benzoyl]-2',3',5',6'-tetrahydro-1'H-[2,4']bipyridinyl-4'-carboxylic acid (intermediate 26) and (S)-1-(4-fluoro-phenyl)-ethylamine (commericially available) | 282.2/ 532.1 |

TABLE 3-continued

| No | structure | MW calc. | systematic Name | starting materials | MW (MH+) |
|---|---|---|---|---|---|
| 126 | 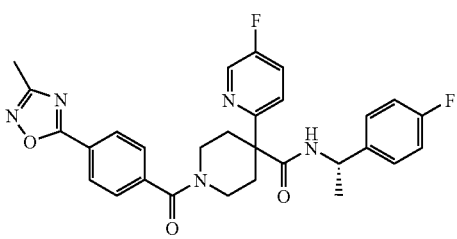 | 531.56 | 5-Fluoro-1'-[4-(3-methyl-[1,2,4]oxadiazol-5-yl)-benzoyl]-2',3',5',6'-tetrahydro-1'H-[2,4']bipyridinyl-4'-carboxylic acid [(S)-1-(4-fluoro-phenyl)-ethyl]-amide | 5-Fluoro-1'-[4-(3-methyl-[1,2,4]oxadiazol-5-yl)-benzoyl]-2',3',5',6'-tetrahydro-1'H-[2,4']bipyridinyl-4'-carboxylic acid (intermediate 27) and (S)-1-(4-fluoro-phenyl)-ethylamine (commerically available) | 238.2/ 532.2 |
| 127 | 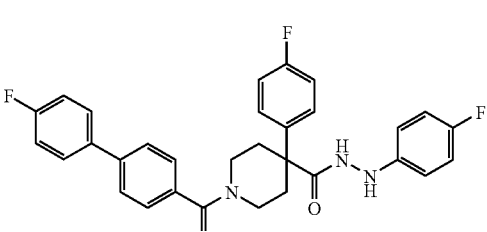 | 529.56 | 1-(4'-Fluoro-biphenyl-4-carbonyl)-4-(4-fluoro-phenyl)-piperidine-4-carboxylic acid N'-(4-fluoro-phenyl)-hydrazide | 1-(4'-Fluoro-biphenyl-4-carbonyl)-4-(4-fluoro-phenyl)-piperidine-4-carboxylic acid (intermeidate 28) and (4-Fluoro-phenyl)-hydrazine (commercially available) | 530.2 |
| 128 | 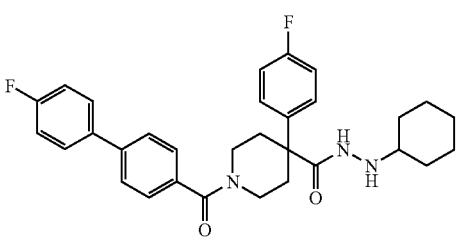 | 517.62 | 1-(4'-Fluoro-biphenyl-4-carbonyl)-4-(4-fluoro-phenyl)-piperidine-4-carboxylic acid N'-cyclohexyl-hydrazide | 1-(4'-Fluoro-biphenyl-4-carbonyl)-4-(4-fluoro-phenyl)-piperidine-4-carboxylic acid (intermediate 28) and cyclohexyl-hydrazine (commercially available) | 518.3 |
| 129 | 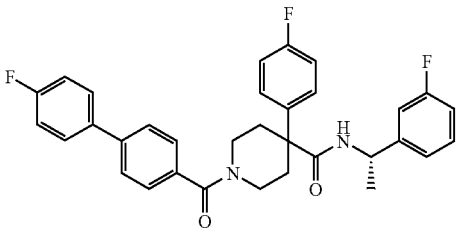 | 542.6 | 1-(4'-Fluoro-biphenyl-4-carbonyl)-4-(4-fluoro-phenyl)-piperidine-4-carboxylic acid [(S)-1-(3-fluoro-phenyl)-ethyl]-amide | 1-(4'-Fluoro-biphenyl-4-carbonyl)-4-(4-fluoro-phenyl)-piperidine-4-carboxylic acid (intermediate 28) and (S)-1-(3-fluoro-phenyl)-ethylamine (commercially available) | 543.3 |
| 130 | 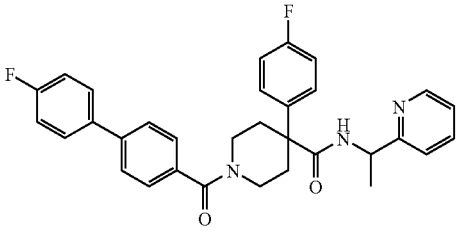 | 525.6 | 1-(4'-Fluoro-biphenyl-4-carbonyl)-4-(4-fluoro-phenyl)-piperidine-4-carboxylic acid (1-pyridin-2-yl-ethyl)-amide | 1-(4'-Fluoro-biphenyl-4-carbonyl)-4-(4-fluoro-phenyl)-piperidine-4-carboxylic acid (intermediate 28) and 1-pyridin-2-yl-ethylamine (commercially available) | 526.1 |
| 131 | 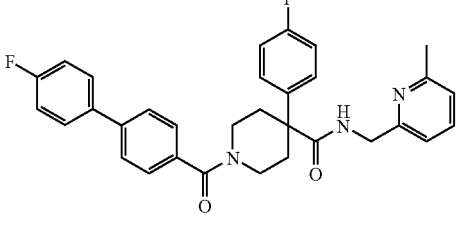 | 525.6 | 1-(4'-Fluoro-biphenyl-4-carbonyl)-4-(4-fluorophenyl)-piperidine-4-carboxylic acid (6-methyl-pyridin-2-ylmethyl)-amide | 1-(4'-Fluoro-biphenyl-4-carbonyl)-4-(4-fluoro-phenyl)-piperidine-4-carboxylic acid (intermediate 28) and C-(6-methyl-pyridin-2-yl)-methylamine (commercially available) | 526.1 |

TABLE 3-continued

| No | structure | MW calc. | systematic Name | starting materials | MW (MH+) |
|---|---|---|---|---|---|
| 132 | 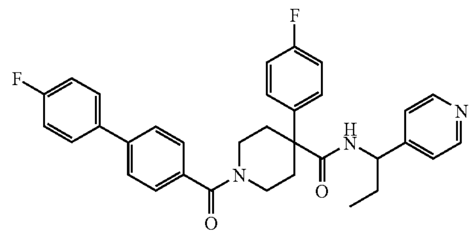 | 539.63 | 1-(4'-Fluoro-biphenyl-4-carbonyl)-4-(4-fluoro-phenyl)-piperidine-4-carboxylic acid (1-pyridin-4-yl-propyl)-amide | 1-(4'-Fluoro-biphenyl-4-carbonyl)-4-(4-fluoro-phenyl)-piperidine-4-carboxylic acid (intermeidate 28) and 1-pyridin-4-yl-propylamine (commercially available) | 540.3 |
| 133 | 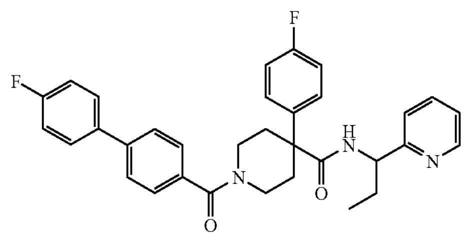 | 539.63 | 1-(4'-Fluoro-biphenyl-4-carbonyl)-4-(4-fluoro-phenyl)-piperidine-4-carboxylic acid (1-pyridin-2-yl-propyl)-amide | 1-(4'-Fluoro-biphenyl-4-carbonyl)-4-(4-fluoro-phenyl)-piperidne-4-carboxylic acid (intermediate 28) and 1-pyridin-2-yl-propylamine (commercially available) | 540.2 |
| 134 | 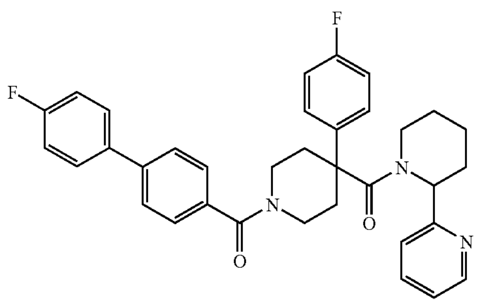 | 565.66 | (4'-Fluoro-biphenyl-4-yl)-[4-(4-fluoro-phenyl)-4-(3,4,5,6-tetrahydro-2H-[2,2']bipyridinyl-1-carbonyl)-piperidin-1-yl]-methanone | 1-(4'-Fluoro-biphenyl-4-carbonyl)-4-(4-fluoro-phenyl)-piperidine-4-carboxylic acid (intermediate 28) and 1,2,3,4,5,6-Hexahydro-[2,2']bipyridinyl (commercially available) | 566.3 |
| 135 | 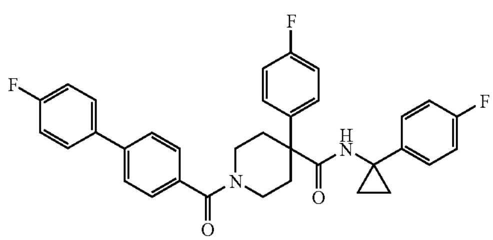 | 554.61 | 1-(4'-Fluoro-biphenyl-4-carbonyl)-4-(4-fluoro-phenyl)-piperidine-4-carboxylic acid [1-(4-fluoro-phenyl)-cyclopropyl]-amide | 1-(4'-Fluoro-biphenyl-4-carbonyl)-4-(4-fluoro-phenyl)-piperidine-4-carboxylic acid (intermediate 28) and 1-(4-fluoro-phenyl)-cyclopropylamine (commercially available) | 555.1 |
| 136 | 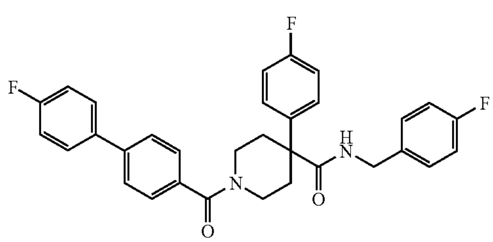 | 528.57 | 1-(4'-Fluoro-biphenyl-4-carbonyl)-4-(4-fluoro-phenyl)-piperidine-4-carboxylic acid 4-fluoro-benzylamide | 1-(4'-Fluoro-biphenyl-4-carbonyl)-4-(4-fluoro-phenyl)-piperdine-4-carboxylic acid (intermediate 28) and 4-fluoro-benzylamine (commercially available) | 529.2 |
| 137 | 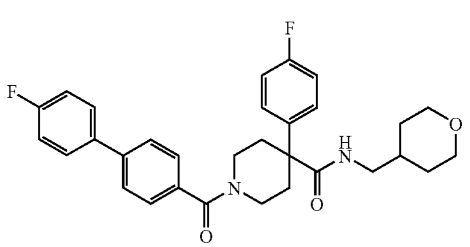 | 518.6 | 1-(4'-Fluoro-biphenyl-4-carbonyl)-4-(4-fluoro-phenyl)-piperidine-4-carboxylic acid (tetrahydro-pyran-4-ylmethyl)-amide | 1-(4'-Fluoro-biphenyl-4-carbonyl)-4-(4-fluoro-phenyl)-piperidine-4-carboxylic acid (intermediate 28) and C-(tetrahydro-pyran-4-yl)-methylamine (commercially available) | 519.3 |

TABLE 3-continued

| No | structure | MW calc. | systematic Name | starting materials | MW (MH+) |
|---|---|---|---|---|---|
| 138 | 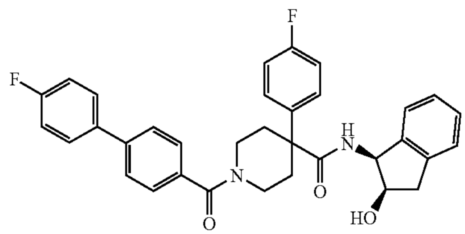 | 552.62 | 1-(4'-Fluoro-biphenyl-4-carbonyl)-4-(4-fluoro-phenyl)-piperidine-4-carboxylic acid ((1S,2R)-2-hydroxy-indan-1-yl)-amide | 1-(4'-Fluoro-biphenyl-4-carbonyl)-4-(4-fluoro-phenyl)-piperidine-4-carboxylic acid (intermediate 28) and (1S,2R)-1-amino-indan-2-ol (commercially available) | 553.2 |
| 139 | 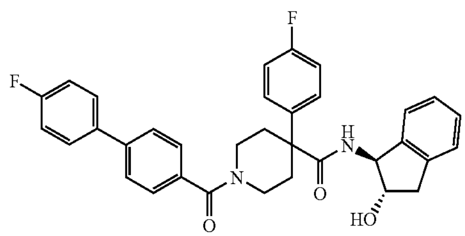 | 552.62 | 1-(4'-Fluoro-biphenyl-4-carbonyl)-4-(4-fluoro-phenyl)-piperidine-4-carboxylic acid ((1S,2S)-2-hydroxy-indan-1-yl)-amide | 1-(4'-Fluoro-biphenyl-4-carbonyl)-4-(4-fluoro-phenyl)-piperidine-4-carboxylic acid (intermediate 28) and (1S,2S)-1-amino-indan-2-ol (commercially avaialable) | 553.2 |
| 140 | 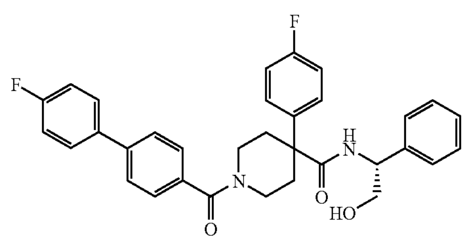 | 540.61 | 1-(4'-Fluoro-biphenyl-4-carbonyl)-4-(4-fluoro-phenyl)-piperidine-4-carboxylic acid ((R)-2-hydroxy-1-phenyl-ethyl)-amide | 1-(4'-Fluoro-biphenyl-4-carbonyl)-4-(4-fluoro-phenyl)-piperidine-4-carboxylic acid (intermediate 28) and (R)-2-amino-2-phenyl-ethanol (commercially available) | 541.2 |
| 141 | 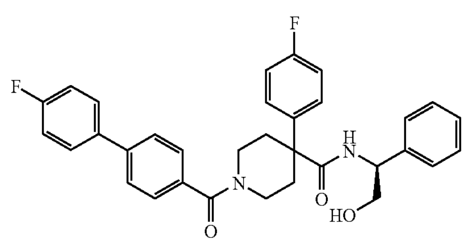 | 540.61 | 1-(4'-Fluoro-biphenyl-4-carbonyl)-4-(4-fluoro-phenyl)-piperidine-4-carboxylic acid ((S)-2-hydroxy-1-phenyl-ethyl)-amide | 1-(4'-Fluoro-biphenyl-4-carbonyl)-4-(4-fluoro-phenyl)-piperidine-4-carboxylic acid (intermediate 28) and (S)-2-amine-2-phenyl-ethanol (commercially available) | 541.2 |
| 142 | 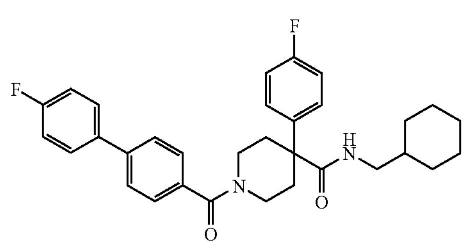 | 516.63 | 1-(4'-Fluoro-biphenyl-4-carbonyl)-4-(4-fluoro-phenyl)-piperidine-4-carboxylic acid cyclohexylmethyl-amide | 1-(4'-Fluoro-biphenyl-4-carbonyl)-4-(4-fluoro-phenyl)-piperidine-4-carboxylic acid (intermediate 28) and C-cyclohexyl-methylamine (commercially avaialble) | 517.3 |
| 143 | 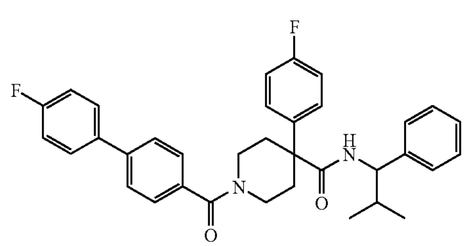 | 552.66 | 1-(4'-Fluoro-biphenyl-4-carbonyl)-4-(4-fluoro-phenyl)-piperidine-4-carboxylic acid (2-methyl-1-phenyl-propyl)-amide | 1-(4'-Fluoro-biphenyl-4-carbonyl)-4-(4-fluoro-phenyl)-piperidine-4-carboxylic acid (intermediate 28) and | 553.2 |

TABLE 3-continued

| No | structure | MW calc. | systematic Name | starting materials | MW (MH+) |
|---|---|---|---|---|---|
| 144 | 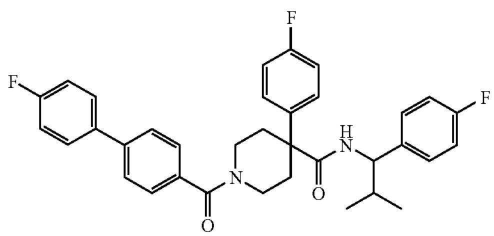 | 570.65 | 1-(4'-Fluoro-biphenyl-carbonyl)-4-(4-fluoro-phenyl)-piperidne-4-carboxylic acid [1-(4-fluoro-phenyl)-2-methyl-propyl]-amide | 1-(4'-Fluoro-biphenyl-4-carbonyl)-4-(4-fluoro-phenyl)-piperidine-4-carboxylic acid (intermediate 28) and 2-methyl-1-phenyl-propylamine (commercially available) | 571.2 |
| 145 | 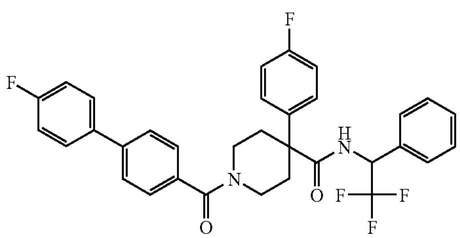 | 578.58 | 1-(4'-Fluoro-biphenyl-4-carbonyl)-4-(4-fluoro-phenyl)-piperidine-4-carboxylic acid (2,2,2-trifluoro-1-phenyl-ethyl)-amide | 1-(4'-Fluoro-biphenyl-4-carbonyl)-4-(4-fluoro-phenyl)-piperidne-4-carboxylic acid (intermediate 28) and 2,2,2-trifluoro-1-phenyl-ethylamine (commercially available) | 579.2 |
| 146 | 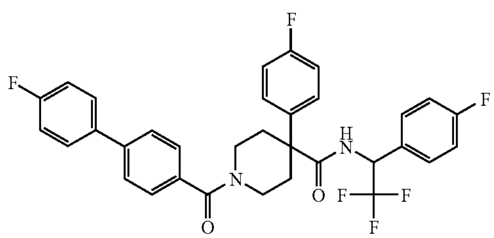 | 596.57 | 1-(4'-Fluoro-biphenyl-4-carbonyl)-4-(4-fluoro-phenyl)-piperidine-4-carboxylic acid [2,2,2-trifluoro-1-(4-fluoro-phenyl)-ethyl]-amide | 1-(4'-Fluoro-biphenyl-4-carbonyl)-4-(4-fluoro-phenyl)-piperidine-4-carboxylic acid (intermediate 28) and 2,2,2-trifluoro-1-(4-fluoro-phenyl)-ethylamine (commercially available) | 597.2 |
| 147 | 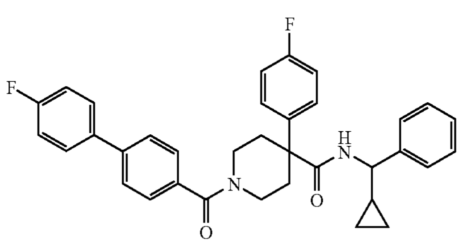 | 550.65 | 1-(4'-Fluoro-biphenyl-4-carbonyl)-4-(4-fluoro-phenyl)-piperidine-4-carboxylic acid (cyclopropyl-phenyl-methyl)-amide | 1-(4'-Fluoro-biphenyl-4-carbonyl)-4-(4-fluoro-phenyl)-piperidine-4-carboxylic acid (intermediate 28) and C-cyclopropyl-C-phenyl-methylamine (commercially available) | 551.3 |
| 148 | 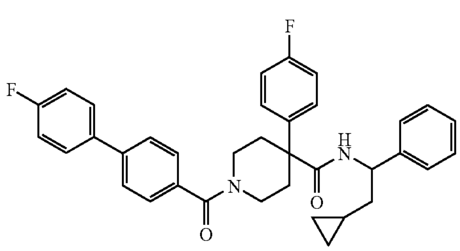 | 564.68 | 1-(4'-Fluoro-biphenyl-4-carbonyl)-4-(4-fluoro-phenyl)-piperidine-4-carboxylic acid (2-cyclopropyl-1-phenyl-ethyl)-amide | 1-(4'-Fluoro-biphenyl-4-carbonyl)-4-(4-fluoro-phenyl)-piperidine-4-carboxylic acid (intermediate 28) and 2-cyclopropyl-1-phenyl-ethylamine (commercially available) | 565.3 |
| 149 | 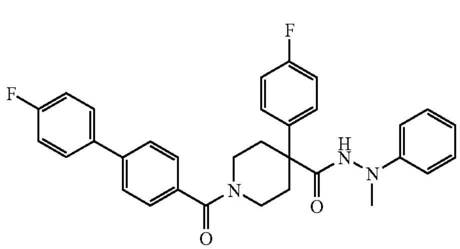 | 525.596 | 1-(4'-Fluoro-biphenyl-4-carbonyl)-4-(4-fluoro-phenyl)-piperidine-4-carboxylic acid N'-methyl-N'-phenyl-hydrazide | 1-(4'-Fluoro-biphenyl-4-carbonyl)-4-(4-fluoro-phenyl)-piperidine-4-carboxylic acid (intermediate 28) and N-methyl-N-phenyl-hydrazine (commercially available) | 526.3 |

| No | structure | MW calc. | systematic Name | starting materials | MW (MH+) |
|---|---|---|---|---|---|
| 150 | 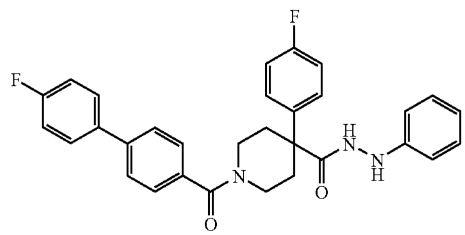 | 511.569 | 1-(4'-Fluoro-biphenyl-4-carbonyl)-4-(4-fluoro-phenyl)-piperidine-4-carboxylic acid N'-phenyl-hydrazide | 1-(4'-Fluoro-biphenyl-4-carbonyl)-4-(4-fluoro-phenyl)-piperidne-4-carboxylic acid (intermediate 28) and phenyl-hydrazine (commercially available) | 512.4 |
| 151 | 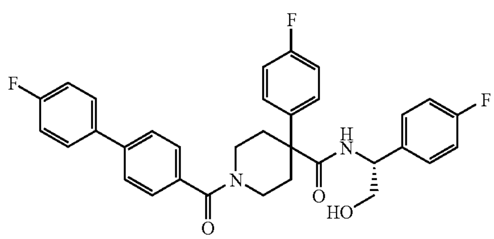 | 558.597 | 1-(4'-Fluoro-biphenyl-4-carbonyl)-4-(4-fluoro-phenyl)-piperidine-4-carboxylic acid [(R)-1-(4-fluoro-phenyl)-2-hydroxy-ethyl]-amide | 1-(4'-Fluoro-biphenyl-4-carbonyl)-4-(4-fluoro-phenyl)-piperidine-4-carboxylic acid (intermediate 28) and (R)-2-amino-2-phenyl-ethanol (commercially available) | 559.2 |
| 152 | 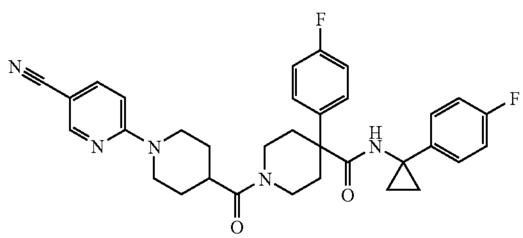 | 569.66 | 1-(5'-Cyano-3,4,5,6-tetrahydro-2H-[1,2']bipyridinyl-4-carbonyl)-4-(4-fluoro-phenyl)-piperidine-4-carboxylic acid [1-(4-fluoro-phenyl)-cyclopropyl]-amide | 1-(5'-Cyano-3,4,5,6-tetrahydro-2H-[1,2']bipyridinyl-4-carbony)-4-(4-fluoro-phenyl)-piperidine-4-carboxylic acid (intermediate 29) and 1-(4-fluoro-phenyl)-cyclopropylamine (commercially available) | 570.4 |
| 153 | 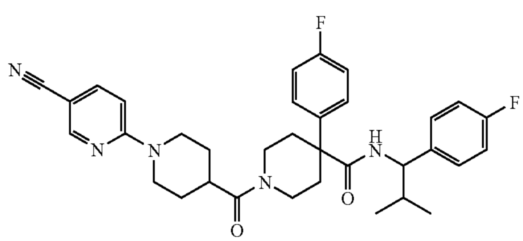 | 585.7 | 1-(5'-Cyano-3,4,5,6-tetrahydro-2H-[1,2']bipyridinyl-4-carbonyl)-4-(4-fluoro-phenyl)-piperidine-4-carboxylic acid [1-(4-fluoro-phenyl)-2-methyl-propyl]-amide | 1-(5'-Cyano-3,4,5,6-tetrahydro-2H-[1,2']bipyridinyl-4-carbonyl)-4-(4-fluoro-phenyl)-piperidine-4-carboxylic acid (intermediate 29) and 1-(4-fluoro-phenyl)-2-methyl-propylamine (commercially available) | 586.3 |
| 154 | 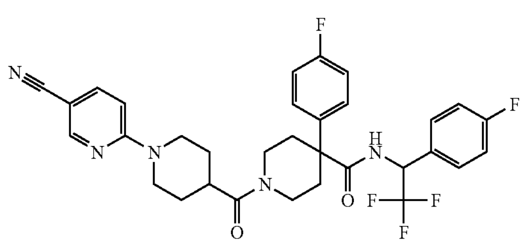 | 611.61 | 1-(5'-Cyano-3,4,5,6-tetrahydro-2H-[1,2']bipyridinyl-4-carbonyl)-4-(4-fluoro-phenyl)-piperidine-4-carboxylic acid [2,2,2-trifluoro-1-(4-fluoro-phenyl)-ethyl]-amide | 1-(5'-Cyano-3,4,5,6-tetrahydro-2H-[1,2']bipyridinyl-4-carbony)-4-(4-fluoro-phenyl)-piperidine-4-carboxylic acid (intermediate 29) and 2,2,2-trifluoro-1-(4-fluoro-phenyl)-ethylamine (commercially available) | 612.3 |
| 155 | 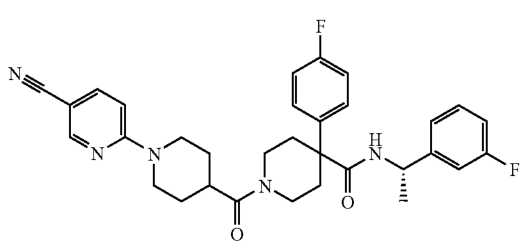 | 557.64 | 1-(5'-Cyano-3,4,5,6-tetrahydro-2H-[1,2']bipyridinyl-4-carbonyl)-4-(4-fluoro-phenyl)-piperidine-4-carboxylic acid [(S)-1-(3-fluoro-phenyl)-ethyl]-amide | 1-(5'-Cyano-3,4,5,6-tetrahydro-2H-[1,2']bipyridinyl-4-carbonyl)-4-(4-fluoro-phenyl)-piperidine-4-carboxylic acid (intermediate 29) and (S)-1-(3-fluoro-phenyl)-ethylamine (commercially available) | 558.3 |

TABLE 3-continued

| No | structure | MW calc. | systematic Name | starting materials | MW (MH+) |
|---|---|---|---|---|---|
| 156 | 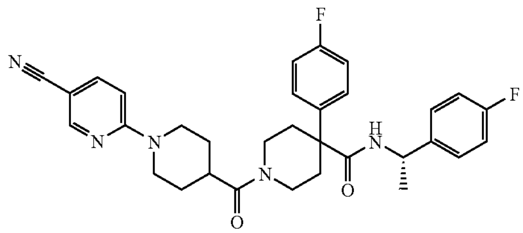 | 557.64 | 1-(5'-Cyano-3,4,5,6-tetrahydro-2H-[1,2']bipyridinyl-4-carbonyl)-4-(4-fluoro-phenyl)-piperidine-4-carboxylic acid [(S)-1-(4-fluoro-phenyl)-ethyl]-amide | 1-(5'-Cyano-3,4,5,6-tetrahydro-2H-[1,2']bipyridinyl-4-carbony)-4-(4-fluoro-phenyl)-piperidine-4-carboxylic acid (intermediate 29) and (S)-1-(4-fluoro-phenyl)-ethylamine (commercially available) and | 558.3 |
| 157 | 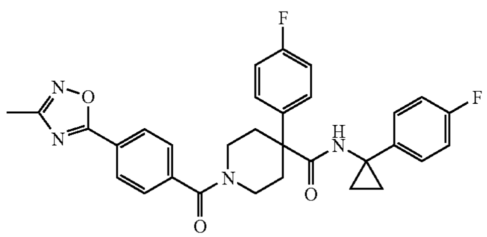 | 542.59 | 4-(4-Fluoro-phenyl)-1-[4-(3-methyl-[1,2,4]oxadiazol-5-yl)-benzoyl]-piperidine-4-carboxylic acid [1-(4-fluoro-phenyl)-cyclopropyl]-amide | 4-(4-Fluoro-phenyl)-1-[4-(3-methyl-[1,2,4]oxadiazol-5-yl)-benzoyl]-piperidine-4-carboxylic acid (intermediate 30) and 1-(4-fluoro-phenyl)-cyclopropylamine (commercially available) | 543.3 |
| 158 | 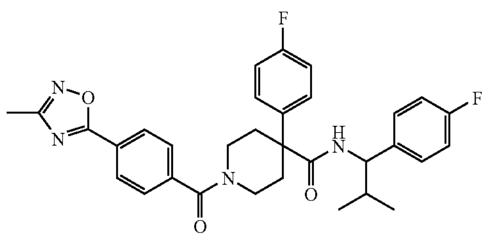 | 558.63 | 4-(4-Fluoro-phenyl)-1-[4-(3-methyl-[1,2,4]oxadiazol-5-yl)-benzoyl]-piperidine-4-carboxylic acid [1-(4-fluoro-phenyl)-2-methyl-propyl]-amide | 4-(4-Fluoro-phenyl)-1-[4-(3-methyl-[1,2,4]oxadiazol-5-yl)-benzoyl]-piperidine-4-carboxylic acid (intermediate 30) and 1-(4-fluoro-phenyl)-2-methyl-propylamine (commercially available) | 559.3 |
| 159 | 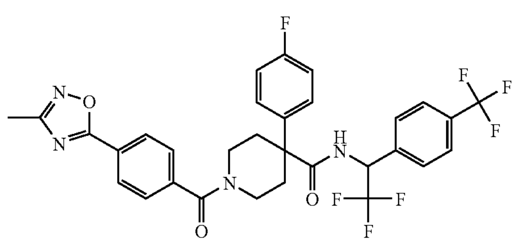 | 634.55 | 4-(4-Fluoro-phenyl)-1-[4-(3-methyl-[1,2,4]oxadiazol-5-yl)-benzoyl]-piperidine-4-carboxylic acid [2,2,2-trifluoro-1-(4-trifluoromethyl-phenyl-ethyl]-amide | 4-(4-Fluoro-phenyl)-1-[4-(3-methyl-[1,2,4]oxadiazol-5-yl)-benzoyl]-piperidine-4-carboxylic acid (intermediate 30) and 2,2,2-trifluoro-1-(4-trifluoromethyl-phenyl)-ethylamine (commercially available) | 635.2 |
| 160 | 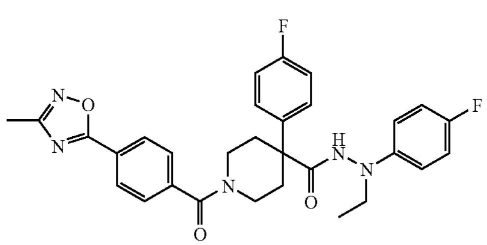 | 545.59 | 4-(4-Fluoro-phenyl)-1-[4-(3-methyl-[1,2,4]oxodiazol-5-yl)-benzoyl]-piperidine-4-carboxylic acid N'-ethyl-#N!'-(4-fluoro-phenyl)-hydrazide | 4-(4-Fluoro-phenyl)-1-[4-(3-methyl-[1,2,4]oxadiazol-5-yl)-benzoyl]-piperidine-4-carboxylic acid (intermediate 30) and N-ethyl-N-(4-fluoro-phenyl)-hydrazine (WO20060992510) | 546.2 |
| 161 | 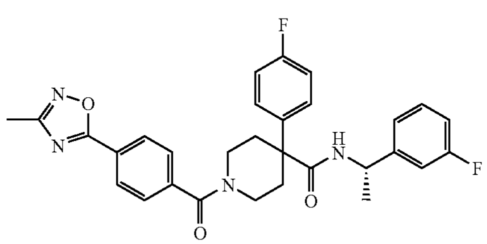 | 530.57 | 4-(4-Fluoro-phenyl)-1-[4-(3-methyl-[1,2,4]oxadiazol-5-yl)-benzoyl]-piperidine-4-carboxylic acid [(S)-1-(3-fluoro-phenyl)-ethyl]-amide | 4-(4-Fluoro-phenyl)-1-[4-(3-methyl-[1,2,4]oxadiazol-5-yl)-benzoyl]-piperidine-4-carboxylic acid (intermediate 30) and (S)-1-(3-fluoro-phenyl)-ethylamine (commercially available) | 531.2 |

| No | structure | MW calc. | systematic Name | starting materials | MW (MH+) |
|---|---|---|---|---|---|
| 162 | 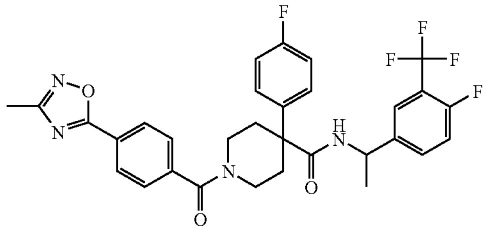 | 598.57 | 4-(4-Fluoro-phenyl)-1-[4-(3-methyl-[1,2,4]oxadiazol-5-yl)-benzoyl]-piperidine-4-carboxylic acid [1-(4-fluoro-3-trifluoromethyl-phenyl)-ethyl]-amide | 4-(4-Fluoro-phenyl)-1-[4-(3-methyl-[1,2,4]oxadiazol-5-yl)-benzoyl]-piperidine-4-carboxylic acid (intermediate 30) and 1-(4-fluoro-3-trifluoromethyl-phenyl)-ethylamine (commerically available) | 599.2 |
| 163 | 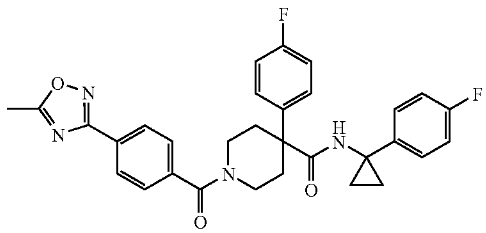 | 542.59 | 4-(4-Fluoro-phenyl)-1-[4-(5-methyl-[1,2,4]oxadiazol-3-yl)-benzoyl]-piperidine-4-carboxylic acid [1-(4-fluoro-phenyl)-cyclopropyl]-amide | 4-(4-Fluoro-phenyl)-1-[4-(5-methyl-[1,2,4]oxadiazol-3-yl)-benzoyl]-piperidine-4-carboxylic acid (intermediate 31) and 1-(4-fluoro-phenyl)-cyclopropylamine (commerically available) | 543.3 |
| 164 | 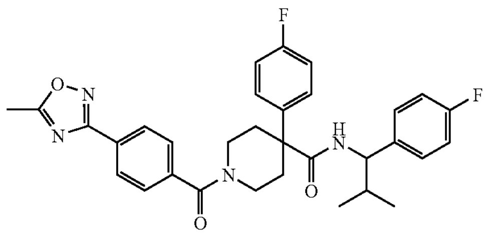 | 558.63 | 4-(4-Fluoro-phenyl)-1-[4-(5-methyl-[1,2,4]oxadiazol-3-yl)-benzoyl]-piperidne-4-carboxylic acid [1-(4-fluoro-phenyl)-2-methyl-propyl]-amide | 4-(4-Fluoro-phenyl)-1-[4-(5-methyl-[1,2,4]oxadiazol-3-yl-benzoyl]-piperidine-4-carboxylic acid (intermediate 31) and 1-(4-fluoro-phenyl)-2-methyl-propylamine (commerically available) | 559.3 |
| 165 | 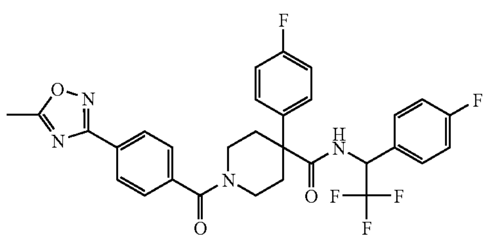 | 584.54 | 4-(4-Fluoro-phenyl)-1-[4-(5-methyl-[1,2,4]oxadiazol-3-yl)-benzoyl]-piperidne-4-carboxylic acid [2,2,2-trifluoro-1-(4-fluoro-phenyl)-ethyl]-amide | 4-(4-Fluoro-phenyl)-1-[4-(5-methyl-[1,2,4]oxadiazol-3-yl)-benzoyl]-piperidine-4-carboxylic acid (intermediate 31) and 2,2,2-trifluoro-1-(4-fluoro-phenyl)-ethylamine (commerically available) | 585.2 |
| 166 | 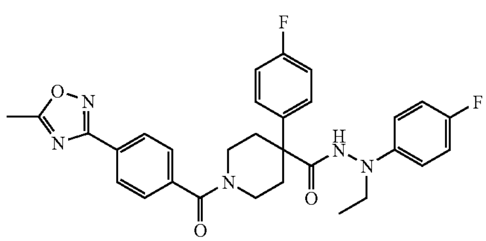 | 545.59 | 4-(4-Fluoro-phenyl)-1-[4-(5-methyl-[1,2,4]oxadiazol-3-yl)-benzoyl]-piperidine-4-carboxylic acid #N!'-ethyl-#N'-(4-fluoro-phenyl)-hydrazide | 4-(4-Fluoro-phenyl)-1-[4-(5-methyl-[1,2,4]oxadiazol-3-yl)-benzoyl]-piperidine-4-carboxylic acid (intermediate 31) and N-ethyl-N-(4-fluoro-phenyl)-hydrazine (WO2006092510) | 546.2 |
| 167 | 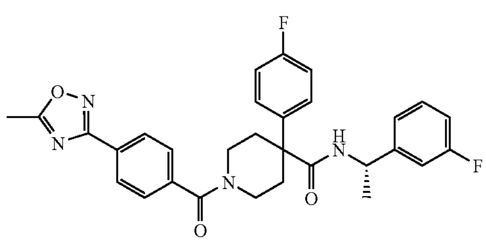 | 530.57 | 4-(4-Fluoro-phenyl)-1-[4-(5-methyl-[1,2,4]oxadiazol-3-yl)-benzoyl]-piperidine-4-carboxylic acid [(S)-1-(3-fluoro-phenyl)-ethyl]-amide | 4-(4-Fluoro-phenyl)-1-[4-(5-methyl-[1,2,4]oxadiazol-3-yl)-benzoyl]-piperidine-4-carboxylic acid (intermediate 31) and (S)-1-(3-fluoro-phenyl)-ethylamine (commerically available) | 531.2 |

TABLE 3-continued

| No | structure | MW calc. | systematic Name | starting materials | MW (MH+) |
|---|---|---|---|---|---|
| 168 | 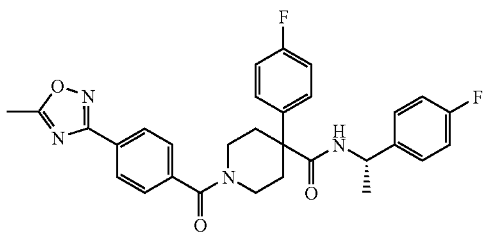 | 530.57 | 4-(4-Fluoro-phenyl)-1-[4-(5-methyl-[1,2,4]oxadiazol-3-yl)-benzoyl]-piperidine-4-carboxylic acid [(S)-1-(4-fluoro-phenyl)-ethyl]-amide | 4-(4-Fluoro-phenyl)-1-[4-(5-methyl-[1,2,4]oxadiazol-3-yl)-benzoyl]-piperidine-4-carboxylic acid (intermediate 31) and (S)-1-(4-fluoro-phenyl)-ethylamine (commercially available) | 531.1 |
| 169 | 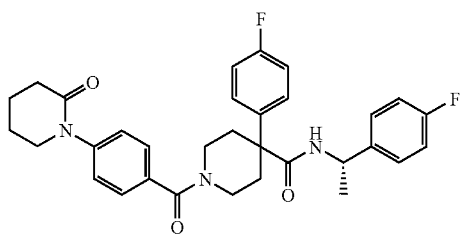 | 545.627 | 4-(4-Fluoro-phenyl)-1-[4-(2-oxo-piperidin-1-yl)-benzoyl]-piperidine-4-carboxylic acid [(S)-1-(4-fluoro-phenyl)-ethyl]-amide | 4-(4-Fluoro-phenyl)-1-[4-(2-oxo-piperidin-1-yl)-benzoyl]-piperidine-4-carboxylic acid (intermediate 32) and (S)-1-(4-fluoro-phenyl)-ethylamine (commercially available) | 546.2 |
| 170 | 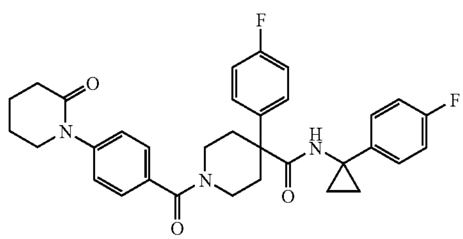 | 557.64 | 4-(4-Fluoro-phenyl)-1-[4-(2-oxo-piperidin-1-yl)-benzoyl]-piperidine-4-carboxylic acid [1-(4-fluoro-phenyl)-cyclopropyl]-amide | 4-(4-Fluoro-phenyl)-1-[4-(2-oxo-piperidin-1-yl)-benzoyl]-piperidine-4-carboxylic acid (intermediate 32) and 1-(4-fluoro-phenyl)-cyclopropylamine (commercially available) | 558.3 |
| 171 | 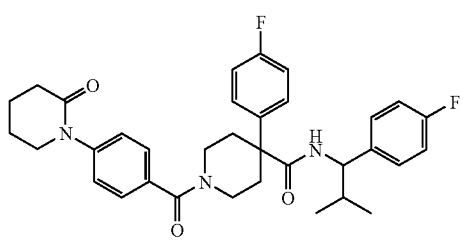 | 573.68 | 4-(4-Fluoro-phenyl)-1-[4-(2-oxo-piperidin-1-yl)-benzoyl]-piperidine-4-carboxylic acid [1-(4-fluoro-phenyl)-2-methyl-propyl]-amide | 4-(4-Fluoro-phenyl)-1-[4-(2-oxo-piperidin-1-yl)-benzoyl]-piperidine-4-carboxylic acid (intermediate 32) and 1-(4-fluoro-phenyl)-2-methyl-propylamine (commercially available) | 574.4 |
| 172 | 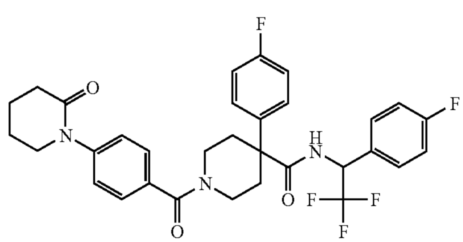 | 599.6 | 4-(4-Fluoro-phenyl)-1-[4-(2-oxo-piperidin-1-yl)-benzoyl]-piperidine-4-carboxylic acid [2,2,2-trifluoro-1-(4-fluoro-phenyl)-ethyl]-amide | 4-(4-Fluoro-phenyl)-1-[4-(2-oxo-piperidin-1-yl)-benzoyl]-piperidine-4-carboxylic acid (intermediate 32) and 2,2,2-trifluoro-1-(4-fluoro-phenyl)-ethylamine (commercially available) | 600.2 |
| 173 | 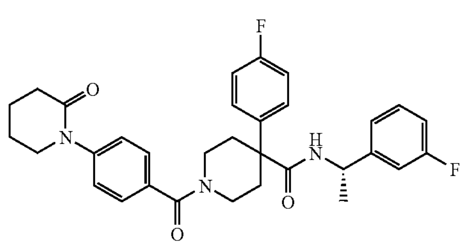 | 545.63 | 4-(4-Fluoro-phenyl)-1-[4-(2-oxo-piperidin-1-yl)-benzoyl]-piperidine-4-carboxylic acid [(S)-1-(3-fluoro-phenyl)-ethyl]-amide | 4-(4-Fluoro-phenyl)-1-[4-(2-oxo-piperidin-1-yl)-benzoyl]-piperidine-4-carboxylic acid (intermediate 32) and (S)-1-(3-fluoro-phenyl)-ethylamine (commercially available) | 546.2 |

TABLE 3-continued

| No | structure | MW calc. | systematic Name | starting materials | MW (MH+) |
|---|---|---|---|---|---|
| 174 | 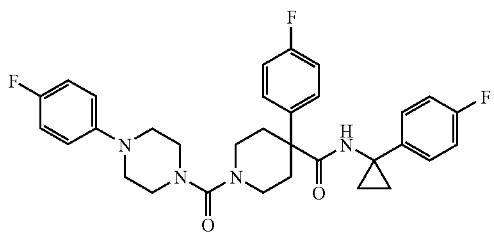 | 562.64 | 4-(4-Fluoro-phenyl)-1-[4-(4-fluoro-phenyl)-piperazine-1-carbonyl]-piperidine-4-carboxylic acid [1-(4-fluoro-phenyl)-cyclopropyl]-amide | 4-(4-Fluoro-phenyl)-1-[4-(4-fluoro-phenyl)-piperazine-1-carbonyl]-piperidine-4-carboxylic acid (intermediate 33) and 1-(4-fluoro-phenyl)-cyclopropylmaine (commercially available) | 563.3 |
| 175 | 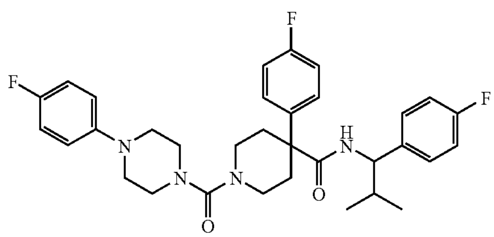 | 578.68 | 4-(4-Fluoro-phenyl)-1-[4-(4-fluoro-phenyl)-piperazine-1-carbonyl]-piperidine-4-carboxylic acid [1-(4-fluoro-phenyl)-2-methyl-propyl]-amide | 4-(4-Fluoro-phenyl)-1-[4-(4-fluoro-phenyl)-piperazine-1-carbonyl]-piperidine-4-carboxylic acid (intermediate 33) and 1-(4-fluoro-phenyl)-2-methyl-propylamine (commercially available) | 579.4 |
| 176 | 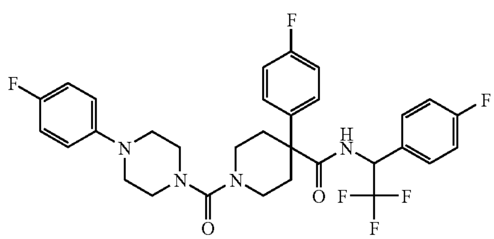 | 604.59 | 4-(4-Fluoro-phenyl)-1-[4-(4-fluoro-phenyl)-piperazine-1-carbonyl]-piperidine-4-carboxylic acid [2,2,2-trifluoro-1-(4-fluoro-phenyl)-ethyl]-amide | 4-(4-Fluoro-phenyl)-1-[4-(4-fluoro-phenyl)-piperazine-1-carbonyl]-piperidine-4-carboxylic acid (intermediate 33) and 2,2,2-trifluoro-1-(4-fluoro-phenyl)-ethylamine (commercially available) | 605.3 |
| 177 | 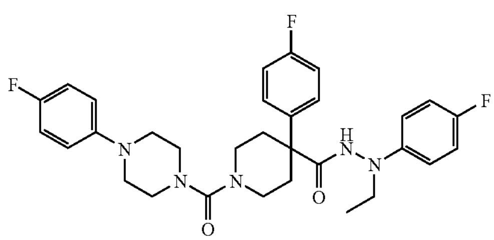 | 565.64 | 4-(4-Fluoro-phenyl)-1-[4-(4-fluoro-phenyl)-piperazine-1-carbonyl]-piperidine-4-carboxylic acid N'-ethyl-N'-(4-fluoro-phenyl)-hydrazide | 4-(4-Fluoro-phenyl)-1-[4-(4-fluoro-phenyl)-piperazine-1-carbonyl]-piperidine-4-carboxylic acid (intermediate 33) and N-ethyl-N-(4-fluoro-phenyl)-hydrazine (WO2006092510) | 566.4 |
| 178 | 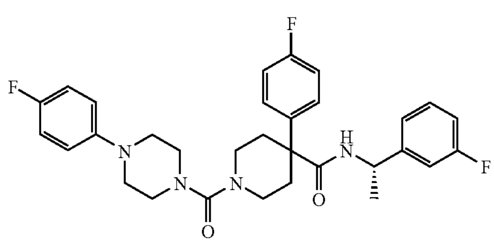 | 550.62 | 4-(4-Fluoro-phenyl)-1-[4-(4-fluoro-phenyl)-piperazine-1-carbonyl]-piperidine-4-carboxylic acid [(S)-1-(3-fluoro-phenyl)-ethyl]-amide | 4-(4-Fluoro-phenyl)-1-[4-(4-fluoro-phenyl)-piperazine-1-carbonyl]-piperidine-4-carboxylic acid (intermediate 33) and (S)-1-(3-fluoro-phenyl)-ethylamine (commercially available) | 551.4 |
| 179 | 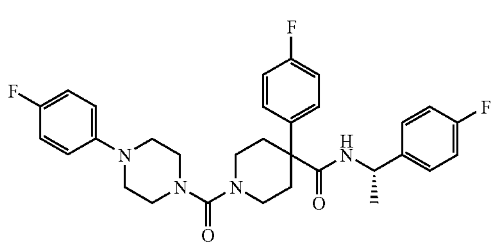 | 550.62 | 4-(4-Fluoro-phenyl)-1-[4-(fluoro-phenyl)-piperazine-1-carbonyl]-piperidine-4-carboxylic acid [(S)-1-(4-fluoro-phenyl)-ethyl]-amide | 4-(4-Fluoro-phenyl)-1-[4-(4-fluoro-phenyl)-piperazine-1-carbonyl]-piperidine-4-carboxylic acid (intermediate 33) and (S)-1-(4-fluoro-phenyl)-ethylamine (commercially available) | 551.4 |

TABLE 3-continued

| No | structure | MW calc. | systematic Name | starting materials | MW (MH+) |
|---|---|---|---|---|---|
| 180 | 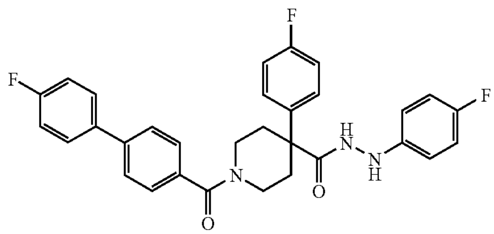 | 529.56 | 1-(4'-Fluoro-biphenyl-4-carbonyl)-4-(4-fluoro-phenyl)-piperidine-4-carboxylic acid N'-(4-fluoro-phenyl)-hydrazide | 1-(4'-Fluoro-biphenyl-4-carbonyl)-4-(4-fluoro-phenyl)-piperidine-4-carboxylic acid (intermediate 28) and (4-fluoro-phenyl)-hydrazine (commercially available) | 530.2 |
| 181 | 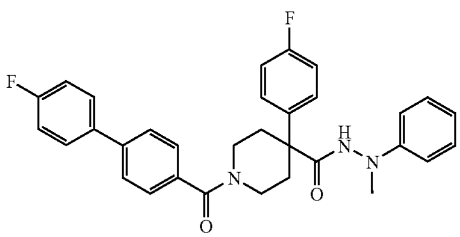 | 525.596 | 1-(4'-Fluoro-biphenyl-4-carbonyl)-4-(4-fluoro-phenyl)-piperidine-4-carboxylic acid N'-methyl-N'-phenyl-hydrazide | 1-(4'-Fluoro-biphenyl-4-carbonyl)-4-(4-fluoro-phenyl)-piperidine-4-carboxylic acid (intermediate 28) and N-methyl-N-phenyl-hydrazine (commercially available) | 526.3 |
| 182 | 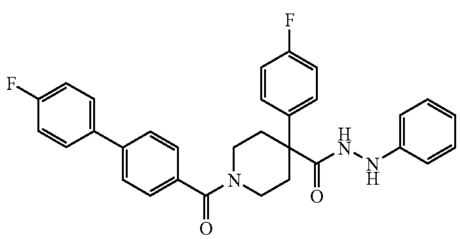 | 511.569 | 1-(4'-Fluoro-biphenyl-4-carbonyl)-4-(4-fluoro-phenyl)-piperidine-4-carboxylic acid N'-phenyl-hydrazide | 1-(4'-Fluoro-biphenyl-4-carbonyl)-4-(4-fluoro-phenyl)-piperdine-4-carboxylic acid (intermediate 28) and phenyl-hydrazine (commercially available) | 512.4 |
| 183 | 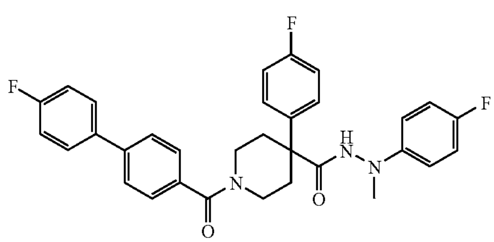 | 543.586 | 1-(4'-Fluoro-biphenyl-4-carbonyl)-4-(4-fluoro-phenyl)-piperidine-4-carboxylic acid N'-(4-fluoro-phenyl)-N'-methyl-hydrazide | 1-(4'-Fluoro-biphenyl-4-carbonyl)-4-(4-fluoro-phenyl)-piperidine-4-carboxylic acid (intermediate 28) and N-(4-fluoro-phenyl)-N-methyl-hydrazine (Journal of the Chemical Society 1960, 5259-61) | 544.4 |
| 184 | 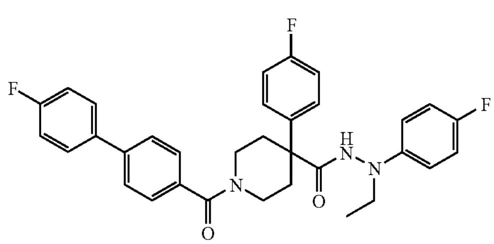 | 557.613 | 1-(4'-Fluoro-biphenyl-4-carbonyl)-4-(4-fluoro-phenyl)-piperidine-4-carboxylic acid N'-ethyl-N'-(4-fluoro-phenyl)-hydrazine | 1-(4'-Fluoro-biphenyl-4-carbonyl)-4-(4-fluoro-phenyl)-piperidine-4-carboxylic acid (intermediate 28) and N-ethyl-N-(4-fluoro-phenyl)-hydrazine (Journal of the Chemical Society 1960, 5259-61) | 558.2 |
| 185 | 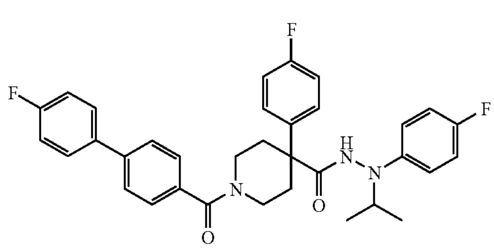 | 571.64 | 1-(4'-Fluoro-biphenyl-4-carbonyl)-4-(4-fluoro-phenyl)-piperidine-4-carboxylic acid N'-(4-fluoro-phenyl)-N'-isopropyl-hydrazide | 1-(4'-Fluoro-biphenyl-4-carbonyl)-4-(4-fluoro-phenyl)-piperidine-4-carboxylic acid (intermediate 28) and N-(4-fluoro-phenyl)-N-isopropyl-hydrazine (CA1299577) | 572.2 |

TABLE 3-continued

| No | structure | MW calc. | systematic Name | starting materials | MW (MH+) |
|---|---|---|---|---|---|
| 186 | 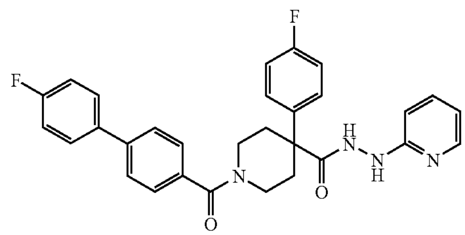 | 512.56 | 1-(4'-Fluoro-biphenyl-4-carbonyl)-4-(4-fluoro-phenyl)-piperidine-4-carboxylic acid N'-pyridin-2-yl-hydrazide | 1-(4'-Fluoro-biphenyl-4-carbonyl)-4-(4-fluoro-phenyl)-piperidine-4-carboxylic acid (intermediate 28) and pyridin-2-yl-hydrazine (commercially available) | 513.4 |
| 187 | 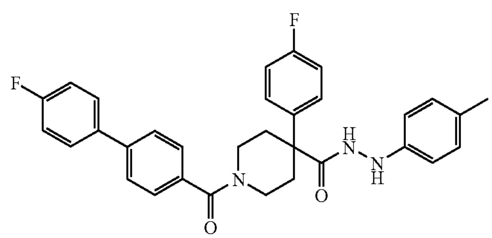 | 525.6 | 1-(4'-Fluoro-biphenyl-4-carbonyl)-4-(4-fluoro-phenyl)-piperidine-4-carboxylic acid N'-p-tolyl-hydrazide | 1-(4'-Fluoro-biphenyl)-4-carbonyl)-4-(4-fluoro-phenyl)-piperidine-4-carboxylic acid (intermediate 28) and p-tolyl-hydrazine (commercially available) | 526.3 |
| 188 | 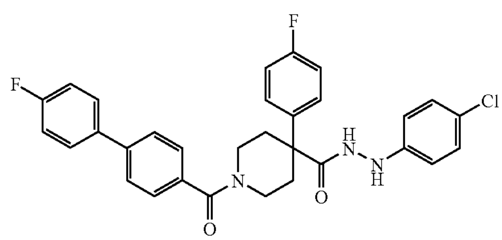 | 546.02 | 1-(4'-Fluoro-biphenyl-4-carbonyl)-4-(4-fluoro-phenyl)-piperidine-4-carboxylic acid N'-(4-chloro-phenyl)-hydrazide | 1-(4'-Fluoro-biphenyl-4-carbonyl)-4-(4-fluoro-phenyl)-piperidine-4-carboxylic acid (intermediate 28) and (4-chloro-phenyl)-hydrazine (commercially available) | 546.1 |
| 189 | 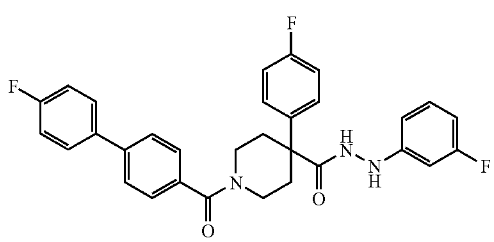 | 529.56 | 1-(4'-Fluoro-biphenyl-4-carbonyl)-4-(4-fluoro-phenyl)-piperdine-4-carboxylic acid N'-(3-fluoro-phenyl)-hydrazide | 1-(4'-Fluoro-biphenyl-4-carbonyl)-4-(4-fluoro-phenyl)-piperidne-4-carboxylic acid (intermediate 28) and (3-fluoro-phenyl)-hydrazine (commercially available) | 530.1 |
| 190 | 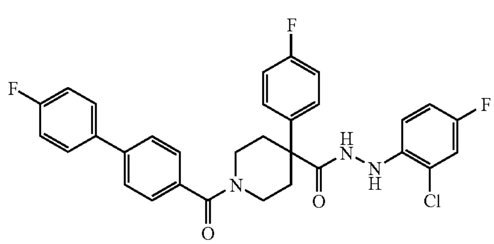 | 564.01 | 1-(4'-Fluoro-biphenyl-4-carbonyl)-4-(4-fluoro-phenyl)-piperidine-4-carboxylic acid N'-(2-chloro-4-fluoro-phenyl)-hydrazide | 1-(4'-Fluoro-biphenyl-4-carbonyl)-4-(4-fluoro-phenyl)-piperidine-4-carboxylic acid (intermediate 28) and (2-chloro-4-fluoro-phenyl)-hydrazine (commercially available) | 564.2 |
| 191 | 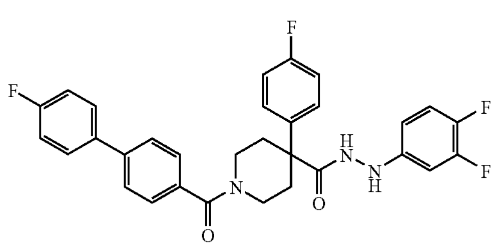 | 547.55 | 1-(4'-Fluoro-biphenyl-4-carbonyl)-4-(4-fluoro-phenyl)-piperidine-4-carboxylic acid N'-(3,4-difluoro-phenyl)-hydrazide | 1-(4'-Fluoro-biphenyl-4-carbonyl)-4-(4-fluoro-phenyl)-piperidine-4-carboxylic acid (intermediate 28) and (3,4-difluoro-phenyl)-hydrazine (commercially available) | 548.3 |

TABLE 3-continued

| No | structure | MW calc. | systematic Name | starting materials | MW (MH+) |
|---|---|---|---|---|---|
| 192 | 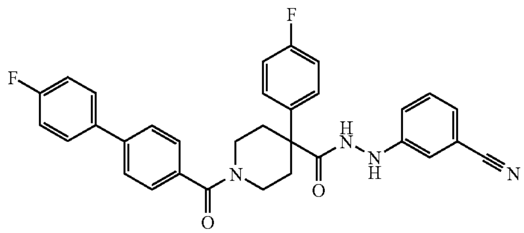 | 536.58 | 1-(4'-Fluoro-biphenyl-4-carbonyl)-4-(4-fluoro-phenyl)-piperidine-4-carboxylic acid N'-(3-cyano-phenyl)-hydrazide | 1-(4'-Fluoro-biphenyl-4-carbonyl)-4-(4-fluoro-phenyl)-piperidine-4-carboxylic acid (intermediate 28) and 3-hydrazino-benzonitrile (commercially available) | 537.2 |
| 193 | 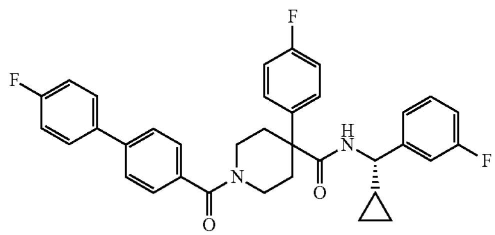 | 568.636 | 1-(4'-Fluoro-biphenyl-4-carbonyl)-4-(4-fluoro-phenyl)-piperidine-4-carboxylci acid [(S)-cyclopropyl-(3-fluoro-phenyl)-methyl]-amide | 1-(4'-Fluoro-biphenyl-4-carbonyl)-4-(4-fluoro-phenyl)-piperidine-4-carboxylic acid (intermediate 28) and C-[(S)-C-cyclopropyl-C-(3-fluoro-phenyl)]-methylamine (commercially available) | 569.2 |
| 194 | 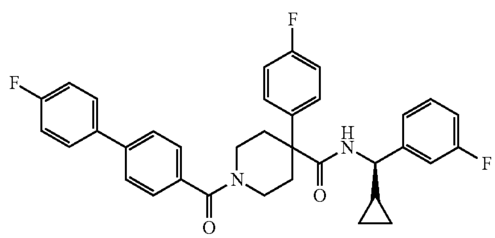 | 568.636 | 1-(4'-Fluoro-biphenyl-4-carbonyl)-4-(4-fluoro-phenyl)-piperidine-4-carboxylic acid [(R)-cyclopropyl-(3-fluoro-phenyl)-methyl]-amide | 1-(4'-Fluoro-biphenyl-4-carbonyl)-4-(4-fluoro-phenyl)-piperidine-4-carboxylic acid (intermediate 28) and C-[(R)-C-cyclopropyl-C-(3-fluoro-phenyl)]-methylamine (commercially available) | 569.2 |
| 195 | 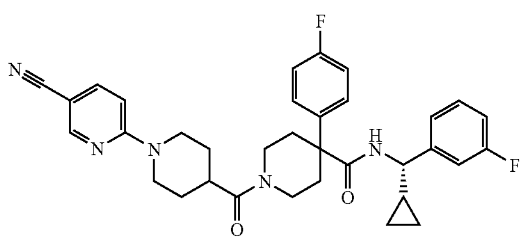 | 583.679 | 1-(5'-Cyano-3,4,5,6-tetrahydro-2H-[1,2']bipyridinyl-4-carbonyl)-4-(4-fluoro-phenyl)-piperidine-4-carboxylic acid [(S)-cyclopropyl-(3-fluoro-phenyl)-methyl]-amide | Intermediate 29 1-(5'-Cyano-3,4,5,6-tetrahydro-2H-[1,2']bipyridinyl-4-carbonyl)-4-(4-fluoro-phenyl)-piperidine-4-carboxylic acid (intermediate 29) and C-[(S)-C-cyclopropyl-C-(3-fluoro-phenyl)]-methylamine (commercially available) | 584.2 |
| 196 | 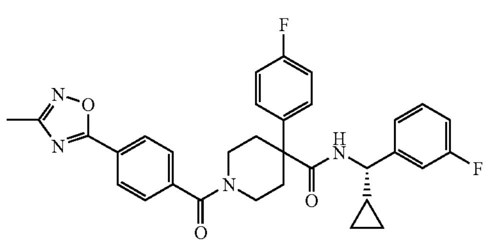 | 556.61 | 4-(4-Fluoro-phenyl)-1-[4-(3-methyl-[1,2,4]oxadiazol-5-yl)-benzoyl]-piperidine-4-carboxylic acid [(S)-cyclopropyl-(3-fluoro-phenyl)-methyl]-amide | 4-(4-Fluoro-phenyl)-1-[4-(3-methyl-[1,2,4]oxadiazol-5-yl)-benzoyl]-piperidine-4-carboxylic acid (intermediate 30) and (S)-1-(3-fluoro-phenyl)-ethylamine (commercially available) | 557.1 |

TABLE 3-continued

| No | structure | MW calc. | systematic Name | starting materials | MW (MH+) |
|----|-----------|----------|-----------------|--------------------|----------|
| 197 | 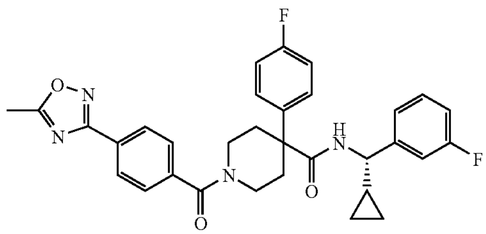 | 556.61 | 4-(4-Fluoro-phenyl)-1-[4-(5-methyl-[1,2,4]oxadiazol-3-yl)-benzoyl]-piperidine-4-carboxylic acid [(S)-cyclopropyl-(3-fluoro-phenyl)-methyl]-amide | 4-(4-Fluoro-phenyl)-1-[4-(5-methyl-[1,2,4]oxadiazol-3-yl)-benzoyl]-piperidine-4-carboxylic acid (intermediate 31) and C-[(S)-C-cyclopropyl-C-(3-fluoro-phenyl)]-methylamine (commercially available) | 557.1 |
| 198 | 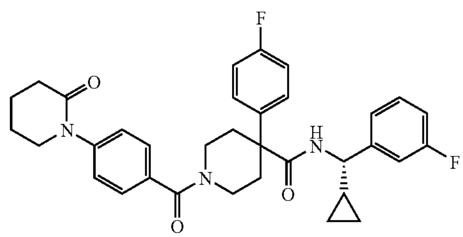 | 571.664 | 4-(4-Fluoro-phenyl)-1-[4-(2-oxo-piperidin-1-yl)-benzoyl]-piperidine-4-carboxylic acid [(S)-cyclopropyl-(3-fluoro-phenyl)-methyl]-amide | 4-(4-Fluoro-phenyl)-1-[4-(2-oxo-piperidin-1-yl)-benzoyl]-piperidine-4-carboxylic acid (intermediate 32) and C-[(S)-C-cyclopropyl-C-(3-fluoro-phenyl)]-methylamine (commercially available) | 572.3 |
| 199 | 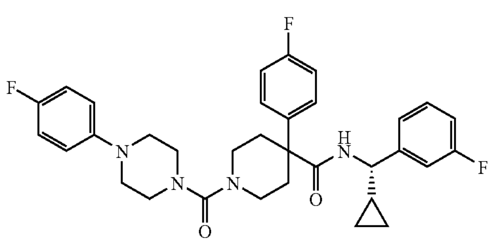 | 576.659 | 4-(4-Fluoro-phenyl)-1-[4-(4-fluoro-phenyl)-piperazine-1-carbonyl]-piperidine-4-carboxylic acid [(S)-cyclopropyl-(3-fluoro-phenyl)-methyl]-amide | 4-(4-Fluoro-phenyl)-1-[4-(4-fluoro-phenyl)-piperazine-1-carbonyl]-piperidine-4-carboxylic acid (intermediate 33) and C-[(S)-C-cyclopropyl-C-(3-fluoro-phenyl)]-methylamine (commercially available) | 577.3 |
| 200 | 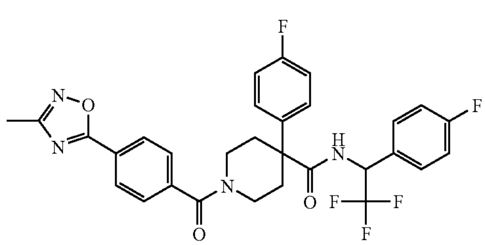 | 548.543 | 4-(4-Fluoro-phenyl)-1-[4-(3-methyl-[1,2,4]oxadiazol-5-yl)-benzoyl]-piperidine-4-carboxylic acid [2,2,2-trifluoro-1-(4-fluoro-phenyl)-ethyl]-amide | 4-(4-Fluoro-phenyl)-1-[4-(3-methyl-[1,2,4]oxadiazol-5-yl)-benzoyl]-piperidine-4-carboxylic acid (intermediate 30) and 2,2,2-trifluoro-1-(4-fluoro-phenyl)-ethylamine (commercially available) | 585.2 |

Example 201

4-(4-Fluoro-phenyl)-1-[4-(3-methyl-[1,2,4]oxadiazol-5-yl)-benzoyl]-piperidine-4-carboxylic acid [(RS)-2,2,2-trifluoro-1-(4-fluoro-phenyl)-ethyl]-amide

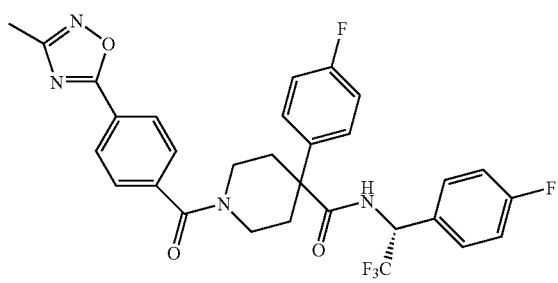

The title compound was accessed through isolation from chiral HPLC separation from 4-(4-Fluoro-phenyl)-1-[4-(3-methyl-[1,2,4]oxadiazol-5-yl)-benzoyl]-piperidine-4-carboxylic acid [2,2,2-trifluoro-1-(4-fluoro-phenyl)-ethyl]amide (example 200) as off white solid. MS ISP (m/e): 585.2 [(M+H)+].

Example 202

4-(4-Fluoro-phenyl)-1-[4-(3-methyl-[1,2,4]oxadiazol-5-yl)-benzoyl]-piperidine-4-carboxylic acid [(SR)-2,2,2-trifluoro-1-(4-fluoro-phenyl)-ethyl]-amide

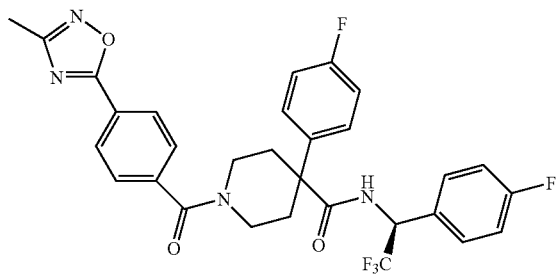

The title compound was accessed through isolation from chiral HPLC separation from 4-(4-Fluoro-phenyl)-1-[4-(3-methyl-[1,2,4]oxadiazol-5-yl)-benzoyl]-piperidine-4-carboxylic acid [2,2,2-trifluoro-1-(4-fluoro-phenyl)-ethyl]-amide (example 200) as off white solid. MS ISP (m/e): 585.2 [(M+H)+].

Intermediate 34

4-[(S)-1-(4-Fluoro-phenyl)-ethylcarbamoyl]-4-phenyl-piperidine-1-carbonyl chloride

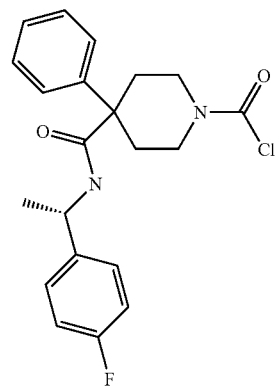

i) 4-Phenyl-piperidine-4-carboxylic acid [(S)-1-(4-fluoro phenyl)-ethyl]-amide 4-Phenyl-piperidine-4-carboxylic acid [(S)-1-(4-fluoro-phenyl)-ethyl]-amide; TFA-salt (260 mg, 0.590 mmol) was dissolved in ethyl acetate and saturated aqueous sodium bicarbonate solution. The aqueous phase was extracted three times with ethyl acetate, the organic layers were combined, dried over $Na_2SO_4$, and the solvents were evaporated to give 195 mg 4-phenyl-piperidine-4-carboxylic acid [(S)-1-(4-fluoro-phenyl)-ethyl]-amide. MS ISP (m/e): 327.3 [(M+H)+].

ii) 4-[(S)-1-(4-fluoro-phenyl)-ethylcarbamoyl]-4-phenyl-piperidine-1-carbonyl chloride To a solution of triphosgene (172 mg, 0.6 mmol) in dichloromethane (6 mL) at 0° C. under an argon atmosphere was added a solution of pyridine (106 µL, 1.32 mmol) in dichloromethane (3 mL) and a solution of 4-phenyl-piperidine-4-carboxylic acid [(S)-1-(4-fluoro-phenyl)-ethyl]-amide (195 mg, 0.6 mmol) in dichloromethane (6 ml). After stirring at room temperature for 12 h the reaction mixture was poured into ice water, the aqueous layer was saturated with NaCl, then extracted 6 times with dichloromethane, the combined organic layers were dried over $Na_2SO_4$ and the solvents were evaporated. The residue was purified by flash chromatography over a 10 g silica gel column with n-heptane and ethyl acetate to yield 233 mg 4-[(S)-1-(4-fluoro-phenyl)-ethylcarbamoyl]-4-phenyl-piperidine-1-carbonyl chloride. MS ISN (m/e): 387.4 [(M−H)$^−$].

Intermediate 35

4-Phenyl-4-((S)-1-phenyl-ethylcarbamoyl)-piperidine-1-carbonyl chloride

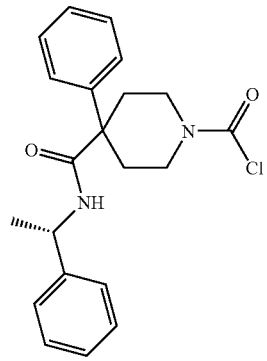

In analogy to the procedure described for the synthesis of 4-[(S)-1-(4-fluoro-phenyl)-ethylcarbamoyl]-4-phenyl-piperidine-1-carbonyl chloride (intermediate 14) the title compound was prepared from 4-phenyl-piperidine-4-carboxylic acid ((S)-1-phenyl-ethyl)-amide; compound with trifluoroacetic acid (intermediate 4) and triphosgene. MS ISP (m/e): 371.3 [(M+H)$^+$].

Example 203

1-[4-(4-Fluoro-phenyl)-piperazine-1-carbonyl]-4-phenyl-piperidine-4-carboxylic acid [(S)-1-(4-fluoro-phenyl)-ethyl]-amide

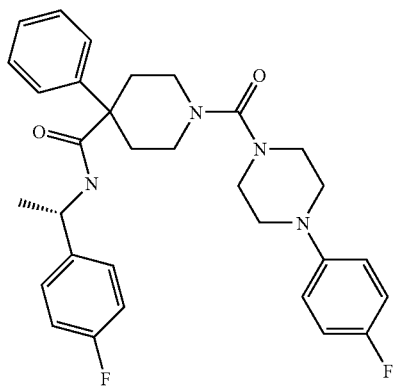

To a solution of 60 mg (0.154 mmol) 4-[(S)-1-(4-fluoro-phenyl)-ethylcarbamoyl]-4-phenyl-piperidine-1-carbonyl chloride in dichloromethane (2 mL) was added 28 mg (0.154 mmol) 1-fluorophenyl)piperazine and 39 uL (0.231 mmol) diisopropylethyl amine and stirred at room temperature for 48 h. The reaction mixture was subjected to flash chromatography with dichloromethane and methanol over a 10 g silica gel column to yield 59 mg 1-[4-(4-fluoro-phenyl)-piperazine-1-carbonyl]-4-phenyl-piperidine-4-carboxylic acid [(S)-1-(4-fluoro-phenyl)-ethyl]-amide. MS ISP (m/e): 533.4 (100) [(M+H)$^+$].

In analogy to the procedure described for the synthesis of 1-[4-(4-Fluoro-phenyl)-piperazine-1-carbonyl]-4-phenyl-piperidine-4-carboxylic acid [(S)-1-(4-fluoro-phenyl)-ethyl]-amide (example 203) further piperidine derivatives have been synthesized from their respective starting materials as mentioned in table 4. Table 4 comprises example 204-example 230.

TABLE 4

| No | structure | MW calc. | systematic Name | starting materials | MW (MH+) |
|---|---|---|---|---|---|
| 204 | 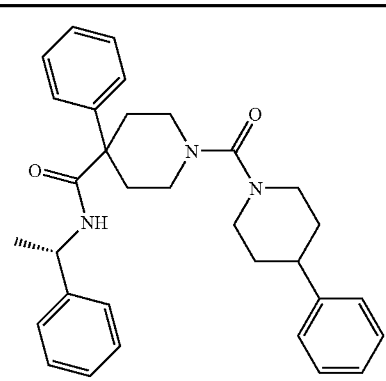 | 495.7 | 4-Phenyl-1-(4-phenyl-piperidine-1-carbonyl)-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 4-phenyl-piperidine (commercially available) | 496.5 |

TABLE 4-continued

| No | structure | MW calc. | systematic Name | starting materials | MW (MH+) |
|---|---|---|---|---|---|
| 205 | 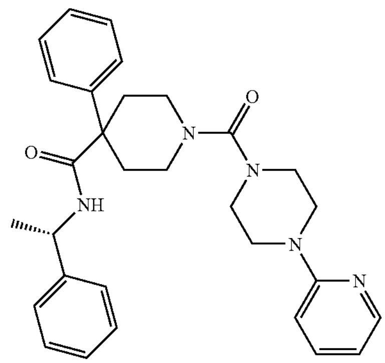 | 497.6 | 4-Phenyl-1-(4-pyridin-2-yl-piperazine-1-carbonyl)-piperidine-4-carboxylic acid ((S)-1-phenyl ethyl)-amide | 4-Phenyl-4-((S)-1-phenyl-ethylcarbamoyl)-piperidine-1-carbonyl chloride (intermediate 30) and 1-pyridin-2-yl-piperazine (commercially available) | 498.3 |
| 206 | 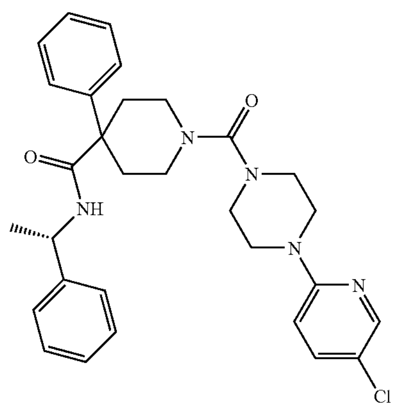 | 532.1 | 1-[4-(5-Chloro-pyridin-2-yl)-piperazine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-(5-chloro-pyridin-2-yl)-piperazine (commercially available) | 532.2 |
| 207 | 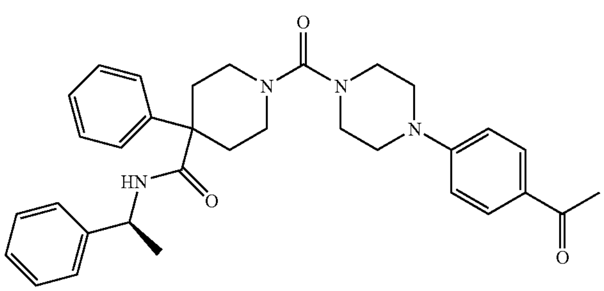 | 538.7 | 1-[4-(4-Acetyl-phenyl)-piperazine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-(4-piperazin-1-yl-phenyl)-ethanone (commercially available) | 539.4 |
| 208 | 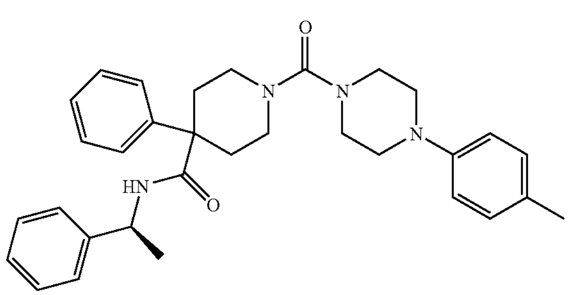 | 510.7 | 4-Phenyl-1-(4-p-tolyl-piperazine-1-carbonyl)-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-p-tolyl-piperazine (commercially available) | 511.5 |

TABLE 4-continued

| No | structure | MW calc. | systematic Name | starting materials | MW (MH+) |
|---|---|---|---|---|---|
| 209 | 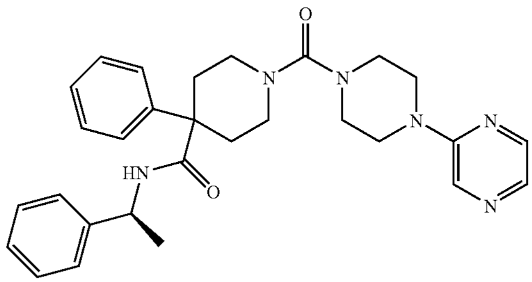 | 498.6 | 4-Phenyl-1-(2,3,5,6-tetrahydro-[1,2']bipyrazinyl-4-carbonyl)-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 3,4,5,6-tetrahydro-2H-[1,2']bipyrazinyl (commercially available) | 499.4 |
| 210 | 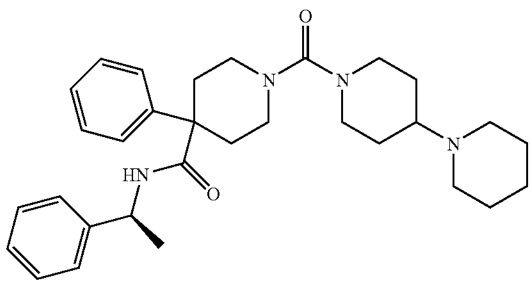 | 502.7 | 1-([1,4']Bipiperidinyl-1'-carbonyl)-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and [1,4']bipiperidinyl (commercially available) | 503.4 |
| 211 | 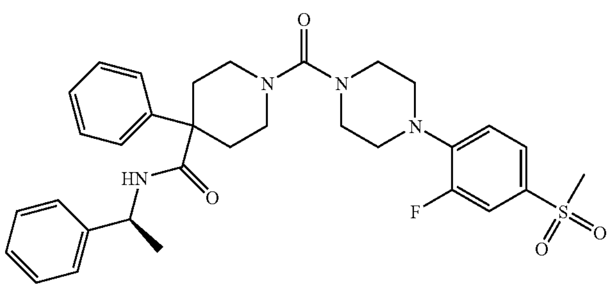 | 592.7 | 1-[4-(2-Fluoro-4-methanesulfonyl-phenyl)-piperazine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-(2-fluoro-4-methanesulfonyl-phenyl)-piperazine (commercially available) | 593.3 |
| 212 | 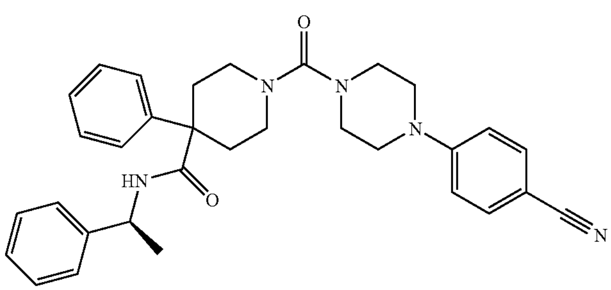 | 521.7 | 1-[4-(4-Cyano-phenyl)-piperazine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 4-piperazin-1-yl-benzonitrile (commercially available) | 522.4 |
| 213 | 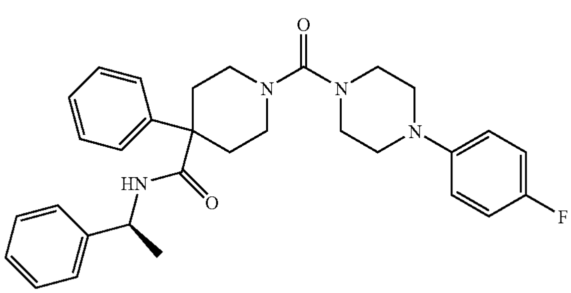 | 514.6 | 1-[4-(4-Fluoro-phenyl)-piperazine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-(4-fluoro-phenyl)-piperazine (commercially available) | 515.4 |

TABLE 4-continued

| No | structure | MW calc. | systematic Name | starting materials | MW (MH+) |
|---|---|---|---|---|---|
| 214 | 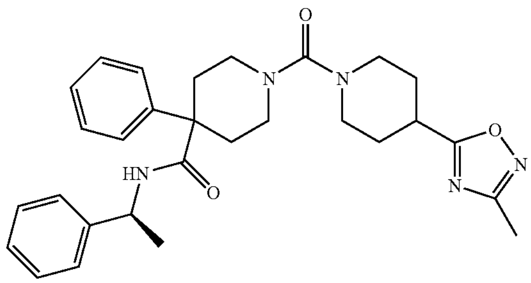 | 501.6 | 1-[4-(3-Methyl-[1,2,4]oxadiazol-5-yl)-piperidine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 4-(3-methyl-[1,2,4]oxadiazol-5-yl)-piperidine (commercially available) | 502.3 |
| 215 | 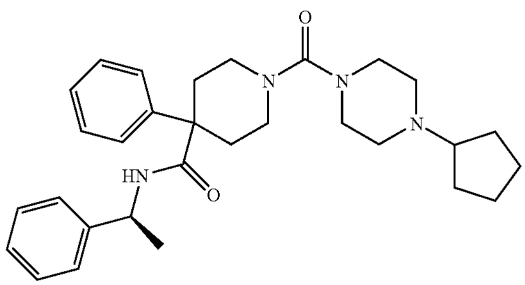 | 488.7 | 1-(4-Cyclopentyl-piperazine-1-carbonyl)-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-cyclopentyl-piperazine (commercially available) | 489.4 |
| 216 | 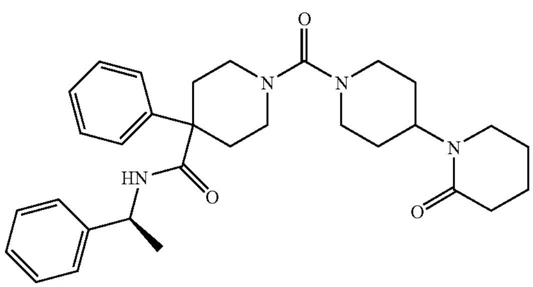 | 516.7 | 1-(2-Oxo-[1,4']bipiperidinyl-1'-carbonyl)-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and [1,4']bipiperidinyl-2-one (commercially available) | 517.3 |
| 217 | 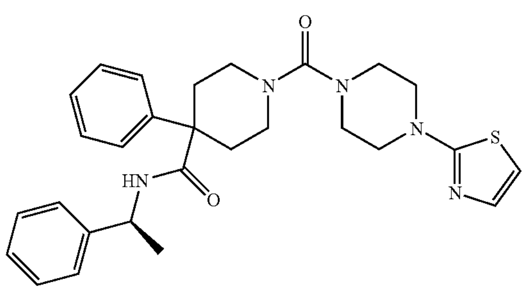 | 503.7 | 4-Phenyl-1-(4-thiazol-2-yl-piperazine-1-carbonyl)-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-thiazol-2-yl-piperazine (commercially available) | 504.3 |
| 218 | 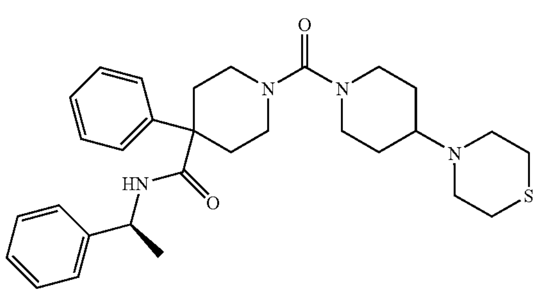 | 520.7 | 4-Phenyl-1-(4-thiomorpholin-4-yl-piperidine-1-carbonyl)-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 4-piperidin-4-yl-thiomorpholine (commercially available) | 521.4 |

TABLE 4-continued

| No | structure | MW calc. | systematic Name | starting materials | MW (MH+) |
|---|---|---|---|---|---|
| 219 | 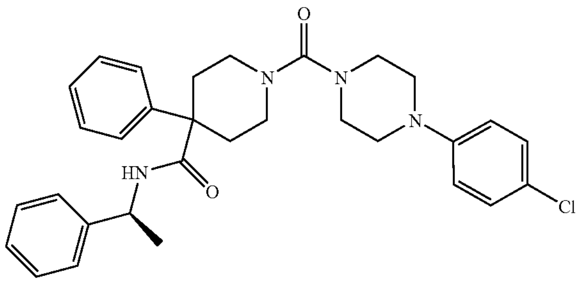 | 531.1 | 1-[4-(4-Chloro-phenyl)-piperazine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-(4-chloro-phenyl)-piperazine (commercially available) | 531.3 |
| 220 | 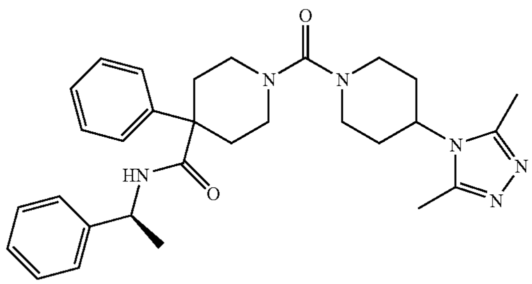 | 514.7 | 1-[4-(3,5-Dimethyl-[1,2,4]triazol-4-yl)-piperidine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 4-(3,5-dimethyl-[1,2,4]triazol-4-yl)-piperidine (commercially available) | 515.4 |
| 221 | 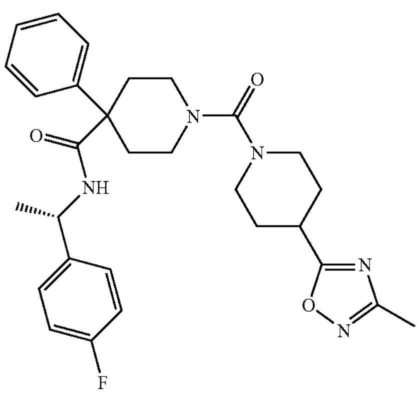 | 519.6 | 1-[4-(3-Methyl-[1,2,4]oxadiazol-5-yl)-piperidine-1-carbonyl]-4-phenyl-piperidine-4-carboxylic acid [(S)-1-(4-fluoro-phenyl)-ethyl]-amide | 4-[(S)-1-(4-Fluoro-phenyl)-ethylcarbamoyl]-4-phenyl-piperidine-1-carbonyl chloride (intermediate 29) and 4-(3-methyl-[1,2,4]oxadiazol-5-yl)-piperidine (commercially available) | 520.3 |
| 222 | 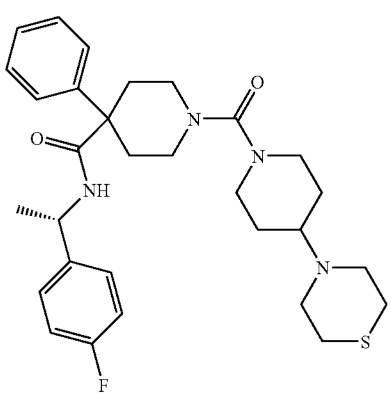 | 538.7 | 4-Phenyl-1-(4-thiomorpholin-4-yl-piperidine-1-carbonyl)-piperidine-4-carboxylic acid [(S)-1-(4-fluoro-phenyl)-ethyl]-amide | 4-[(S)-1-(4-Fluoro-phenyl)-ethylcarbamoyl]-4-phenyl-piperidine-1-carbonyl chloride (intermediate 29) and 4-piperidin-4-yl-thiomorpholine (commercially available | 539.5 |

TABLE 4-continued

| No | structure | MW calc. | systematic Name | starting materials | MW (MH+) |
|---|---|---|---|---|---|
| 223 | 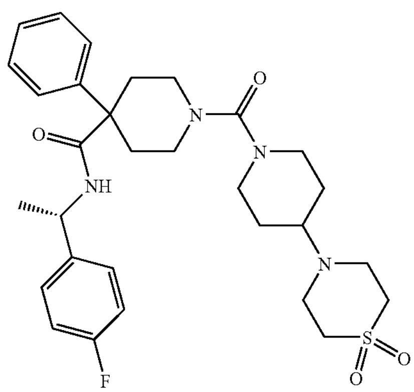 | 570.7 | 1-[4-(1,1-Dioxo-1λ6-thiomorpholin-4-yl)-piperidine-1-carbonyl]-4-phenyl-piperidine-4-carboxylic acid [(S)-1-(4-fluoro-phenyl)-ethyl]-amide | 4-[(S)-1-(4-Fluoro-phenyl) ethylcarbamoyl]-4-phenyl-piperidine-1-carbonyl chloride (intermediate 29) and 4-piperidin-4-yl-thiomorpholine 1,1-dioxide (commercially available) | 571.4 |
| 224 | 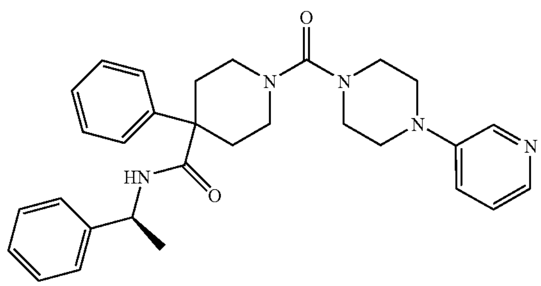 | 497.6 | 4-Phenyl-1-(4-pyridin-3-yl-piperazine-1-carbonyl)-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-pyridin-3-yl-piperazine (commercially available) | 498.5 |
| 225 | 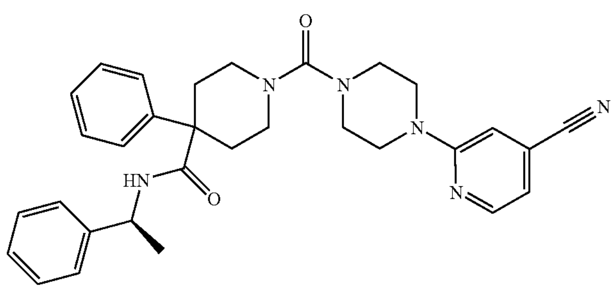 | 522.7 | 1-[4-(4-Cyano-pyridin-2-yl)-piperazine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 2-piperazin-1-yl-isonicotinonitrile (commercially available) | 523.5 |
| 226 | 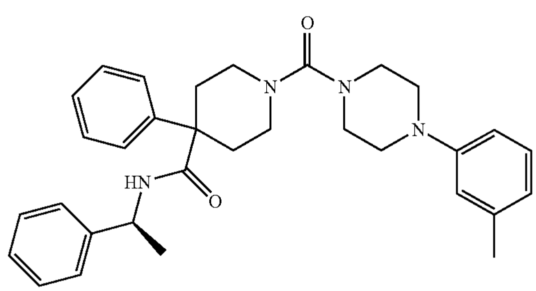 | 510.7 | 4-Phenyl-1-(4-m-tolyl-piperazine-1-carbonyl)-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-m-tolyl-piperazine (commercially available) | 511.5 |
| 227 | 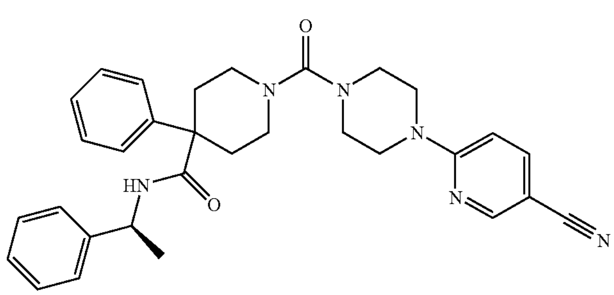 | 522.7 | 1-[4-(5-Cyano-pyridin-2-yl)-piperazine-1-carbonyl]-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 6-piperazin-1-yl-nicotinonitrile (commercially available) | 523.5 |

TABLE 4-continued

| No | structure | MW calc. | systematic Name | starting materials | MW (MH+) |
|---|---|---|---|---|---|
| 228 | 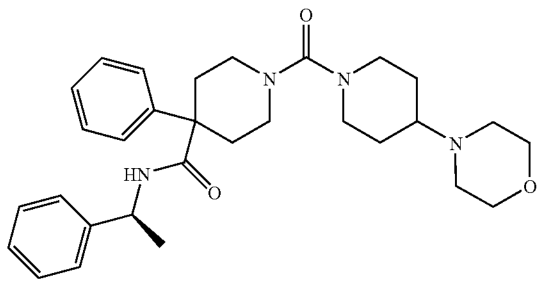 | 504.7 | 1-(4-Morpholin-4-yl-piperidine-1-carbonyl)-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 4-piperidin-4-yl-morpholine (commercially available) | 505.4 |
| 229 | 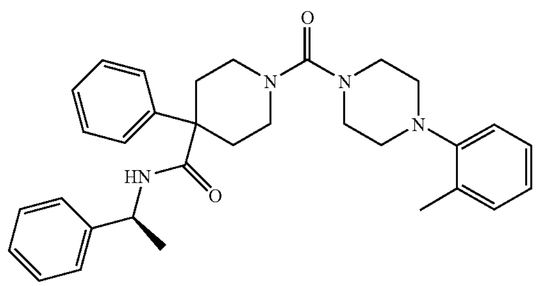 | 510.7 | 4-Phenyl-1-(4-o-tolyl-piperazine-1-carbonyl)-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-o-tolyl-piperazine (commercially available) | 511.5 |
| 230 | 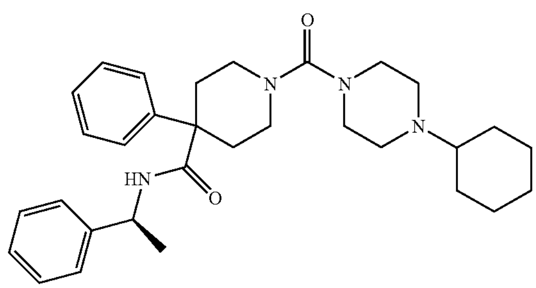 | 502.7 | 1-(4-Cyclohexyl-piperazine-1-carbonyl)-4-phenyl-piperidine-4-carboxylic acid ((S)-1-phenyl-ethyl)-amide | 4-Phenyl-4-((S)-1-phenyl-ethylcarbamoyl)-piperidine-1-carbonyl chloride (intermediate 30) and 1-cyclohexyl-piperazine (commercially available) | 503.4 |

Example 231

1-[4-(4-Fluoro-phenyl)-piperazine-1-carbonyl]-4-phenyl-piperidine-4-carboxylic acid ((S)-1-phenyl-propyl)-amide

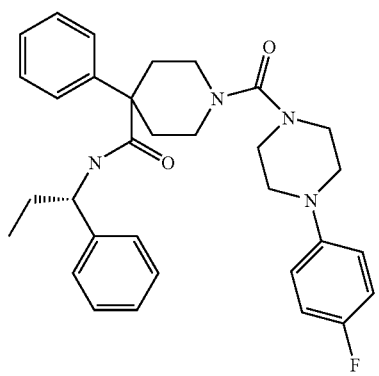

i) 4-Phenyl-piperidine-4-carboxylic acid ((S)-1-phenyl-propyl)-amide

4-Phenyl-piperidine-4-carboxylic acid ((S)-1-phenyl-propyl)-amide; TFA-salt (500 mg, 1.146 mmol) was dissolved in ethyl acetate and saturated aqueous sodium bicarbonate solution. The aqueous phase was extracted three times with ethyl acetate, the organic layers were combined, dried over $Na_2SO_4$, and the solvents were evaporated to give 331 mg 4-phenyl-piperidine-4-carboxylic acid ((S)-1-phenyl-propyl)-amide.

ii) 1-[4-(4-Fluoro-phenyl)-piperazine-1-carbonyl]-4-phenyl-piperidine-4-carboxylic acid ((S)-1-phenyl-propyl)-amide To a solution of 66.4 mg (0.409 mmol) N,N'-carbonyldiimidazole in dry THF (4 mL) was added 74 mg (0.409 mmol) 1-(4-fluorophenyl)piperazine and the reaction mixture was stirred at room temperature for 3 h. 40 mg (0.124 mmol) 4-Phenyl-piperidine-4-carboxylic acid ((S)-1-phenyl-propyl)-amide dissolved THF (2 mL) was added. The mixture was heated under reflux for 12 h. The reaction mixture was subjected to flash chromatography with n-heptane and ethyl acetate over a 20 g silica gel column to yield 62 mg 1-[4-(4- fluoro-phenyl)-piperazine-1-carbonyl]-4-phenyl-piperidine-4-carboxylic acid ((S)-1-phenyl-propyl)-amide. MS ISP (m/e): 529.3 (100) [(M+H)+].

Example 232

4-Phenyl-1-(4-phenyl-piperazine-1-carbonyl)-piperidine-4-carboxylic acid ((S)-1-phenyl-ethyl)-amide

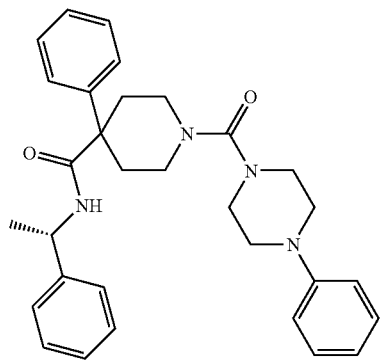

In analogy to the procedure described for the synthesis of 1-[4-(4-Fluoro-phenyl)-piperazine-1-carbonyl]-4-phenyl-piperidine-4-carboxylic acid ((S)-1-phenyl-propyl)-amide (example 231) the title compound was prepared from 4-Phenyl-piperidine-4-carboxylic acid ((S)-1-phenyl-ethyl)-amide, CDI and 1-phenyl-piperazine. MS ISP (m/e): 497.5 [(M+H)+].

Example 233

1-[4-(4-Fluoro-phenyl)-piperazine-1-carbonyl]-4-phenyl-piperidine-4-carboxylic acid ((S)-1-cyclohexyl-ethyl)-amide

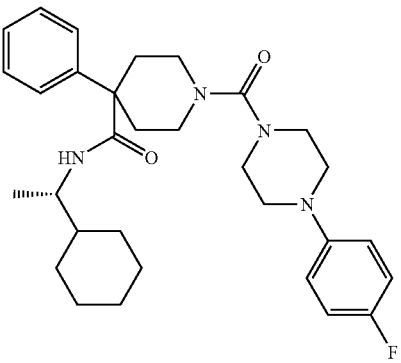

In analogy to the procedure described for the synthesis of 1-[4-(4-Fluoro-phenyl)-piperazine-1-carbonyl]-4-phenyl-piperidine-4-carboxylic acid ((S)-1-phenyl-propyl)-amide (example 231) the title compound was prepared from 4-Phenyl-piperidine-4-carboxylic acid ((S)-1-phenyl-ethyl)-amide, CDI and 1-(4-fluorophenyl)piperazine. MS ISP (m/e): 521.5 [(M+H)+].

As mentioned earlier, the compounds of formula I and their pharmaceutically usable addition salts possess valuable pharmacological properties. It has been found that the compounds of the present invention are antagonists of neurokinin 3 (NK-3) receptors. The compounds were investigated in accordance with the tests given hereinafter.

Experimental Procedure

The compounds were investigated in accordance with the tests given hereinafter
[3H]SR142801 Competition Binding Assay hNK3 receptor binding experiment were performed using [3H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM $MnCl_2$, 1 µM phosphoramidon, 0.1% BSA binding buffer at pH 7.4 to a final assay concentration of 5 µg protein/well. For inhibition experiments, membranes were incubated with [3H] SR142801 at a concentration equal to $K_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Can berra Packard S. A., Zurich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). $IC_{50}$ values were derived from the inhibition curve and the affinity constant ($K_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

The hNK-3 receptor affinity <0.10 µM of some compounds of the invention are listed in the following table.

| Example | Data $K_i$ [µM] |
| --- | --- |
| 1 | 0.0293 |
| 2 | 0.0229 |
| 3 | 0.0482 |
| 4 | 0.0196 |
| 5 | 0.0239 |
| 6 | 0.0409 |
| 7 | 0.0396 |
| 8 | 0.0844 |
| 9 | 0.0218 |
| 10 | 0.0768 |
| 11 | 0.044 |
| 12 | 0.0504 |
| 14 | 0.0981 |
| 18 | 0.0966 |
| 21 | 0.0998 |
| 22 | 0.0658 |
| 27 | 0.0765 |
| 28 | 0.0762 |
| 34 | 0.0985 |

| Example | Data $K_i$ [µM] |
|---|---|
| 35 | 0.0687 |
| 38 | 0.0214 |
| 39 | 0.0808 |
| 40 | 0.0285 |
| 41 | 0.0094 |
| 43 | 0.0032 |
| 44 | 0.0785 |
| 45 | 0.0267 |
| 47 | 0.0247 |
| 52 | 0.0241 |
| 53 | 0.0232 |
| 54 | 0.0072 |
| 55 | 0.0148 |
| 56 | 0.0206 |
| 59 | 0.037 |
| 60 | 0.0315 |
| 61 | 0.0379 |
| 62 | 0.0635 |
| 63 | 0.0449 |
| 64 | 0.0727 |
| 66 | 0.059 |
| 68 | 0.0209 |
| 69 | 0.0773 |
| 71 | 0.0284 |
| 72 | 0.0158 |
| 74 | 0.001 |
| 75 | 0.0039 |
| 76 | 0.0029 |
| 77 | 0.0122 |
| 78 | 0.0118 |
| 79 | 0.0095 |
| 80 | 0.0041 |
| 81 | 0.006 |
| 82 | 0.0053 |
| 83 | 0.0011 |
| 84 | 0.0028 |
| 85 | 0.0027 |
| 88 | 0.0062 |
| 89 | 0.0183 |
| 90 | 0.0026 |
| 91 | 0.0076 |
| 92 | 0.0051 |
| 98 | 0.0336 |
| 101 | 0.0174 |
| 102 | 0.0172 |
| 104 | 0.0112 |
| 105 | 0.0052 |
| 106 | 0.0563 |
| 109 | 0.082 |
| 110 | 0.0522 |
| 111 | 0.0398 |
| 112 | 0.0828 |
| 113 | 0.0356 |
| 114 | 0.0905 |
| 116 | 0.0226 |
| 122 | 0.0257 |
| 126 | 0.0937 |
| 129 | 0.012 |
| 135 | 0.0267 |
| 136 | 0.0549 |
| 140 | 0.0078 |
| 142 | 0.0382 |
| 143 | 0.0069 |
| 144 | 0.0109 |
| 145 | 0.0364 |
| 146 | 0.036 |
| 147 | 0.0176 |
| 148 | 0.0058 |
| 151 | 0.0115 |
| 153 | 0.038 |
| 154 | 0.075 |
| 155 | 0.075 |
| 156 | 0.087 |
| 157 | 0.0094 |
| 158 | 0.011 |
| 160 | 0.092 |
| 161 | 0.0046 |
| 162 | 0.075 |
| 163 | 0.041 |
| 164 | 0.012 |
| 165 | 0.066 |
| 167 | 0.017 |
| 168 | 0.036 |
| 171 | 0.054 |
| 173 | 0.043 |
| 174 | 0.024 |
| 175 | 0.048 |
| 176 | 0.077 |
| 178 | 0.019 |
| 179 | 0.018 |
| 185 | 0.0636 |
| 187 | 0.0767 |
| 191 | 0.017 |
| 193 | 0.0074 |
| 194 | 0.035 |
| 195 | 0.015 |
| 196 | 0.0022 |
| 197 | 0.0071 |
| 198 | 0.0215 |
| 199 | 0.0051 |
| 200 | 0.015 |
| 202 | 0.0068 |
| 203 | 0.0087 |
| 204 | 0.0792 |
| 206 | 0.0798 |
| 207 | 0.0363 |
| 208 | 0.0709 |
| 209 | 0.0584 |
| 211 | 0.0294 |
| 213 | 0.0088 |
| 214 | 0.009 |
| 215 | 0.0206 |
| 216 | 0.0172 |
| 218 | 0.0052 |
| 219 | 0.0125 |
| 220 | 0.0639 |
| 221 | 0.0117 |
| 222 | 0.01 |
| 223 | 0.006 |
| 224 | 0.0638 |
| 225 | 0.0506 |
| 226 | 0.0648 |
| 227 | 0.0249 |
| 229 | 0.0349 |
| 230 | 0.0221 |
| 231 | 0.0034 |
| 232 | 0.0363 |
| 233 | 0.0053 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:
1. A compound of formula I

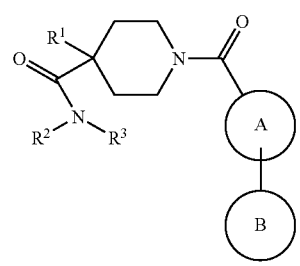

wherein
$R^1$ is
aryl optionally substituted by halogen, lower alkyl substituted by halogen;
$R^2$ is
CRR'-aryl or heteroaryl, each of which is optionally substituted by halogen, lower alkyl, lower alkyl substituted by halogen or cyano,
CRR'-cycloalkyl,
CRR'-lower alkyl, or
NR-aryl or NR-heteroaryl, wherein aryl and heteroaryl are each optionally substituted by halogen, lower alkyl, lower alkyl substituted by halogen or cyano, or is NR-cycloalkyl, indan-1-yl or indan-2-yl, each of which is optionally substituted by hydroxy;
$R^3$ is hydrogen or lower alkyl, or
$R^2$ and $R^3$ together with the N-atom to which they are attached form a 2,3-dihydro-1-H-isoindol group or a piperidine ring, which is optionally substituted by a heteroaryl group;
R and R' are each independently hydrogen, $(CH_2)_n$-cycloalkyl, lower alkyl, lower alkyl substituted by halogen or hydroxy, or
R and R' together with the carbon atom to which they are attached form a cycloalkyl ring;

is aryl, optionally substituted by lower alkyl or =O, or is cycloalkyl;

is heteroaryl, optionally substituted by lower alkyl, lower alkoxy, halogen, lower alkyl substituted by halogen, cyano, amino, C(O)-lower alkyl, C(O)NH$_2$, S(O)$_2$-lower alkyl or =O, or is cycloalkyl;
or a pharmaceutically active salt thereof.

2. The compound of claim 1 having formula Ia

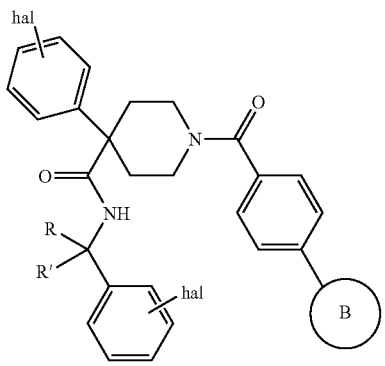

wherein
hal is halogen;
R and R' are each independently hydrogen, $(CH_2)_n$-cycloalkyl, lower alkyl, lower alkyl substituted by halogen or hydroxy, or
R and R' together with the carbon atom to which they are attached form a cycloalkyl ring;

is heteroaryl, optionally substituted by lower alkyl, lower alkoxy, halogen, lower alkyl substituted by halogen, cyano, amino, C(O)-lower alkyl, $C(O)NH_2$, $S(O)_2$-lower alkyl or =O, or is cycloalkyl;
or a pharmaceutically active salt thereof.

3. The compound of claim 2, selected from the group consisting of
1-[4-(5-methyl-[1,2,4]oxadiazol-3-yl)-benzoyl]-4-phenyl-piperidine-4-carboxylic acid ((S)-1-phenyl-ethyl)-amide;
1-[4-(3-methyl-[1,2,4]oxadiazol-5-yl)-benzoyl]-4-phenyl-piperidine-4-carboxylic acid ((S)-1-phenyl-ethyl)-amide;
1-[4-(3-methyl-[1,2,4]oxadiazol-5-yl)-benzoyl]-4-phenyl-piperidine-4-carboxylic acid [(S)-1-(4-fluoro-phenyl)-ethyl]-amide;
4-(4-fluoro-phenyl)-1-[4-(3-methyl-[1,2,4]oxadiazol-5-yl)-benzoyl]-piperidine-4-carboxylic acid ((S)-1-phenyl-ethyl)-amide;
1-[4-(3-methyl-[1,2,4]oxadiazol-5-yl)-benzoyl]-4-phenyl-piperidine-4-carboxylic acid ((S)-1-phenyl-propyl)-amide;
and
4-(4-fluoro-phenyl)-1-[4-(3-methyl-[1,2,4]oxadiazol-5-yl)-benzoyl]-piperidine-4-carboxylic acid [(S)-1-(4-fluoro-phenyl)-ethyl]-amide.

4. The compound of claim 2, selected from the group consisting of
4-(4-fluoro-phenyl)-1-[4-(3-methyl-[1,2,4]oxadiazol-5-yl)-benzoyl]-piperidine-4-carboxylic acid [1-(4-fluoro-phenyl)-cyclopropyl]-amide;
4-(4-fluoro-phenyl)-1-[4-(3-methyl-[1,2,4]oxadiazol-5-yl)-benzoyl]-piperidine-4-carboxylic acid [(S)-1-(3-fluoro-phenyl)-ethyl]-amide;
4-(4-fluoro-phenyl)-1-[4-(3-methyl-[1,2,4]oxadiazol-5-yl)-benzoyl]-piperidine-4-carboxylic acid [(S)-cyclopropyl-(3-fluoro-phenyl)-methyl]-amide;
4-(4-fluoro-phenyl)-1-[4-(5-methyl-[1,2,4]oxadiazol-3-yl)-benzoyl]-piperidine-4-carboxylic acid [(S)-cyclopropyl-(3-fluoro-phenyl)-methyl]-amide; and
4-(4-fluoro-phenyl)-1-[4-(3-methyl-[1,2,4]oxadiazol-5-yl)-benzoyl]-piperidine-4-carboxylic acid [(SR)-2,2,2-trifluoro-1-(4-fluoro-phenyl)-ethyl]amide.

5. The compound of claim 1 having formula Ib

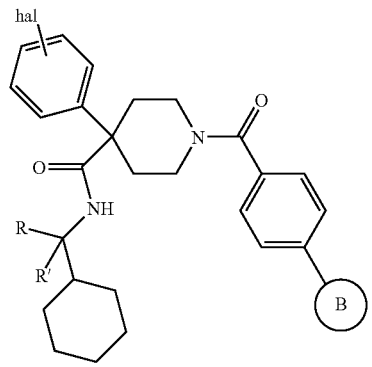

wherein
hal is halogen;
R and R' are each independently hydrogen, $(CH_2)_n$-cycloalkyl, lower alkyl, lower alkyl substituted by halogen or hydroxy, or
R and R' together with the carbon atom to which they are attached form a cycloalkyl ring;

is heteroaryl, optionally substituted by lower alkyl, lower alkoxy, halogen, lower alkyl substituted by halogen, cyano, amino, C(O)-lower alkyl, $C(O)NH_2$, $S(O)_2$-lower alkyl or =O, or is cycloalkyl;
or a pharmaceutically active salt thereof.

6. The compound of claim 5, selected from the group consisting of
1-[4-(3-methyl-[1,2,4]oxadiazol-5-yl)-benzoyl]-4-phenyl-piperidine-4-carboxylic acid ((S)-1-cyclohexyl-ethyl)-amide;
1-[4-(5-methyl-[1,2,4]oxadiazol-3-yl)-benzoyl]-4-phenyl-piperidine-4-carboxylic acid ((S)-1-cyclohexyl-ethyl)-amide; and
4-(4-fluoro-phenyl)-1-[4-(3-methyl-[1,2,4]oxadiazol-5-yl)-benzoyl]-piperidine-4-carboxylic acid ((S)-1-cyclohexyl-ethyl)-amide.

7. A pharmaceutical composition comprising a therapeutically effective amount of a compound of formula I

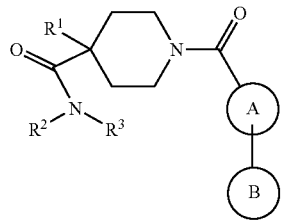

wherein $R^1$ is
aryl optionally substituted by halogen, lower alkyl substituted by halogen;

$R^2$ is
CRR'-aryl or heteroaryl, each of which is optionally substituted by halogen, lower alkyl, lower alkyl substituted by halogen or cyano,
CRR'-cycloalkyl,
CRR'-lower alkyl, or
NR-aryl or NR-heteroaryl, wherein aryl and heteroaryl are each optionally substituted by halogen, lower alkyl, lower alkyl substituted by halogen or cyano, or is NR-cycloalkyl, indan-1-yl or indan-2-yl, each of which is optionally substituted by hydroxy;

$R^3$ is hydrogen or lower alkyl, or
$R^2$ and $R^3$ together with the N-atom to which they are attached form a 2,3-dihydro-1-H-isoindol group or a piperidine ring, which is optionally substituted by a heteroaryl group;
R and R' are each independently hydrogen, $(CH_2)_n$-cycloalkyl, lower alkyl, lower alkyl substituted by halogen or hydroxy, or
R and R' together with the carbon atom to which they are attached form a cycloalkyl ring;

is aryl, optionally substituted by lower alkyl or =O, or is cycloalkyl;

is heteroaryl, optionally substituted by lower alkyl, lower alkoxy, halogen, lower alkyl substituted by halogen, cyano, amino, C(O)-lower alkyl, C(O)NH$_2$, S(O)$_2$-lower alkyl or =O, or is cycloalkyl;

or a pharmaceutically active salt thereof and a pharmaceutically acceptable carrier.

\* \* \* \* \*